(12) United States Patent
Forsyth et al.

(10) Patent No.: US 9,221,852 B2
(45) Date of Patent: Dec. 29, 2015

(54) METHOD FOR MAKING ORGANODIPHOSPHITES FROM PHOSPHOROCHLORIDITES CHARACTERIZED BY MEASURING SIDE-PRODUCT LEVELS TO DETERMINE FURTHER ADDITIONS

(71) Applicant: INVISTA North America S.a r.l., Wilmington, DE (US)

(72) Inventors: Stewart Forsyth, Wilmington, DE (US);
John Arthur Turner, Cleveland (GB);
Keith Whiston, Darlington (GB);
Thomas E Vos, Beaumont, TX (US)

(73) Assignee: INVISTA North America S.a.r.l., Wilmington, DE (US)

( * ) Notice: Subject to any disclaimer, the term of this patent is extended or adjusted under 35 U.S.C. 154(b) by 0 days.

(21) Appl. No.: 14/354,110

(22) PCT Filed: Oct. 15, 2012

(86) PCT No.: PCT/IB2012/002472
§ 371 (c)(1),
(2) Date: Apr. 24, 2014

(87) PCT Pub. No.: WO2013/076569
PCT Pub. Date: May 30, 2013

(65) Prior Publication Data
US 2014/0343313 A1    Nov. 20, 2014

Related U.S. Application Data

(60) Provisional application No. 61/551,467, filed on Oct. 26, 2011.

(51) Int. Cl.
*C07F 9/144*    (2006.01)
*C07F 9/145*    (2006.01)
*C07F 9/146*    (2006.01)
*C07F 9/6574*   (2006.01)

(52) U.S. Cl.
CPC .............. *C07F 9/144* (2013.01); *C07F 9/145* (2013.01); *C07F 9/146* (2013.01); *C07F 9/65744* (2013.01)

(58) Field of Classification Search
CPC .......... C07F 9/144; C07F 9/145; C07F 9/146
See application file for complete search history.

(56) References Cited

U.S. PATENT DOCUMENTS

| | | | |
|---|---|---|---|
| 5,235,113 A | 8/1993 | Sato et al. | |
| 6,069,267 A | 5/2000 | Tam | |

FOREIGN PATENT DOCUMENTS

| | | | |
|---|---|---|---|
| CN | 101405292 A | 4/2009 | |
| CN | 101484417 A | 7/2009 | |
| WO | 96/22968 A1 | 8/1996 | |
| WO | 2004/050588 A2 | 6/2004 | |
| WO | 2004/091780 A1 | 10/2004 | |
| WO | 2007/109005 A2 | 9/2007 | |
| WO | 2008/008930 A2 | 1/2008 | |
| WO | 2010/123743 A1 | 10/2010 | |
| WO | 2010/123747 A1 | 10/2010 | |

OTHER PUBLICATIONS

International Search Report and Written Opinion received for PCT Patent Application No. PCT/IB2012/002472, mailed on Mar. 15, 2013, 14 Pages.
International Preliminary Report on Patentability received for PCT Patent Application No. PCT/IB2012/002472, mailed on Mar. 3, 2014, 56 pages.
International Preliminary Report on Patentability received for PCT Patent Application No. PCT/IB2012/002472, mailed Mar. 3, 2014. (56 pages).
"Chinese Application Serial No. 201280052751.7, Office Action mailed Jul. 9, 2015", 8 pgs.

*Primary Examiner* — Sun Jae Yoo
(74) *Attorney, Agent, or Firm* — Robert B. Furr, Jr.; Nicholas P. Lanzatella

(57) ABSTRACT

Claimed is a process for producing a phosphorus-containing ligand, preferably a diphosphite ligand structure (DLS) such as structure I. The method includes contacting a phosphorochloridite (structure II) with a compound having the structure X—OH (which can be a bisaryl compound), and a tertiary organic amine to provide structure I' and as preferred embodiment structure I.

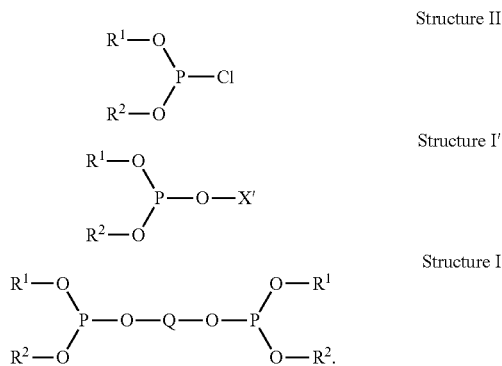

19 Claims, No Drawings

METHOD FOR MAKING ORGANODIPHOSPHITES FROM PHOSPHOROCHLORIDITES CHARACTERIZED BY MEASURING SIDE-PRODUCT LEVELS TO DETERMINE FURTHER ADDITIONS

FIELD OF THE INVENTION

The invention relates to a method for the synthesis of a phosphorus-containing ligand structure.

BACKGROUND OF THE INVENTION

A key intermediate in the production of nylon is adiponitrile (ADN). ADN is commercially produced via hydrocyanation of 1,3-butadiene and 3-pentenenitrile (3PN) in the presence of a catalyst including nickel(0) and phosphite ligand. The phosphite ligand used commercially is a monodentate phosphite, such as a triarylphosphite, that forms nickel-ligand complexes serving as catalyst precursors for the reactions. Although useful, monodentate phosphites can result in relatively low catalyst activity and relatively high nickel consumption.

Recently, significant improvements in nickel catalyst activity and yield to 3PN and ADN have been realized by using catalysts including nickel(0) and bidentate phosphites as ligands. Bidentate phosphite ligands, in general, contain two phosphorus donor atoms that can form cyclic chelate structures with a single transition metal.

Bidentate phosphites of the general structure $(RO)_2P(OZO)P(OR)_2$, also referred to as diphosphites herein, are of special interest. Traditionally, such diphosphites can be synthesized by preparing a phosphorochloridite, $(RO)_2PCl$, from the reaction of $PCl_3$ with ROH in the presence of a tertiary organic amine. Then in a subsequent reaction, a difunctional alcohol, such as HO—Z—OH, can react with the phosphorochloridite in the presence of additional tertiary organic amine, giving $(RO)_2P(OZO)P(OR)_2$. The tertiary organic amine can neutralize the HCl co-product in both reaction steps through the formation of a tertiary organic amine hydrogen chloride salt. The nature of the ROH and the HO—Z—OH as well as the conditions chosen for each reaction step can influence the selectivity to the desired products.

U.S. Pat. No. 5,235,113 and WO 96/22968, for example, disclose the synthesis of diphosphites. U.S. Pat. No. 5,235,113 discloses a process for the preparation of a diphosphite of structure $(RO)_2P(OAO)P(OR)_2$ where A is biphenyl and R is 3,6-di-t-butyl-2-naphthyl. WO 96/22968 discloses syntheses of multidentate phosphite compounds of the type $(ArO)_2P(OZO)P(OAr)_2$, where Ar and Z are substituted or unsubstituted aryl groups.

U.S. Pat. No. 6,069,267 provides a process for the preparation of organodiphosphites of the general formula $(R^1O)_2P(OZO)P(OR^1)_2$, wherein $R^1$ and Z are different substituted or unsubstituted aryl groups WO 2004/050588 discloses that low temperature and viscosity of the product mixture below 0° C., for example between 0° C. and –20° C., add significantly to operating cost and process complexity.

WO 2004/091780 also describes a process for preparing a crude ligand mixture including bidentate phosphite ligands of the structural formula $(R^1O)_2P(OZO)P(OR^1)_2$ by contacting a first reaction product including $(R^1O)_2PCl$ at a temperature between about –25° C. and about +35° C. with about one half molar equivalent of HO—Z—OH in the presence of an organic base.

WO 2010/123743 and WO 2010/123747 describe examples of methods for making organodiphosphites.

SUMMARY OF THE INVENTION

Various embodiments of the present invention provide a method for producing a phosphorus-containing ligand structure having the following chemical structure

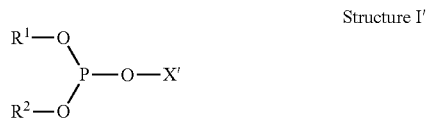

Structure I'

The method includes contacting a phosphorochloridite of the following structure,

Structure II with a compound having the chemical structure X—OH and a tertiary organic amine to provide a final reaction mixture including the phosphorus-containing ligand structure. The contacting includes providing a pre-determined limit for a mole percent of phosphorus present as at least one side-product in the final reaction mixture. The contacting also includes adding the X—OH to the phosphorochloridite in a first serial addition, to provide a first reaction mixture. The contacting also includes determining a mole percent of phosphorus present in the first reaction mixture as the at least one side-product. The contacting also includes using a comparison of the mole percent of phosphorus present in the first reaction mixture as the at least one side-product to the pre-determined limit for the mole percent of phosphorus present as the at least one side-product in the final reaction mixture, to determine an amount of a compound selected from the group consisting of the X—OH, water, and an alcohol having the chemical structure $R^1$—OH or $R^2$—OH, to add in a second serial addition. The contacting also includes adding the second serial addition to the first reaction mixture, including a compound selected from the group consisting of the X—OH, water, or the alcohol having the chemical structure $R^1$—OH or $R^2$—OH, to provide a second reaction mixture. The contacting also either includes performing third addition steps, or the final reaction mixture is the second reaction mixture. The third addition steps, if performed, include optionally using a comparison of the mole percent of phosphorus present in the second reaction mixture as the at least one side-product to the pre-determined limit for the mole percent of phosphorus present as the at least one side-product in the final reaction mixture, to determine an amount of a compound selected from the group consisting of the X—OH, water, and the alcohol having the chemical structure $R^1$—OH or $R^2$—OH, to add in a third serial addition. The third addition steps, if performed, include optionally determining a mole percent of phosphorus present in the second reaction mixture as the at least one side-product. The third addition steps, if performed, also include adding the third serial addition to the second reaction mixture, including a compound selected from the group consisting of the X—OH, water, and the alcohol having the chemical structure $R^1$—OH or $R^2$—OH, to provide the final reaction mixture. In this paragraph, $R^1$ and $R^2$ are the same or different, substituted or unsubstituted, monovalent aryl groups; $R^1$ and $R^2$ are bridged to one another or unbridged to one another; and each of X and X' are independently selected from the group consisting of hydrogen, alkyl, aryl, heteroaryl, aryloxy, heteroaryloxy, alkyloxy, alkoxyalkyl, acetal, carboaryloxy, carboalkoxy, arylcarbonyl, alkylcarbonyl, phosphitylbisaryl, phosphitylbisheteroaryl, hydroxybisaryl, hydroxybisheteroaryl, oxazole, amine, amide, nitrile, mercaptyl, and halogen groups.

Various embodiments of the present invention provide a method for producing a diphosphite ligand structure (DLS) having the following structure,

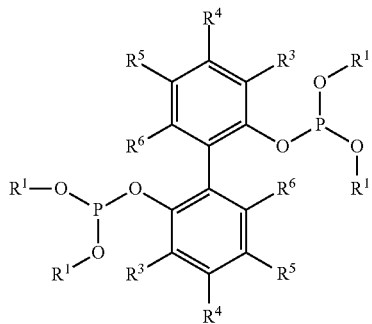

The method includes contacting a phosphorochloridite having the following structure,

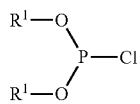

with a bisaryl compound having the following structure,

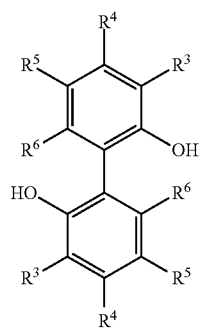

and a tertiary organic amine to provide a final reaction mixture including the diphosphite. The contacting includes providing a pre-determined limit for the mole percent of phosphorus present as C-phite ligand structure (CLS), having the chemical structure shown below, in the final reaction mixture

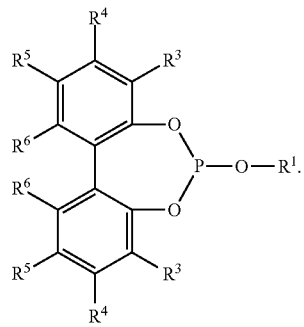

The contacting also includes adding the bisaryl compound to the phosphorochloridite in a first serial addition such that the moles of phosphorochloridite added in the first addition is greater than the number of moles of the bisaryl compound added in the first addition, to provide a first reaction mixture. The contacting also includes determining the mole percent of phosphorus present in the first reaction mixture as CLS. The contacting also includes using a comparison of the mole percent of phosphorus present in the first reaction mixture as CLS to the pre-determined limit for the mole percent of phosphorus present as CLS to determine an amount of a compound selected from the group consisting of at least one of the bisaryl compound, water, and an alcohol having the chemical structure $R^3$—OH, to add in a second serial addition such that the mole percent of phosphorus present as CLS in a second reaction mixture is less than or equal to the pre-determined limit for the mole percent of phosphorus present as CLS in the final reaction mixture. The contacting also includes adding the second serial addition to the first reaction mixture, including a compound selected from the group consisting of the bisaryl compound, water, and the alcohol having the chemical structure $R^1$—OH or $R^2$—OH, to provide the second reaction mixture. The contacting also includes either performing third addition steps, or the final reaction mixture is the second reaction mixture. The third addition steps, if performed, include optionally determining a mole percent of phosphorus present in the second reaction mixture as the at least one side-product. The third addition steps, if performed, include optionally using a comparison of the mole percent of phosphorus present in the second reaction mixture as the at least one side-product to the pre-determined limit for the mole percent of phosphorus present as the at least one side-product in the final reaction mixture, to determine an amount of a compound selected from the group consisting of the X—OH, water, and the alcohol having the chemical structure $R^1$—OH or $R^2$—OH, to add in a third serial addition. The third addition steps, if performed, include adding the third serial addition to the second reaction mixture, including a compound selected from the group consisting of the X—OH, water, and the alcohol having the chemical structure $R^1$—OH or $R^2$—OH, to provide the final reaction mixture. In this paragraph, $R^1$ and $R^2$ are the same or different, substituted or unsubstituted, monovalent aryl groups; each of $R^3$, $R^4$, $R^5$, $R^6$ is independently selected from the group consisting of hydrogen and $C_{1-10}$ alkyl.

Various embodiments of the present invention provide a method for producing a diphosphite ligand structure (DLS) having the following structure,

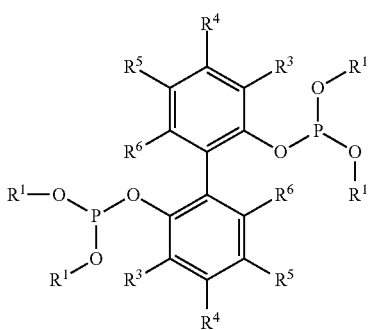

The method includes contacting a phosphorochloridite having the following structure,

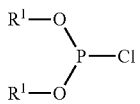

with a bisaryl compound having the following structure,

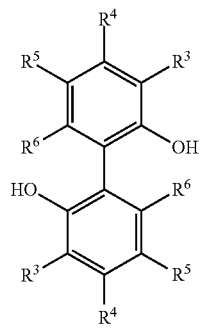

and a tertiary organic amine to provide a final reaction mixture including the diphosphite. The contacting includes providing a pre-determined limit for the mole percent of phosphorus present as T-phite ligand structure (TLS), having the chemical structure shown below, in the final reaction mixture

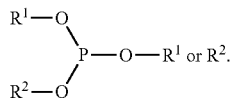

The contacting also includes adding the bisaryl compound to the phosphorochloridite in a first serial addition such that the moles of phosphorochloridite added in the first addition is greater than the number of moles of biaryl added in the first addition, to provide a first reaction mixture. The contacting also includes determining the mole percent of phosphorus present in the first reaction mixture as TLS. The contacting also includes using a comparison of the mole percent of phosphorus present in the first reaction mixture as TLS to the pre-determined limit for the mole percent of phosphorus present as TLS to determine an amount of a compound selected from the group consisting of the bisaryl compound, water, and an alcohol having the chemical structure $R^1$—OH, to add in a second serial addition such that the mole percent of phosphorus present as TLS in a second reaction mixture is less than or equal to the pre-determined limit for the mole percent of phosphorus present as TLS in the final reaction mixture. The contacting also includes adding the second serial addition to the first reaction mixture, including a compound selected from the group consisting of the bisaryl compound, water, and the alcohol having the chemical structure $R^1$—OH or $R^2$—OH, to provide the second reaction mixture. The contacting also includes either performing third addition steps, or the final reaction mixture is the second reaction mixture. The third addition steps, if performed, include optionally determining a mole percent of phosphorus present in the second reaction mixture as the at least one side-product. The third addition steps, if performed, also include optionally using a comparison of the mole percent of phosphorus present in the second reaction mixture as the at least one side-product to the pre-determined limit for the mole percent of phosphorus present as the at least one side-product in the final reaction mixture, to determine an amount of a compound selected from the group consisting of the X—OH, water, and the alcohol having the chemical structure $R^1$—OH or $R^2$—OH, to add in a third serial addition. The third addition steps, if performed, also include adding the third serial addition to the second reaction mixture, including a compound selected from the group consisting of the X—OH, water, and the alcohol having the chemical structure $R^1$—OH or $R^2$—OH, to provide the final reaction mixture. In this paragraph, $R^1$ and $R^2$ are the same or different, substituted or unsubstituted, monovalent aryl groups; and each of $R^3$, $R^4$, $R^5$, $R^6$ is independently selected from the group consisting of hydrogen and $C_{1-10}$ alkyl.

Various embodiments of the present invention provide a method for producing a diphosphite ligand structure (DLS) having the following structure,

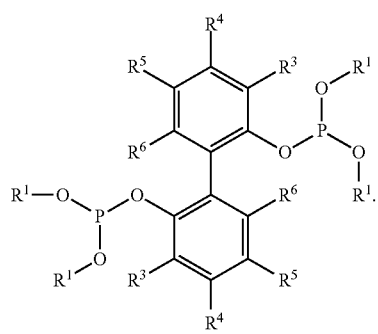

The method includes contacting a phosphorochloridite having the following structure,

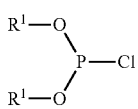

with a bisaryl compound having the following structure,

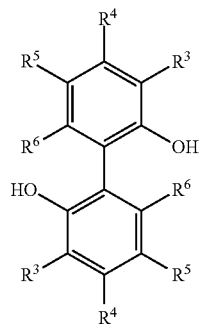

and a tertiary organic amine to provide a final reaction mixture including the diphosphite. The contacting includes providing a pre-determined limit for the mole percent of phosphorus present as a ligand hydrolysis product (LHP) in the final reaction mixture. The LHP includes at least one product derived by a process including hydrolysis of the DLS or of the phosphorochloridite; hydrolysis of a product derived from the DLS or from the phosphorochloridite; or reaction of the hydrolysis product of the DLS or of the phosphorochloridite, or reaction of the hydrolysis product of a product derived from the DLS or from the phosphorochloridite. The contacting includes adding the bisaryl compound to the phosphorochloridite in a first serial addition such that the moles of phosphorochloridite added in the first addition is greater than the number of moles of biaryl added in the first addition, to provide a first reaction mixture. The contacting includes determining the mole percent of phosphorus present in the first reaction mixture as LHP. The contacting includes using a comparison of the mole percent of phosphorus present in the first reaction mixture as LHP to the pre-determined limit for the mole percent of phosphorus present as LHP to determine an amount of a compound selected from the group consisting of the bisaryl compound, water, and an alcohol having the chemical structure $R^1$—OH, to add in a second serial addition such that the mole percent of phosphorus present as LHP in a second reaction mixture is less than or equal to the pre-determined limit for the mole percent of phosphorus present as LHP in the final reaction mixture. The contacting includes adding the second serial addition to the first reaction mixture, including a compound selected from the group consisting of the bisaryl compound, water, and the alcohol having the chemical structure $R^1$—OH or $R^2$—OH, to provide the second reaction mixture. The contacting also includes either performing third addition steps or the final reaction mixture is the second reaction mixture. The third addition steps, if performed, include optionally determining a mole percent of phosphorus present in the second reaction mixture as the at least one side-product. The third addition steps, if performed, include optionally using a comparison of the mole percent of phosphorus present in the second reaction mixture as the at least one side-product to the pre-determined limit for the mole percent of phosphorus present as the at least one side-product in the final reaction mixture, to determine an amount of a compound selected from the group consisting of the X—OH, water, and the alcohol having the chemical structure $R^1$—OH or $R^2$—OH, to add in a third serial addition. The third addition steps, if performed, also include adding the third serial addition to the second reaction mixture, including a compound selected from the group consisting of the X—OH, water, and the alcohol having the chemical structure $R^1$—OH or $R^2$—OH, to provide the final reaction mixture. In this paragraph, $R^1$ and $R^2$ are the same or different, substituted or unsubstituted, monovalent aryl groups; and each of $R^3$, $R^4$, $R^5$, $R^6$ is independently selected from the group consisting of hydrogen and $C_{1-10}$ alkyl.

Various embodiments of the present invention provide a method for producing a diphosphite ligand structure (DLS) having the following structure,

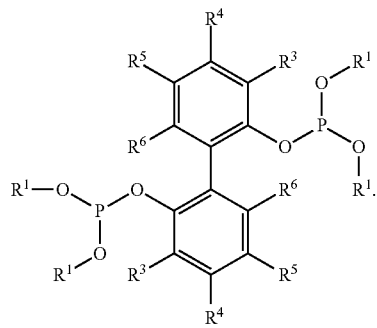

The method includes contacting a phosphorochloridite having the following structure,

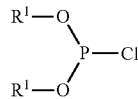

with a bisaryl compound having the following structure,

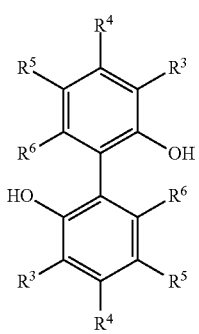

and a tertiary organic amine to provide a final reaction mixture including the diphosphite. The contacting includes providing a pre-determined limit for the mole percent of phosphorus present as T-phite ligand structure (TLS), having the chemical structure shown below, in the final reaction mixture

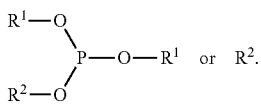

The contacting also includes providing a pre-determined limit for the mole percent of phosphorus present as C-phite ligand structure (CLS), having the chemical structure shown below, in the final reaction mixture

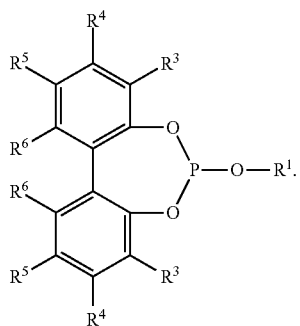

The contacting also includes providing a pre-determined limit for the mole percent of phosphorus present as a ligand hydrolysis product (LHP) in the final reaction mixture. LHP includes at least one product derived by a process including hydrolysis of the DLS or of the phosphorochloridite; hydrolysis of a product derived from the DLS or from the phosphorochloridite; or reaction of the hydrolysis product of the DLS or of the phosphorochloridite, or reaction of the hydrolysis product of a product derived from the DLS or from the phosphorochloridite. The contacting also includes providing a pre-determined goal for a conversion of phosphorochloridite in the first reaction mixture. The contacting also includes adding the bisaryl compound to the phosphorochloridite in a first serial addition to provide a first reaction mixture, wherein the amount of bisaryl compound added is sufficient to cause the percent conversion of the phosphorochloridite in the first reaction mixture to be equal to or greater than the pre-determined goal for a conversion of the phosphorochloridite in the first reaction mixture. The contacting also includes determining the mole percent of phosphorus present in the first reaction mixture as TLS. The contacting also includes determining the mole percent of phosphorus present in the first reaction mixture as CLS. The contacting also includes determining the percent conversion of the phosphorochloridite in the first reaction mixture. If in the first reaction mixture both the mole percents of phosphorus present as the CLS and the TLS are equal to or greater than the respective pre-determined limits for the mole percents of phosphorus present as the CLS or the TLS in the final reaction mixture, then the second serial addition includes water. If in the first reaction mixture the mole percent of phosphorus present as the CLS is equal to or above the pre-determined limit for the mole percent of phosphorus present as the CLS in the final reaction mixture, and in the first reaction mixture the mole percent of phosphorus present as the TLS is not equal to or above the pre-determined limit for the mole percent of phosphorus present as the TLS in the final reaction mixture, and in the first reaction mixture the mole percent of phosphorus present as LHP is equal or to greater than the pre-determined limit for the mole percent of phosphorus present as LHP in the final reaction mixture, then the second serial addition includes the alcohol having the chemical structure $R^1$—OH or $R^2$—OH. If in the first reaction mixture neither the mole percent of phosphorus present as the CLS nor the TLS is equal to or above the respective pre-determined limits for the mole percents of phosphorus present as the CLS or the TLS in the final reaction mixture, and the conversion of phosphorochloridite in the first reaction product is less than the pre-determined goal for the conversion of phosphorochloridite in the second reaction mixture, then second serial addition includes the bisaryl compound, wherein the quantity of the bisaryl compound to add in the second serial addition is determined using a comparison of the percent conversion of the phosphorochloridite in the first reaction mixture to the pre-determined goal for the conversion of phosphorochloridite in the second reaction mixture to determine the amount of the bisaryl compound to add in the second serial addition. Using the comparison to determine the amount of bisaryl compound to add in the second serial addition includes using at least one selectivity ratio of the phosphorochloridite to the phosphorus-containing ligand and CLS at a given conversion range in combination with the determined mole percents of TLS and CLS in the first reaction mixture to forecast a maximum percent conversion of phosphorochloridite such that at the forecasted percent conversion in the second reaction mixture the percent of phosphorus present as CLS in the second reaction mixture is less than the pre-determined limit for the percent of phosphorus present as CLS in the final reaction mixture. Using the comparison to determine the amount of bisaryl compound to add in the second serial addition also includes setting a pre-determined goal for the conversion of phosphorochloridite in the second reaction mixture to the forecasted maximum percent conversion of the phosphorochloridite. The contacting also includes adding the second serial addition to the first reaction mixture, including a compound selected from the group consisting of the bisaryl compound, water, and the alcohol having the chemical structure $R^1$—OH or $R^2$—OH, to provide the second reaction mixture, wherein if bisaryl compound is added in the second serial addition then the amount of the bisaryl compound in the second serial addition is sufficient to cause the percent conversion of the phosphorochloridite in the second reaction mixture to be about equal to the pre-determined goal for the conversion of the phosphorochloridite in the second reaction mixture. The contacting also includes either performing third addition steps, or the final reaction mixture is the second reaction mixture. If the final reaction mixture is the second reaction mixture, the quantities of the one of more compound added in the second addition are such that conversion of the phosphorochloridite in the final reaction mixture is about 100%. Third addition steps, if performed, include optionally determining a mole percent of phosphorus present in the second reaction mixture as at least one side-product. Third addition steps, if performed, include optionally using a comparison of the mole percent of phosphorus present in the second reaction mixture as the at least one side-product to a pre-determined limit for the mole percent of phosphorus present as the at least one side-product in the final reaction mixture, to determine an amount of a compound selected from the group consisting of water and the alcohol having the chemical structure $R^1$—OH or $R^2$—OH, to add in a third serial addition. Third addition steps, if performed, also include adding the third serial addition to the second reaction mixture to provide the final reaction mixture, wherein the quantities of the one or more compounds added in the third addition are such that the conversion of the phosphorochloridite in the final reaction mixture is about 100%. In this paragraph, $R^1$ and $R^2$ are the same or different, substituted or unsubstituted, monovalent aryl groups; and each of $R^3$, $R^4$, $R^5$, $R^6$ is independently selected from the group consisting of hydrogen and $C_{1-10}$ alkyl.

The present invention provides certain advantages over other methods of producing a phosphorus-containing ligand, including a diphosphite-containing ligand structure (DLS). In some embodiments, the phosphorus-containing ligand or DLS is generated at higher yield than other methods. In various embodiments, the phosphorus-containing ligand is generated with smaller amounts of impurities than other methods, for example the DLS can be generated with smaller amounts of TLS or CLS than other methods. In some embodiments, in the final product mixture the phosphorus-containing ligand can be generated with smaller amounts of hydrolysis products than other methods. For example, in the final product mixture the DLS can be generated with smaller amounts of ligand hydrolysis products (LHPs) than other methods. In some embodiments, the phosphorus-containing ligand can be generated with a more highly controlled amount of impurities and hydrolysis products than other methods. For example, the DLS can be generated with a more highly controlled amount of TLS, CLS, or LHPs than other methods. In some embodiments, in the final product mixture impurities or hydrolysis products are present within specified limits for maximum concentration while the yield of the phosphorus-containing ligand is higher than that of other methods that can keep impurities or hydrolysis products within similar limits. For example, in the final product mixture TLS, CLS, and LHPs can be present within specified limits for maximum concentration while the yield of the DLS can be higher than that of other methods that can keep TLS, CLS and LHP concentrations within similar limits. In some embodiments, the final product mixture containing the phosphorus-containing ligand has low enough concentrations of impurities or hydrolysis products that the final product mixture can be used to generate a complex that can function more efficiently as a catalyst than the catalyst formed from the final product mixture of other phosphorus-containing ligand synthesis methods. For example, the final product mixture containing the DLS can have low enough concentrations of TLS, CLS, or LHPs that the final product mixture can be used to generate a nickel(0)-DLS complex that can function more efficiently as a hydrocyanation catalyst than the nickel(0)-DLS complex formed from the final product mixture of other DLS synthesis methods. In some embodiments, the final product mixture can have low enough concentrations of impurities or hydrolysis products that it can be used to generate a catalyst that can efficiently catalyze a particular reaction, while the overall yield of the phosphorus-containing ligand can be higher than that of other methods used to make final reaction mixtures that include the phosphorus-containing ligand and that can generate a catalyst as efficient for catalyzing the particular reaction. For example, the final product mixture can have low enough concentrations of TLS, CLS, or LHPs that it can be used to generate a nickel(0)-DLS complex that can function efficiently as a hydrocyanation catalyst, while the overall yield of DLS can be higher than that of other methods used to make DLS-containing final product mixtures that can form nickel(0)-DLS complexes efficient for catalyzing hydrocyanation reactions. In various embodiments, the method can be consistently repeated to produce final reaction mixtures with impurity levels within specification limits. In some examples, the method can be consistently repeated to produce final reaction mixtures with highly consistent impurity levels and yields of the phosphorus-containing ligand. In some examples, the method can be consistently repeated to produce final reaction mixtures with highly consistent levels of the CLS side-product, within specification limits. In some embodiments, the phosphorus-containing ligand or a catalyst complex made from the ligand can be efficiently recycled after use in a hydrocyanation reaction while maintaining a higher catalytic efficiency than phosphorus-containing ligands or complexes made therefrom made by other methods. Various embodiments of the present invention satisfy a need for a simple and selective process for preparing a phosphorus-containing ligand, including a DLS, to meet predetermined purity specifications, including for use as components of hydrocyanation catalysts. While obtaining high selectivities for formation of phosphorus-containing ligands such as DLS, some embodiments of the present invention provide a method for overcoming temperature limitations of other methods, such as those identified in U.S. Pat. No. 6,069,267 and WO 2004/050588.

DETAILED DESCRIPTION OF THE INVENTION

Reference will now be made in detail to certain claims of the disclosed subject matter. While the disclosed subject matter will be described in conjunction with the enumerated claims, it will be understood that they are not intended to limit the disclosed subject matter to those claims. On the contrary, the disclosed subject matter is intended to cover all alternatives, modifications, and equivalents, which can be included within the scope of the presently disclosed subject matter as defined by the claims.

References in the specification to "one embodiment," "an embodiment," "an example embodiment," etc., indicate that the embodiment described can include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

In this document, the terms "a" or "an" are used to include one or more than one and the term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading can occur within or outside of that particular section. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

In the methods of manufacturing described herein, the steps can be carried out in any order without departing from the principles of the invention, except when a temporal or operational sequence is explicitly recited. Recitation in a claim to the effect that first a step is performed, then several other steps are subsequently performed, shall be taken to mean that the first step is performed before any of the other steps, but the other steps can be performed in any suitable sequence, unless a sequence is further recited within the other steps. For example, claim elements that recite "Step A, Step B, Step C, Step D, and Step E" shall be construed to mean step A is carried out first, step E is carried out last, and steps B, C, and D can be carried out in any sequence between steps A and E, and that the sequence still falls within the literal scope of the claimed process. A given step or sub-set of steps can also be repeated, or carried out simultaneously with other steps. In another example, claim elements that recite "Step A, Step B, Step C, Step D, and Step E" can be construed to mean Step A is carried out first, Step B is carried out next, Step C is carried out next, Step D is carried out next, and Step E is carried out last.

Furthermore, specified steps can be carried out concurrently unless explicit claim language recites that they be carried out separately. For example, a claimed step of doing X and a claimed step of doing Y can be conducted simultaneously within a single operation, and the resulting process will fall within the literal scope of the claimed process.

DEFINITIONS

The singular forms "a," "an" and "the" can include plural referents unless the context clearly dictates otherwise.

The term "about" can allow for a degree of variability in a value or range, for example, within 10%, within 5%, or within 1% of a stated value or of a stated limit of a range. When a range or a list of sequential values is given, unless otherwise specified any value within the range or any value between the given sequential values is also disclosed.

The term "organic group" as used herein refers to but is not limited to any carbon-containing functional group. For example, an oxygen-containing group such as alkoxy groups, aryloxy groups, aralkyloxy groups, oxo(carbonyl) groups, carboxyl groups including carboxylic acids, carboxylates, and carboxylate esters; a sulfur-containing group such as alkyl and aryl sulfide groups; and other heteroatom-containing groups. Non-limiting examples of organic groups include OR', OC(O)N(R')$_2$, CN, CF$_3$, OCF$_3$, R', C(O), methylenedioxy, ethylenedioxy, N(R')$_2$, SR', SOR', SO$_2$R', SO$_2$N(R')$_2$, SO$_3$R', C(O)R', C(O)C(O)R', C(O)CH$_2$C(O)R', C(S)R', C(O)OR', OC(O)R', C(O)N(R')$_2$, OC(O)N(R')$_2$, C(S)N(R')$_2$, (CH$_2$)$_{0-2}$N(R')C(O)R', (CH$_2$)$_{0-2}$N(R')N(R')$_2$, N(R')N(R')C(O)R', N(R')N(R')C(O)OR', N(R')N(R')CON(R')$_2$, N(R')SO$_2$R', N(R')SO$_2$N(R')$_2$, N(R')C(O)OR', N(R')C(O)$_2$R', N(R')C(S)R', N(R')C(O)N(R')$_2$, N(R')C(S)N(R')$_2$, N(COR')COR', N(OR')R', C(=NH)N(R')$_2$, C(O)N(OR')R', or C(=NOR')R' wherein R' can be hydrogen (in examples that include other carbon atoms) or a carbon-based moiety, and wherein the carbon-based moiety can itself be further substituted; for example, wherein R' can be hydrogen (in examples that include other carbon atoms), alkyl, acyl, cycloalkyl, aryl, aralkyl, heterocyclyl, heteroaryl, or heteroarylalkyl, wherein any alkyl, acyl, cycloalkyl, aryl, aralkyl, heterocyclyl, heteroaryl, or heteroarylalkyl, or R' can be independently mono- or multi-substituted with J; or wherein two R' groups bonded to a nitrogen atom or to adjacent nitrogen atoms can together with the nitrogen atom or atoms form a heterocyclyl, which can be mono- or independently multi-substituted with J. Examples of organic groups include linear and/or branched groups such as alkyl groups, fully or partially halogen-substituted haloalkyl groups, alkenyl groups, alkynyl groups, aromatic groups, acrylate functional groups, and methacrylate functional groups; and other organic functional groups such as ether groups, cyanate ester groups, ester groups, carboxylate salt groups, and masked isocyano groups. Examples of organic groups include, but are not limited to, alkyl groups such as methyl, ethyl, propyl, isopropyl, n-butyl, s-butyl, and t-butyl groups, acrylate functional groups such as acryloyloxypropyl groups and methacryloyloxypropyl groups; alkenyl groups such as vinyl, allyl, and butenyl groups; alkynyl groups such as ethynyl and propynyl groups; aromatic groups such as phenyl, tolyl, and xylyl groups; cyanoalkyl groups such as cyanoethyl and cyanopropyl groups; halogenated hydrocarbon groups such as 3,3,3-trifluoropropyl, 3-chloropropyl, dichlorophenyl, and 6,6,6,5,5,4,4,3,3-nonafluorohexyl groups; alkenyloxypoly(oxyalkyene) groups such as allyloxy(polyoxyethylene), allyloxypoly(oxypropylene), and allyloxy-poly(oxypropylene)-co-poly(oxyethylene) groups; alkyloxypoly(oxyalkyene) groups such as propyloxy (polyoxyethylene), propyloxypoly(oxypropylene), and propyloxy-poly(oxypropylene) co-poly(oxyethylene) groups; halogen substituted alkyloxypoly(oxyalkyene) groups such as perfluoropropyloxy(polyoxyethylene), perfluoropropyloxypoly(oxypropylene), and perfluoropropyloxy-poly(oxypropylene)-co-poly(oxyethylene) groups; alkoxy groups such as methoxy, ethoxy, n-propoxy, isopropoxy, n-butoxy, and ethylhexyloxy groups; aminoalkyl groups such as 3-aminopropyl, 6-aminohexyl, 11-aminoundecyl, 3-(N-allylamino)propyl, N-(2-aminoethyl)-3-aminopropyl, N-(2-aminoethyl)-3-aminoisobutyl, p-aminophenyl, 2-ethylpyridine, and 3-propylpyrrole groups; epoxyalkyl groups such as 3-glycidoxypropyl, 2-(3,4,-epoxycyclohexyl)ethyl, and 5,6-epoxyhexyl groups; ester functional groups such as actetoxyethyl and benzoyloxypropyl groups; hydroxy functional groups such as 2-hydroxyethyl groups; masked isocyanate functional groups such as propyl-t-butylcarbamate, and propylethylcarbamate groups; aldehyde functional groups such as undecanal and butyraldehyde groups; anhydride functional groups such as 3-propyl succinic anhydride and 3-propyl maleic anhydride groups; and metal salts of carboxylic acids such as the zinc, sodium, or potassium salts of 3-carboxypropyl and 2-carboxyethyl.

The term "substituted" as used herein refers to an organic group as defined herein or molecule in which one or more bonds to a hydrogen atom contained therein are replaced by one or more bonds to a non-hydrogen atom. The term "functional group" or "substituent" as used herein refers to a group that can be or is substituted onto a molecule, or onto an organic group. Examples of substituents or functional groups include, but are not limited to, a halogen (e.g., F, Cl, Br, and I); an oxygen atom in groups such as hydroxyl groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxylamines, nitriles, nitro groups, N-oxides, hydrazides, azides, and enamines; and other heteroatoms in various other groups. Non-limiting examples of substituents J that can be bonded to a substituted carbon (or other) atom include F, Cl, Br, I, OR', OC(O)N(R')$_2$, CN, NO, NO$_2$, ONO$_2$, azido, CF$_3$, OCF$_3$, R', O (oxo), S (thiono), C(O), S(O), methylenedioxy, ethylenedioxy, N(R')$_2$, SR', SOR', SO$_2$R', SO$_2$N(R')$_2$, SO$_3$R', C(O)R', C(O)C(O)R', C(O)CH$_2$C(O)R', C(S)R', C(O)OR', OC(O)R', C(O)N(R')$_2$, OC(O)N(R')$_2$, C(S)N(R')$_2$, (CH$_2$)$_{0-2}$N(R$^1$)C(O)R', (CH$_2$)$_{0-2}$N(R')N(R')$_2$, N(R')N(R')C(O)R', N(R')N(R')C(O)OR', N(R')N(R')CON(R')$_2$, N(R')SO$_2$R', N(R')SO$_2$N(R')$_2$, N(R')C(O)OR', N(R')C(O)R', N(R')C(S)R', N(R')C(O)N(R')$_2$, N(R')C(S)N(R')$_2$, N(COR')COR', N(OR')R', C(=NH)N(R')$_2$, C(O)N(OR')R', or C(=NOR')R' wherein R' can be hydrogen or a carbon-based moiety, and wherein the carbon-based moiety can itself be further substituted; for example, wherein R' can be hydrogen, alkyl, acyl, cycloalkyl, aryl, aralkyl, heterocyclyl, heteroaryl, or heteroarylalkyl, wherein any alkyl, acyl, cycloalkyl, aryl, aralkyl, heterocyclyl, heteroaryl, or heteroarylalkyl or R' can be independently mono- or multi-substituted with J; or wherein two R' groups bonded to a nitrogen atom or to adjacent nitrogen atoms can together with the nitrogen atom or atoms form a heterocyclyl, which can be mono- or independently multi-substituted with J.

The term "alkyl" as used herein refers to straight chain and branched alkyl groups and cycloalkyl groups having from 1 to about 20 carbon atoms, and typically from 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed herein, for example, amino, hydroxy, cyano, carboxy, nitro, thio, alkoxy, and halogen groups.

The term "alkenyl" as used herein refers to straight and branched chain and cyclic alkyl groups as defined herein, except that at least one double bond exists between two carbon atoms. Thus, alkenyl groups have from 2 to about 20 carbon atoms, and typically from 2 to 12 carbons or, in some embodiments, from 2 to 8 carbon atoms. Examples include, but are not limited to vinyl, —CH═CH(CH$_3$), —CH═C(CH$_3$)$_2$, —C(CH$_3$)═CH$_2$, —C(CH$_3$)═CH(CH$_3$), —C(CH$_2$CH$_3$)═CH$_2$, cyclohexenyl, cyclopentenyl, cyclohexadienyl, butadienyl, pentadienyl, and hexadienyl among others.

The term "alkynyl" as used herein refers to straight and branched chain alkyl groups, except that at least one triple bond exists between two carbon atoms. Thus, alkynyl groups have from 2 to about 20 carbon atoms, and typically from 2 to 12 carbons or, in some embodiments, from 2 to 8 carbon atoms. Examples include, but are not limited to —C≡CH, —C≡C(CH$_3$), —C≡C(CH$_2$CH$_3$), —CH$_2$C≡CH, —CH$_2$C≡C(CH$_3$), and —CH$_2$C≡C(CH$_2$CH$_3$) among others.

The term "acyl" as used herein refers to a group containing a carbonyl moiety wherein the group is bonded via the carbonyl carbon atom. The carbonyl carbon atom is also bonded to another carbon atom, which can be part of an alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen, the group is a "formyl" group, an acyl group as the term is defined herein. An acyl group can include 0 to about 12-20 additional carbon atoms bonded to the carbonyl group. An acyl group can include double or triple bonds within the meaning herein. An acryloyl group is an example of an acyl group. An acyl group can also include heteroatoms within the meaning here. A nicotinoyl group (pyridyl-3-carbonyl) group is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "cycloalkyl" as used herein refers to cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined herein. Representative substituted cycloalkyl groups can be mono-substituted or substituted more than once, such as, but not limited to, 2,2-, 2,3-, 2,4- 2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups. The term "cycloalkenyl" alone or in combination denotes a cyclic alkenyl group.

The term "aryl" as used herein refers to cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined herein. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed herein The term "heteroaryl" as used herein refers to aromatic ring compounds containing 5 or more ring members, of which, one or more is a heteroatom such as, but not limited to, N, O, and S; for instance, heteroaryl rings can have 5 to about 8-12 ring members. A heteroaryl group is a variety of a heterocyclyl group that possesses an aromatic electronic structure. A heteroaryl group designated as a C$_2$-heteroaryl can be a 5-ring with two carbon atoms and three heteroatoms, a 6-ring with two carbon atoms and four heteroatoms and so forth. Likewise a C$_4$-heteroaryl can be a 5-ring with one heteroatom, a 6-ring with two heteroatoms, and so forth. The number of carbon atoms plus the number of heteroatoms sums up to equal the total number of ring atoms. Heteroaryl groups include, but are not limited to, groups such as pyrrolyl, pyrazolyl, triazolyl, tetrazolyl, oxazolyl, isoxazolyl, thiazolyl, pyridinyl, thiophenyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Heteroaryl groups can be unsubstituted, or can be substituted with groups as is discussed herein. Representative substituted heteroaryl groups can be substituted one or more times with groups such as those listed herein.

The term "alkoxy" as used herein refers to an oxygen atom connected to an alkyl group, including a cycloalkyl group, as are defined herein. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include one to about 12-20 carbon atoms bonded to the oxygen atom, and can further include double or triple bonds, and can also include heteroatoms. For example, an allyloxy group is an alkoxy group within the meaning herein. A methoxyethoxy group is also an alkoxy group within the meaning herein, as is a methylenedioxy group in a context where two adjacent atoms of a structures are substituted therewith.

The term "amine" as used herein refers to primary, secondary, and tertiary amines having, e.g., the formula $N(group)_3$ wherein each group can independently be H or non-H, such as alkyl, aryl, and the like. Amines include but are not limited to $R-NH_2$, for example, alkylamines, arylamines, alkylarylamines; $R_2NH$ wherein each R is independently selected, such as dialkylamines, diarylamines, aralkylamines, heterocyclylamines and the like; and $R_3N$ wherein each R is independently selected, such as trialkylamines, dialkylarylamines, alkyldiarylamines, triarylamines, and the like. The term "amine" also includes ammonium ions as used herein.

The term "amino group" as used herein refers to a substituent of the form $-NH_2$, $-NHR$, $-NR_2$, $-NR_3^+$, wherein each R is independently selected, and protonated forms of each, except for $-NR_3^+$, which cannot be protonated. Accordingly, any compound substituted with an amino group can be viewed as an amine. An "amino group" within the meaning herein can be a primary, secondary, tertiary or quaternary amino group. An "alkylamino" group includes a monoalkylamino, dialkylamino, and trialkylamino group.

The terms "halo" or "halogen" or "halide", as used herein, by themselves or as part of another substituent mean, unless otherwise stated, a fluorine, chlorine, bromine, or iodine atom, preferably, fluorine, chlorine, or bromine.

The term "haloalkyl" group, as used herein, includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, and the like.

The term "monovalent" as used herein refers to a substituent connecting via a single bond to a substituted molecule. When a substituent is monovalent, such as, for example, F or Cl, it is bonded to the atom it is substituting by a single bond.

The term "hydrocarbon" as used herein refers to a functional group or molecule that includes carbon and hydrogen atoms. The term can also refer to a functional group or molecule that normally includes both carbon and hydrogen atoms but wherein all the hydrogen atoms are substituted with other functional groups.

The term "solvent" as used herein refers to a liquid that can dissolve a solid, liquid, or gas. Nonlimiting examples of solvents are organic compounds, water, alcohols, ionic liquids, and supercritical fluids.

The term "independently selected from" as used herein refers to referenced groups being the same, different, or a mixture thereof, unless the context clearly indicates otherwise. Thus, under this definition, the phrase "$X^1$, $X^2$, and $X^3$ are independently selected from noble gases" would include the scenario where, for example, $X^1$, $X^2$, and $X^3$ are all the same, where $X^1$, $X^2$, and $X^3$ are all different, where $X^1$ and $X^2$ are the same but $X^3$ is different, and other analogous permutations.

The term "ligand" as used herein refers to an ion or molecule that can bind to a central metal atom (e.g. Ni(0)) to form a coordination complex (e.g. a complex between Ni(0) and DLS).

The phrase "stage of the contacting" for the chemical reaction of the present method has its usual meaning wherein an initial stage of the contacting is when all three reactants, phosphorochloridite, bisaryl compound, and tertiary organic amine, first come into contact and a final stage is when the reaction is terminated, for example when water is added to the reaction mixture to separate a tertiary organic amine hydrogen chloride salt from the diphosphite.

General

Various methods of the present invention provide a method for producing a phosphorus-containing ligand structure having the following chemical structure

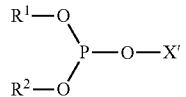

Structure I'

The method can include contacting a phosphorochloridite of the following structure,

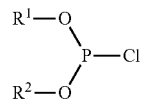

Structure II with a compound having the chemical structure X—OH and a tertiary organic amine to provide a final reaction mixture including the ligand structure. The contacting includes providing a pre-determined limit for a mole percent of phosphorus present as at least one side-product in the final reaction mixture. The contacting can include adding the X—OH to the phosphorochloridite in a first serial addition, to provide a first reaction mixture. The contacting can include adding a second serial addition to the first reaction mixture, including a compound selected from the group consisting of the X—OH, water, or the alcohol having the chemical structure $R^1$—OH or $R^2$—OH, to provide a second reaction mixture. The contacting can either includes adding a third addition or the second reaction mixture is the final reaction mixture. The third addition, if performed, can include adding a compound selected from the group consisting of the X—OH, water, and the alcohol having the chemical structure $R^1$—OH or $R^2$—OH, to provide the final reaction mixture. In the final reaction mixture, the percentage of phosphorus present as the at least one side-product can be at or below the pre-determined limit for the mole percent of phosphorus present as at least one side-product in the final reaction mixture. In this paragraph, $R^1$ and $R^2$ are the same or different, substituted or unsubstituted, monovalent aryl groups; $R^1$ and $R^2$ are bridged to one another or unbridged to one another; and each of X, X', $R^3$, $R^4$, $R^5$, $R^6$, $R^7$, $R^8$, $R^9$, $R^{10}$, $R^{11}$, and $R^{12}$ is independently selected from the group consisting of hydrogen, alkyl, aryl, heteroaryl, aryloxy, heteroaryloxy, alkyloxy, alkoxyalkyl, acetal, carboaryloxy, carboalkoxy, arylcarbonyl, alkylcarbonyl, phosphitylbisaryl, phosphitylbisheteroaryl, hydroxybisaryl, hydroxybisheteroaryl, oxazole, amine, amide, nitrile, mercaptyl, and halogen groups. In embodiments where X=phosphitylbisaryl, in some examples X can have a chemical structure selected from one of the following structures:

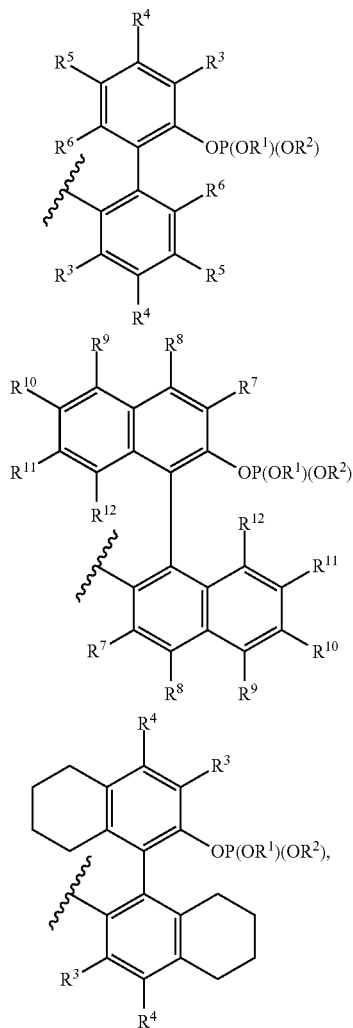

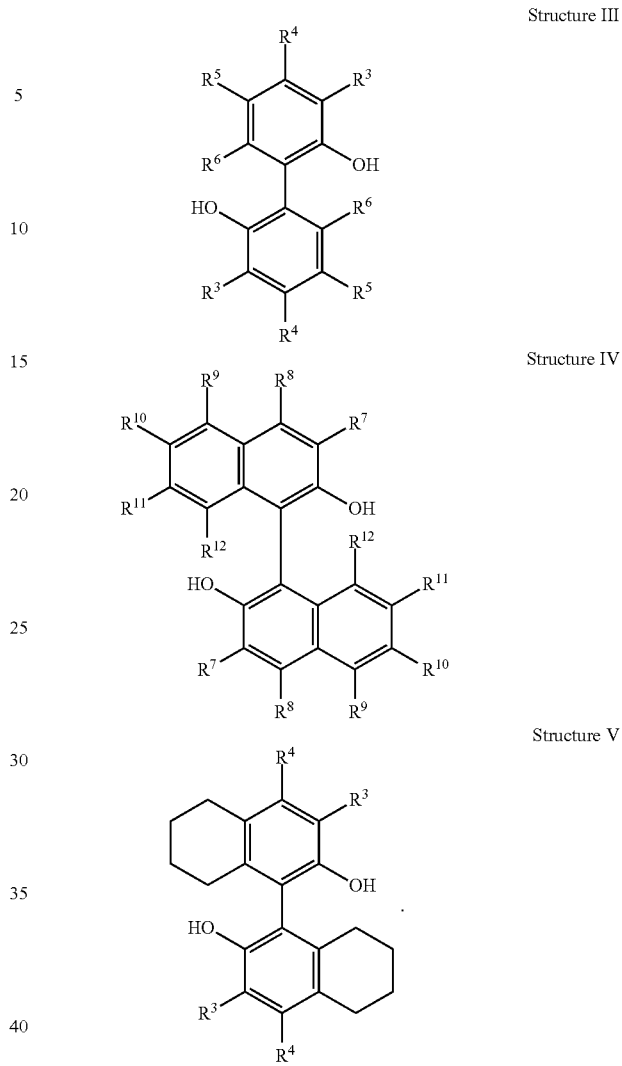

Structure III

Structure IV

Structure V wherein $R^1$ and $R^2$ are the same or different, substituted or unsubstituted, monovalent aryl groups; $R^1$ and $R^2$ are bridged to one another or unbridged to one another; and each of $R^3$, $R^4$, $R^5$, $R^6$, $R^7$, $R^8$, $R^9$, $R^{10}$, $R^{11}$, and $R^{12}$ is independently selected from the group consisting of hydrogen, alkyl, aryl, heteroaryl, aryloxy, heteroaryloxy, alkyloxy, alkoxyalkyl, acetal, carboaryloxy, carboalkoxy, arylcarbonyl, alkylcarbonyl, oxazole, amine, amide, nitrile, mercaptyl, and halogen groups.

In various embodiments, the present invention provides a method of making a phosphorus-containing ligand, wherein the ligand structure of Structure I' can be a diphosphite ligand structure (DLS) having the chemical structure of Structure I, Structure I

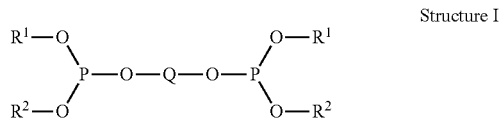

wherein the X—OH can be a bisaryl compound selected from the group consisting of Structure III, Structure IV, and Structure V, In the Structures given in this paragraph, $R^1$ and $R^2$ are the same or different, substituted or unsubstituted, monovalent aryl groups; each of $R^3$, $R^4$, $R^5$, $R^6$, $R^7$, $R^8$, $R^9$, $R^{10}$, $R^{11}$, and $R^{12}$ is independently selected from the group consisting of hydrogen, alkyl, aryl, heteroaryl, aryloxy, heteroaryloxy, alkyloxy, alkoxyalkyl, acetal, carboaryloxy, carboalkoxy, arylcarbonyl, alkylcarbonyl, oxazole, amine, amide, nitrile, mercaptyl, and halogen groups; and O-Q-O is a divalent species of the bisaryl compound.

In the structures given herein, unless otherwise specified, X and $R^1$-$R^{12}$ are independently selected from any suitable functional group. Herein several examples are given that involve the specific embodiment of the present invention wherein a DLS is produced. However, it is to be understood that a method for DLS production is a specific embodiment of the method of the present invention, and it is not to be limited as such; rather, the present invention generally provides a method of making phosphorus-containing ligands.

Numerous specific examples of the method are given herein, including wherein DLS is the phosphorus-containing ligand. These examples are not intended to limit the present invention in any way; the present invention includes a method for preparation of any suitable phosphorus-containing ligand as described herein.

General Reaction, C-Phite Ligand Structures (CLS), T-Phite Ligand Structures (TLS), Ligand Hydrolysis Products (LHPs)

Scheme I illustrates a generalized reaction scheme for the specific embodiment of the method wherein the generated phosphorus-containing ligand is a DLS. One of skill in the art will readily recognize the specific embodiment shown in Scheme I as employing the compound having the structure X—OH with X=-Q-OH, and will readily be able to extrapolate a general reaction scheme using X—OH in place of HO-Q-OH from the specific reaction scheme shown. Scheme I shows a monophosphite intermediate of Structure X and monodentate triorganophosphite co-products, both cyclic and acyclic, of C-phite ligand structures (CLS) having Structures VI, VII, and VIII, and also of T-phite ligand structures (TLS) having Structure IX, respectively. $R^1$ and $R^2$ can be the same or different, substituted or unsubstituted, monovalent aryl groups. For example, $R^1$ and $R^2$ can be substituted or unsubstituted phenyl, naphthyl, anthracenyl, and phenanthrenyl groups.

Scheme I

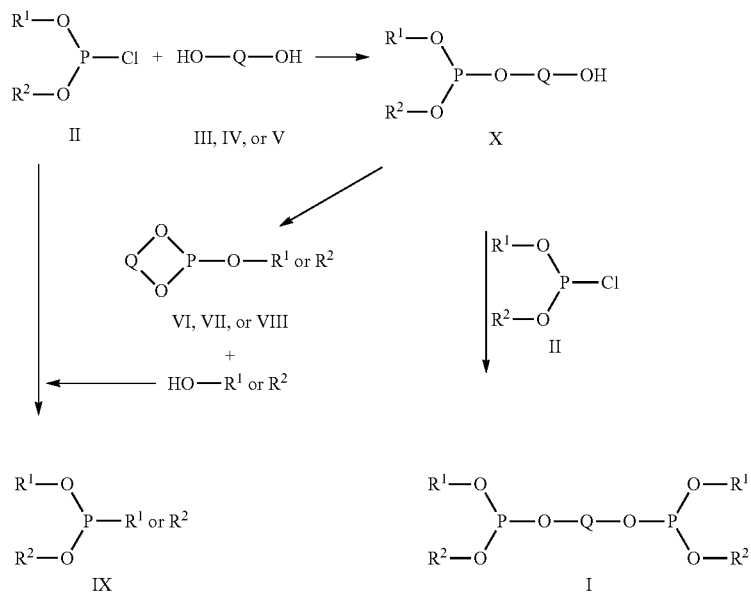

The bisaryl compound HO-Q-OH can have the following structures,

Structure III

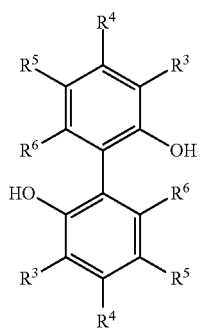

Structure IV

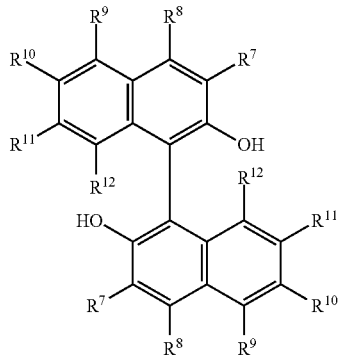

Structure V

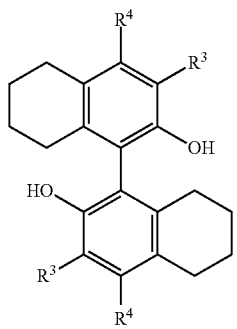

wherein each of $R^3$, $R^4$, $R^5$, $R^6$, $R^7$, $R^8$, $R^9$, $R^{10}$, $R^{11}$, and $R^{12}$ can be any suitable functional group. In one example, $R^3$, $R^4$, $R^5$, $R^6$, $R^7$, $R^8$, $R^9$, $R^{10}$, $R^{11}$, and $R^{12}$ are independently selected from the group consisting of hydrogen, alkyl, aryl, heteroaryl, aryloxy, heteroaryloxy, alkyloxy, alkoxyalkyl, acetal, carboaryloxy, carboalkoxy, arylcarbonyl, alkylcarbonyl, oxazole, amine, amide, nitrile, mercaptyl, and halogen groups; and O-Q-O is a divalent species of the bisaryl compound. In one example, $R^3$ to $R^{12}$ can be linear, branched, and cyclic $C_1$ to $C_{18}$ alkyl; substituted or unsubstituted $C_6$ to $C_{18}$ aryl; substituted or unsubstituted $C_6$ to $C_{18}$ aryloxy; linear, branched, and cyclic $C_1$ to $C_{18}$ alkyloxy; linear and branched $C_2$ to $C_{18}$ alkoxyalkyl; substituted or unsubstituted $C_3$ to $C_{18}$ cyclic acetals; substituted or unsubstituted $C_7$ to $C_{18}$ carboaryloxy; linear, branched, and cyclic $C_2$ to $C_{18}$ carboalkoxy; substituted or unsubstituted $C_7$ to $C_{18}$ arylcarbonyl; and substituted or unsubstituted $C_2$ to $C_{18}$ alkylcarbonyl.

In the first step of the generalized reaction scheme shown in Scheme I, the phosphorochloridite (Structure II) reacts with a bisaryl compound HO-Q-OH (having Structure III, IV, or V) to give a monophosphite intermediate (Structure X). A suitable tertiary organic amine, including a basic nitrogen atom or a plurality of nitrogen atoms, such as a triorganoamine or a tertiary aromatic amine, can be present to neutralize the acid (HCl) formed from the reaction of the phosphorochloridite with the bisaryl compound. The monophosphite intermediate (Structure X) can then either react intermolecularly with phosphorochloridite to give the desired DLS (Structure I), or it can react intramolecularly to produce the cyclic triorganophosphite co-product of Structures VI, VII, and VIII, which are referred to herein as C-phite ligand structure, or CLS.

The intramolecular reaction of the monophosphite intermediate (Structure X) produces one equivalent each of the cyclophosphite and aryl alcohol, $R^1$—OH or $R^2$—OH, that originates from the phosphorochloridite. In some examples, aryl alcohol $R^1$—OH or $R^2$—OH can also be produced by other routes, as described herein. Depending on the concentration of phosphorochloridite, the aryl alcohol can react with another equivalent of the phosphorochloridite to give the acyclic triorganophosphite co-product of Structure IX, which is referred to herein as T-phite ligand structure, or TLS. This intramolecular reaction of the monophosphite intermediate thus can cause both the bisaryl compound and the phosphorochloridite to be converted to undesired product, causing lower selectivity for DLS production as a result of TLS and CLS production. In some examples, a greater amount of steric bulk in the bisaryl compound, in the phosphorochloridite, or in both the bisaryl compound and the phosphorochloridite can result in a greater proportion of TLS and CLS production and lower selectivity for DLS production.

Phosphorochloridites can be synthesized by stepwise reaction of $PCl_3$ with aryl alcohols, $R^{10}H$ and $R^2OH$, in the presence of a suitable organic base to first prepare a phosphorodichloridite, for example $(R^1O)PCl_2$, followed by further reaction to prepare the phosphorochloridite, for example $(R^1O)(R^2O)PCl$, illustrated herein as Structure II. Syntheses for phosphorochloridites of Structure II are disclosed, for example, in PCT Publication WO 2004/050588.

Scheme II shows a generalized reaction scheme for hydrolysis of the phosphorochloridite. The phosphorochloridite can react with water to generate ligand hydrolysis products (LHPs), which can include acidic phosphorus-containing compounds (Structures XI and XII), phosphorous acid ($H_3PO_3$) or other phosphorus-containing acids, and aryl alcohol originating from the phosphorochloridite ($R^1OH$ or $R^2OH$). The phosphorochloridite can also react with the initial hydrolysis product (Structure XI) to form a phosphorus-containing acid anhydride (Structure XI).

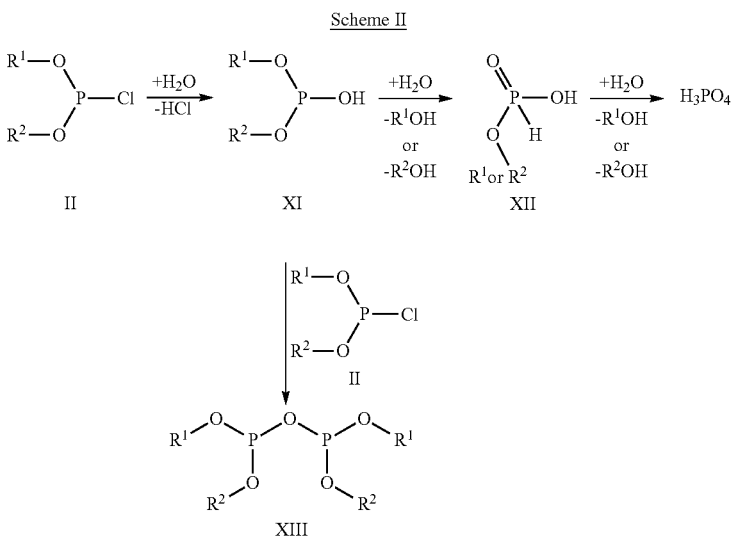

Empirically, as phosphorochloridite conversion increases, the intramolecular reaction rate for conversion of the monophosphite intermediate (Structure X) to CLS (Structures VI, VII, or VIII) and then to TLS (Structure IX) increases and selectivity to the desired DLS (Structure I) decreases. At high phosphorochloridite concentration, the rate for conversion of the monophosphite intermediate to DLS is increased compared to that in more dilute reaction conditions. Furthermore, dilute solutions can offer additional opportunity for reaction of the phosphorochloridite with any water contamination present to allow subsequent formation of acidic phosphorus-containing compounds, which can act as catalysts for the undesired intramolecular reaction to form CLS. Limiting the concentration of the monophosphite intermediate (Structure X) in the reaction mixture can help to achieve maximum selectivity for formation of DLS. Limiting the concentration of the monophosphite intermediate in the reaction mixture can limit the formation of undesired co-products such as TLS or CLS.

Contacting

Various embodiments of the present invention include contacting a phosphorochloridite of Structure II,

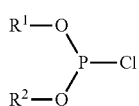

Structure II with an X—OH compound (e.g. a bisaryl compound) selected from the group consisting of Structure III, Structure IV, and Structure V,

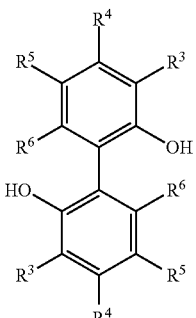

Structure III

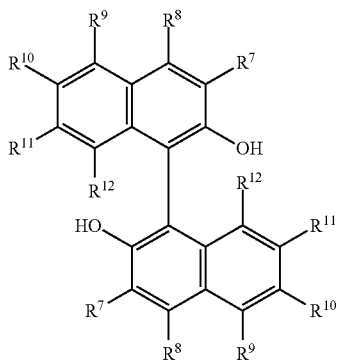

Structure IV

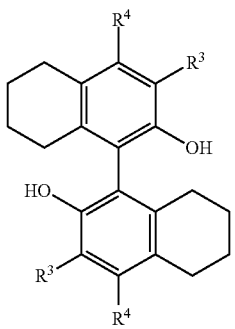

Structure V and a tertiary organic amine to provide a reaction mixture including a DLS of Structure I. The contacting includes adding the bisaryl compound to the phosphorochloridite in a first serial addition, to provide the first reaction mixture. The contacting also includes adding the second serial addition, including at least one of the bisaryl compound, water, or the alcohol having the chemical structure $R^1$—OH or $R^2$—OH, to provide the second reaction mixture. The contacting can either include adding a third addition or the second reaction mixture is the final reaction mixture. The third addition, if performed, can include adding a compound selected from the group consisting of the bisaryl compound, water, and the alcohol having the chemical structure $R^1$—OH or $R^2$—OH, to provide the final reaction mixture.

The contacting can be any suitable contacting. In one example, the contacting can include adding any suitable material or mixture of suitable materials to any other suitable material or mixture or suitable materials, and can occur in a continuous or a batch fashion. The addition of one or more compounds to one or more other compounds can take place over any suitable period of time; one of skill in the art will readily recognize the value of controlling addition rate in chemical reactions, particularly in large scale chemical reactions. In one example, contacting can include feeding the bisaryl compound to a mixture of phosphorochloridite and tertiary organic amine. In another example, contacting can include feeding the X—OH compound (e.g. the bisaryl compound) and the tertiary organic amine separately to the phosphorochloridite. In another example, contacting can include feeding the X—OH compound (e.g. the bisaryl compound) and the tertiary organic amine as a mixture to the phosphorochloridite. For example, contacting can include feeding the X—OH compound (e.g. the bisaryl compound) continuously or discontinuously to a stirred vessel including the phosphorochloridite and tertiary organic amine. In another example, contacting can include feeding the X—OH compound (e.g. the bisaryl compound) continuously or discontinuously to a tubular reactor including continuous flow of a mixture of the phosphorochloridite and tertiary organic amine.

As described further below, the first serial addition includes addition of the X—OH and other materials. For example, the first serial addition can include addition of bisaryl compound or a mixture of bisaryl compound and other materials. As described further below, the second or third serial addition can also include addition of bisaryl compound or a mixture of bisaryl compound and other materials. However, in some embodiments, the second or third serial addition does not include bisaryl compound.

In some embodiments, the contacting can occur in a well-mixed reaction zone. Suitable mixing methods include those appropriate to the size and shape of the reaction vessel. Non-limiting examples of mixing methods include suitable methods known to those skilled in the art such as mechanical stirrers, static mixers, nozzles, perforated pipes and downcomer trays. In some examples, liquids can be added using liquid distributors such as nozzles, perforated pipes, and downcomer trays. In some examples, flowing a liquid (e.g. bisaryl solution and tertiary organic amine) through at least one feed line that directs the liquid toward an impeller located below the upper liquid surface can help ensure efficient mixing of the liquid with the phosphorochloridite in a turbulent mixing zone of the reaction mixture. In some embodiments, poor mixing of the bisaryl compound or bisaryl solution with the phosphorochloridite can result in localized high concentrations of both bisaryl compound and monophosphite intermediate of Structure X, which can result in poorer selectivities for DLS formation.

In some examples, the method can produce phosphorus-containing ligand in the final reaction mixture with a molar selectivity from the phosphorochloridite compound such that the total molar percentage of phosphorus in the final reaction mixture as phosphorus-containing ligand (e.g. DLS) is between about 55% and about 65%, or between about 65% and about 75%, or between about 75% and about 85%, or between about 85% and about 90%, or between about 90% and about 95%, or between about 95% and about 100%.

In some embodiments, the method can include controlling the feeding such that a phosphorochloridite concentration is greater than or equal to an average distribution of about 0.02 moles per liter in the reaction mixture during the stage of the contacting, for example wherein phosphorochloridite conversion is from about 0% to about 90%. In some embodiments, the phosphorochloridite concentration is between an average distribution of about 0.02 and about 2.0 moles per liter in the reaction mixture during the stage of the contacting, for example wherein phosphorochloridite conversion is from about 0% to about 90%.

In various aspects, the method can include feeding the bisaryl compound to the phosphorochloridite at a feed rate between about 0.04 and about 10 molar equivalents per hour, relative to total moles of phosphorochloridite undergoing the contacting by the method. For example, feeding the bisaryl compound to the phosphorochloridite at a feed rate between about 0.5 and about 10 molar equivalents per hour.

In some examples, the first reaction mixture has a stoichiometric excess of phosphorochloridite. In some examples, the second reaction mixture has a stoichiometric excess of phosphorochloridite.

In some embodiments water can be detrimental to the selectivity of DLS formation. In some examples, water can be introduced to the reaction mixture via any feed stream, for example with the bisaryl compound, the tertiary organic amine, or a combination of the bisaryl compound and the tertiary organic amine. In examples, prior to the contacting with the phosphorochloridite, water can be at least partially separated from the bisaryl compound and the tertiary organic amine by phase separation, distillation, azeotropic distillation, contact with dried molecular sieves, drying columns, and other suitable methods known in the art.

In one embodiment of the present invention, the first serial addition can include the X—OH compound (e.g. the bisaryl compound) in sufficient quantity such that the conversion of the phosphorochloridite is about 85% to about 95% in the first reaction mixture; the second serial addition can include a smaller amount of the X—OH compound than the amount of the X—OH compound added in the first serial addition.

In another embodiment of the present invention, the first serial addition can include the X—OH compound in sufficient quantity such that the conversion of the phosphorochloridite is about 85% to about 91% in the first reaction mixture; the second serial addition can include an alcohol having the chemical structure $R^1$—OH or $R^2$—OH in sufficient quantity such that remaining phosphorochloridite is converted to a suitable side-product (e.g. the TLS) in the second (e.g. final) reaction mixture. In some examples, the second serial addition can include an alcohol having the chemical structure $R^1$—OH or $R^2$—OH in sufficient quantity such that in the second reaction mixture phosphorochloridite conversion is about 100%.

The first, second, and final reaction mixture can have a composition that evolves over time, as the reactants are gradually converted into products and an approximate equilibrium state is achieved in which the reaction products reach a relatively steady concentration, as will be readily understood by one of skill in the art. The amount of time to reach the approximately equilibrium state can be, for example, about 1 second to about 10 days, about 1 minute to about 5 days, or about 10 minutes to about 1 day, or about 1 hour to about 10 hours. In another example, the time to reach the approximately equilibrium state can be, for example, about 1 second to about 1 minute, or about 1 minute to about 1 hour, about 1 hour to about 5 hours, or about 5 hours to about 24 hours.

Generally, when the composition of the first, second, or final reaction mixture is referred to herein, unless otherwise indicated, reference is being made to the composition of the first reaction mixture after the particular addition step that gives rise to the reaction mixture has completed (e.g. the first addition, the second addition, or the third addition if performed), the reaction has essentially gone to completion, and an approximately equilibrium state has been achieved.

The contacting also includes determining a mole percent of phosphorus present in the first reaction mixture as at least one side-product. The contacting also includes using a comparison of the mole percent of phosphorus present in the first reaction mixture as the at least one side-product to a predetermined limit for the mole percent of phosphorus present as the at least one side-product in the final reaction mixture, to determine an amount of a compound selected from the group consisting of the X—OH, water, and an alcohol having the chemical structure $R^1$—OH or $R^2$—OH, to add in a second serial addition. The at least one side-product in such determination can be, for example, CLS, TLS, LHP, phosphorochloridite, any suitable side-product, or any combination thereof.

Hydrocarbon Solvent

In some embodiments, the reaction mixture can include at least one aromatic hydrocarbon solvent. The hydrocarbon solvent can include any suitable hydrocarbon solvent. The aromatic hydrocarbon solvent can be selected from the group consisting of $C_6$ to $C_{18}$ aromatic hydrocarbons. In some embodiments, the method can include feeding the X—OH compound to the phosphorochloridite as a solution of the X—OH compound including the X—OH compound and a hydrocarbon solvent. In some examples, the hydrocarbon solvent can be hydrocarbons selected from the group consisting of linear acyclic $C_5$ to $C_{18}$ aliphatic, branched acyclic $C_5$ to $C_{18}$ aliphatic, unsubstituted cyclic $C_5$ to $C_{18}$ aliphatic, substituted cyclic $C_5$ to $C_{18}$ aliphatic, unsubstituted $C_6$ to $C_{10}$ aromatic, and $C_6$ to $C_{18}$ substituted aromatic hydrocarbons. The hydrocarbon solvent can be selected from the group consisting of hydrocarbons whose boiling point is between 70° C. and 145° C. at atmospheric pressure. Examples of suitable aromatic hydrocarbon solvents include $C_{1-5}$-substituted benzenes, $C_{1-5}$-substituted phenol, and xylenes or xylenols of any suitable substitution pattern. Specific examples of suitable aromatic hydrocarbon solvents include toluene. In some examples, the X—OH compound is fed to the phosphorochloridite as a solution include the X—OH compound and hydrocarbon solvent.

Temperature of Contacting

The temperature of contacting can be any suitable temperature. In some embodiments, the contacting can occur at a temperature within a temperature range listed in the left-hand column of Table 1. In other embodiments, the contacting of the method can occur at a temperature within a temperature range listed in the right-hand column of Table 1. In other aspects of the invention, the reaction mixture includes a hydrocarbon solvent and the boiling point of the reaction mixture at one atmosphere (1 atm) in the right-hand column of Table 1 is approximately equal to the boiling point of the hydrocarbon solvent. In various embodiments, a hydrocarbon solvent can be introduced into the reaction mixture with the phosphorochloridite, the X—OH compound (e.g. the bisaryl compound), tertiary organic amine, with any combination of such members, or independent of these reactants.

TABLE 1

| Suitable Temperature Ranges for a Contacting Step, in Various Embodiments | |
|---|---|
| Temperature Range | Temperature Range |
| about 10 to about 110° C. | about 10° C. to the boiling point of the mixture at 1 atm |
| about 15 to about 110° C. | about 15° C. to the boiling point of the mixture at 1 atm |
| about 20 to about 110° C. | about 20° C. to the boiling point of the mixture at 1 atm |
| about 25 to about 110° C. | about 25° C. to the boiling point of the mixture at 1 atm |
| about 30 to about 110° C. | about 30° C. to the boiling point of the mixture at 1 atm |
| about 35 to about 110° C. | about 35° C. to the boiling point of the mixture at 1 atm |
| about 40 to about 110° C. | about 40° C. to the boiling point of the mixture at 1 atm |
| about 45 to about 110° C. | about 45° C. to the boiling point of the mixture at 1 atm |
| about 50 to about 110° C. | about 50° C. to the boiling point of the mixture at 1 atm |
| about 55 to about 110° C. | about 55° C. to the boiling point of the mixture at 1 atm |
| about 60 to about 110° C. | about 60° C. to the boiling point of the mixture at 1 atm |

Tertiary Organic Amine

The tertiary organic amine can be any suitable tertiary organic amine, and can be added in any suitable amount. In some embodiments, tertiary organic amine can be added in quantity sufficient to neutralize the HCl co-product in the reaction mixture. The amine can accelerate reaction rates and can limit acid-catalyzed chemistries that can reduce selectivities of DLS formation. In some examples, the method includes precipitating a tertiary organic amine hydrogen chloride salt from the reaction mixture during the contacting step. In some examples, both the selection of the tertiary organic amine and the contacting in the presence of a hydrocarbon solvent can precipitate a tertiary organic amine hydrogen chloride salt from the reaction mixture.

Examples of suitable tertiary organic amines including a single basic nitrogen atom can be a (R')(R")(R''')N compound wherein R', R", and R''' are independently selected from the group consisting of $C_1$ to $C_{10}$ alkyl and $C_6$ to $C_{10}$ aryl radicals, can be a tertiary aromatic amine compound, for example pyridine, or can be combinations of tertiary organic amines including a single basic nitrogen atom. One example of a suitable amine includes a trialkylamine with the alkyl group individually selected and having 1 to 10 carbon atoms, such as triethylamine. Other examples include tertiary organic amines including a plurality of basic nitrogen atoms have nitrogen atoms with no N—H bonds; for example N,N,N',N'-tetramethylethylenediamine. In some examples, the first addition, the second addition, the third addition (if performed), or any combination thereof can be carried out in the presence of a stoichiometric excess of the tertiary organic amine.

Weight Percent Ranges of Components

Other examples of molar ranges of various reactants are given herein, the ranges given in this section are non-limiting examples.

In some examples, the phosphorochloridite can be from about 10 wt % to about 90 wt %, about 20 wt % to about 80 wt %, or about 30 wt % to about 70 wt % of the total amount of phosphorochloridite, bisaryl compound, and tertiary organic amine added in all of the first, second, and third addition (if performed). In some embodiments, the phosphorochloridite can be from about 40 wt % to about 60 wt %, about 45 wt % to about 55 wt %, or about 48 wt % to about 52 wt % of the total amount of phosphorochloridite, bisaryl compound, and tertiary organic amine added.

In some examples, the bisaryl compound can from about 1 wt % to about 80 wt %, about 5 wt % to about 70 wt %, or about 10 wt % to about 60 wt % of the total amount of phosphorochloridite, bisaryl compound, and tertiary organic amine added in all of the first, second, and third addition (if performed). In some embodiments, the bisaryl compound can from about 10 wt % to about 45 wt %, about 20 wt % to about 35 wt %, or about 25 wt % to about 30 wt % of the total amount of phosphorochloridite, bisaryl compound, and tertiary organic amine added.

In some examples, the tertiary organic amine can be from about 1 wt % to about 99 wt %, about 5 wt % to about 70 wt %, or about 10 wt % to about 60 wt % of the total amount of phosphorochloridite, bisaryl compound, and tertiary organic amine added in all of the first, second, and third addition (if performed). In some embodiments, the tertiary organic amine can be from about 5 wt % to about 40 wt %, about 15 wt % to about 30 wt %, or about 20 wt % to about 25 wt % of the total amount of phosphorochloridite, bisaryl compound, and tertiary organic amine added.

In some examples, the aromatic hydrocarbon solvent can be present in from about 1 wt % to about 99.999 wt %, about 5 wt % to about 80 wt %, or about 10 wt % to about 60 wt % of the total amount of aromatic hydrocarbon solvent, phosphorochloridite, bisaryl compound, and tertiary organic amine added in all of the first, second, and third addition (if performed). In some embodiments, the aromatic hydrocarbon solvent can be present in from about 5 wt % to about 70 wt %, about 15 wt % to about 50 wt %, or about 25 wt % to about 40 wt % of the total amount of aromatic hydrocarbon solvent, phosphorochloridite, bisaryl compound, and tertiary organic amine added.

D-Phite Ligand Structure (DLS)

As described above, in a specific embodiment the method of the present invention can produce a diphosphite ligand structure (DLS) having the chemical structure of Structure I,

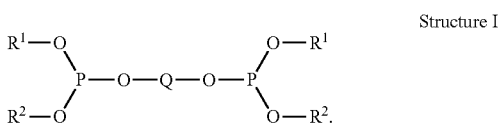

Structure I

In Structure I, $R^1$ and $R^2$ can be the same or different, substituted or unsubstituted, monovalent aryl groups. In some examples, $R^1$ and $R^2$ can be substituted or unsubstituted aryl groups. In some examples, $R^1$ and $R^2$ can be $C_{1-10}$ alkyl-substituted phenyl groups. In some examples, $R^1$ and $R^2$ can be the same. In some examples, $R^1$ and $R^2$ can be xylenyl groups (e.g. monovalent xylene groups), for example 2,4-xylenyl groups.

In Structure I, O-Q-O is a divalent species of the bisaryl compound having Structures III, N, and V. Thus, O-Q-O can be represented by one of the following three structures:

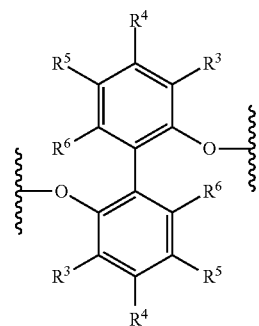

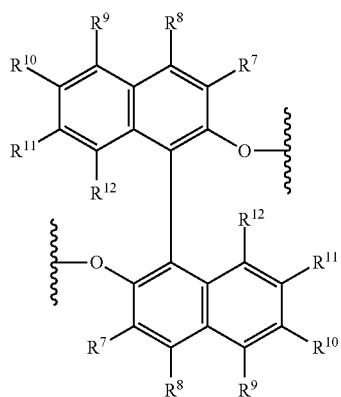

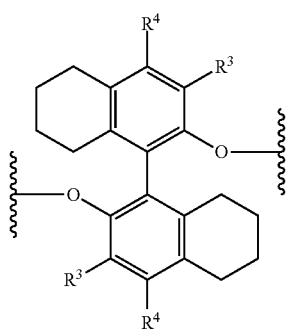

wherein each of $R^3$, $R^4$, $R^5$, $R^6$, $R^7$, $R^8$, $R^9$, $R^{10}$, $R^{11}$, and $R^{12}$ can be any suitable functional group. In one example, $R^3$, $R^4$, $R^5$, $R^6$, $R^7$, $R^8$, $R^9$, $R^{10}$, $R^{11}$ and $R^{12}$ are independently selected from the group consisting of hydrogen, alkyl, aryl, heteroaryl, aryloxy, heteroaryloxy, alkyloxy, alkoxyalkyl, acetal, carboaryloxy, carboalkoxy, arylcarbonyl, alkylcarbonyl, oxazole, amine, amide, nitrile, mercaptyl, and halogen groups. In one example, $R^3$ to $R^{12}$ can be linear, branched, and cyclic $C_1$ to $C_{18}$ alkyl; substituted or unsubstituted $C_6$ to $C_{18}$ aryl; substituted or unsubstituted $C_6$ to $C_{18}$ aryloxy; linear, branched, and cyclic $C_1$ to $C_{18}$ alkyloxy; linear and branched $C_2$ to $C_{18}$ alkoxyalkyl; substituted or unsubstituted $C_3$ to $C_{18}$ cyclic acetals; substituted or unsubstituted $C_2$ to $C_{18}$ carboaryloxy; linear, branched, and cyclic $C_2$ to $C_{18}$ carboalkoxy; substituted or unsubstituted to $C_{1-8}$ arylcarbonyl; and substituted or unsubstituted $C_2$ to $C_{18}$ alkylcarbonyl.

In some embodiments, DLS can be represented by the following structure:

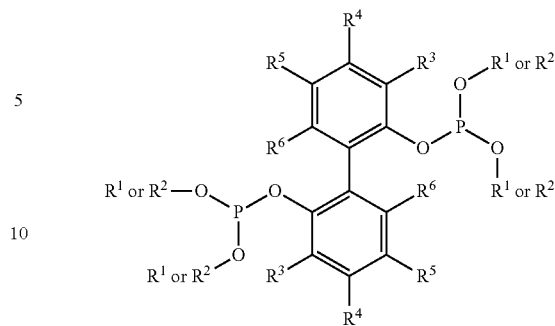

wherein W and $R^2$ are the same or different, substituted or unsubstituted, monovalent aryl groups; each of $R^3$, $R^4$, $R^5$, $R^6$ is independently selected from the group consisting of hydrogen and $C_{1-10}$ alkyl.

In some embodiments, DLS can be represented by the following structure:

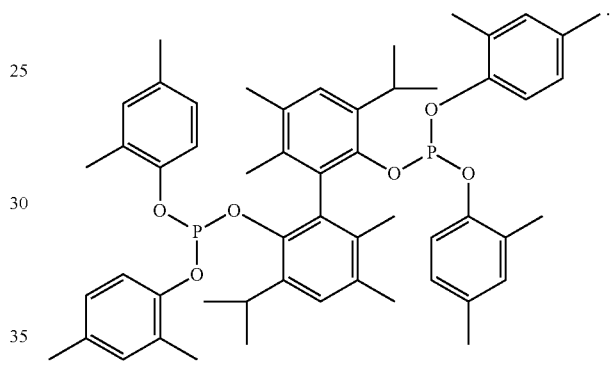

Thus, $R^1$ and $R^2$ can be 2,4-xylenyl, $R^3$ can be isopropyl, $R^4$ can be hydrogen, and $R^5$ and $R^6$ can be methyl. In some embodiments, DLS compounds such as the compound described in this paragraph can be identified in $^{31}P$ NMR spectra by peaks occurring at about 131.8 ppm.

In some embodiments, in the final reaction mixture, the percentage of phosphorus present as the phosphorus-containing ligand structure can be from about 1% to about 100% or about 30% to about 100%, or about 50% to about 99%, or about 55% to about 95%, or about 60% to about 90%, or about 60% to about 80%, or about 62% to about 85%, or about 64% to about 80%, or about 65%, or about 70%.

In some embodiments, in the final reaction mixture, the percentage of phosphorus present as the phosphorus-containing ligand structure is greater than or equal to about 65%, and the percentage of phosphorus present as the LHP is less than no more than about 5%. In some embodiments, in the final reaction mixture, the percentage of phosphorus present as the phosphorus-containing ligand structure is greater than or equal to about 70%, and the percentage of phosphorus present as the LHP is less than no more than about 3.5%. In some embodiments, in the final reaction mixture, the percentage of phosphorus present as the phosphorus-containing ligand structure is greater than or equal to about 65%, and the percentage of phosphorus present as the CLS is less than about 5%. In some embodiments, in the final reaction mixture, the percentage of phosphorus present as the phosphorus-containing ligand structure is greater than or equal to about 70%, and the percentage of phosphorus present as the CLS is less than about 3.5%.

T-Phite Ligand Structure (TLS) and C-Phite Ligand Structure (CLS)

As described above in Scheme I, in some embodiments, the method can produce at least one phosphorus-containing co-product in the final reaction mixture selected from the group consisting of $P(OR^1)(OR^2)_2$, $P(OR^1)_2(OR^2)$, $P(OR^1)_3$ (when $R^2=R^1$), $P(OR^2)_3$ (when $R^1=R^2$), TLS structures shown below as Structure IX:

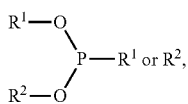

Structure IX and a compound of CLS Structures VI, VII, or VIII, shown below:

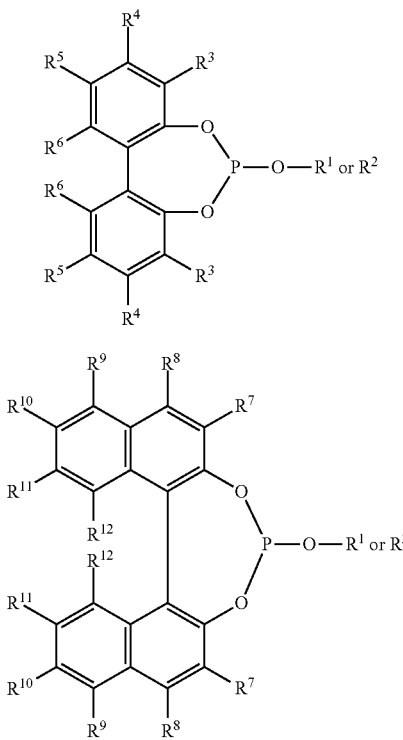

Structure VI

Structure VII

Structure VIII

In the TLS and CLS structures given above, $R^1$ and $R^2$ can be the same or different, substituted or unsubstituted, monovalent aryl groups. In some examples, $R^1$ and $R^2$ can be substituted or unsubstituted aryl groups. In some examples, $R^1$ and $R^2$ can be $C_{1-10}$ alkyl-substituted phenyl groups. In some examples, $R^1$ and $R^2$ can be the same. In some examples, $R^1$ and $R^2$ can be xylenyl groups (e.g. monovalent xylene groups), for example 2,4-xylenyl groups. Each of $R^3$, $R^4$, $R^5$, $R^6$, $R^7$, $R^8$, $R^9$, $R^{10}$, $R^{11}$, and $R^{12}$ can be any suitable functional group. In one example, $R^3$, $R^4$, $R^5$, $R^6$, $R^7$, $R^8$, $R^9$, $R^{10}$, $R^{11}$, and $R^{12}$ are independently selected from the group consisting of hydrogen, alkyl, aryl, heteroaryl, aryloxy, heteroaryloxy, alkyloxy, alkoxyalkyl, acetal, carboaryloxy, carboalkoxy, arylcarbonyl, alkylcarbonyl, oxazole, amine, amide, nitrile, mercaptyl, and halogen groups. In one example, $R^3$ to $R^{12}$ can be linear, branched, and cyclic $C_1$ to $C_{18}$ alkyl; substituted or unsubstituted $C_6$ to $C_{18}$ aryl; substituted or unsubstituted $C_6$ to $C_{18}$ aryloxy; linear, branched, and cyclic $C_1$ to $C_{18}$ alkyloxy; linear and branched $C_2$ to $C_{18}$ alkoxyalkyl; substituted or unsubstituted $C_3$ to $C_{18}$ cyclic acetals; substituted or unsubstituted $C_7$ to $C_{18}$ carboaryloxy; linear, branched, and cyclic $C_2$ to $C_{18}$ carboalkoxy; substituted or unsubstituted $C_7$ to $C_{18}$ arylcarbonyl; and substituted or unsubstituted $C_2$ to $C_{18}$ alkylcarbonyl.

In some embodiments, TLS can be represented by the following structure:

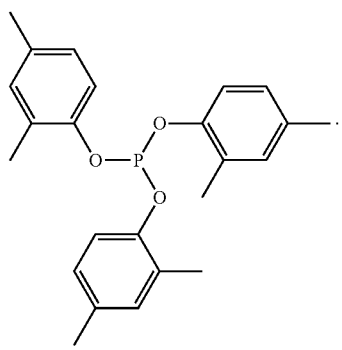 [SMILES: Cc1ccc(OP(Oc2ccc(C)cc2C)Oc2ccc(C)cc2C)c(C)c1 ; "."]

Thus, $R^1$ or $R^2$ can be 2,4-xylenyl. In some embodiments, TLS compounds, such as the compound described in this paragraph, can be identified in $^{31}P$ NMR spectra by peaks occurring at about 131.2 ppm.

In some embodiments, CLS can be represented by the following structure:

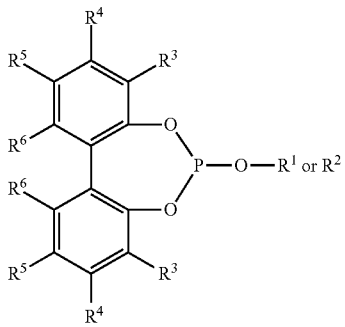

wherein $R^1$ and $R^2$ are the same or different, substituted or unsubstituted, monovalent aryl groups; each of $R^3$, $R^4$, $R^5$, $R^6$ is independently selected from the group consisting of hydrogen and $C_{1-10}$ alkyl.

In some embodiments, CLS can be represented by the following structure:

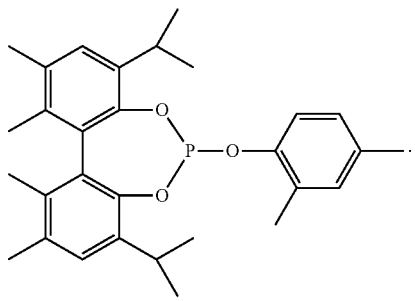

Thus, $R^1$ or $R^2$ can be 2,4-xylenyl, $R^3$ can be isopropyl, $R^4$ can be hydrogen, and $R^5$ and $R^6$ can be methyl. In some embodiments, CLS compounds such as the compound described in this paragraph can be identified in $^{31}P$ NMR spectra by peaks occurring at about 136.0 ppm.

Pre-Determined Limits

In various examples, the contacting includes providing pre-determined limits for the percent of phosphorus present as particular products in a reaction mixture, for example as particular side products in the final reaction mixture. The pre-determined limit can be any suitable pre-determined limit. The pre-determined limits can be provided at any suitable time, such as for example prior to the first addition, prior to the second addition, or prior to the third addition (if performed). In one example, the percent of phosphorus present as particular products in a reaction mixture is a molar percent. In another example, the percent of phosphorus present as particular products in a reaction mixture can be based on mass or based on any other suitable measure. The pre-determined limit can be based on all phosphorus-containing compounds in the reaction mixture. In one example, the pre-determined limit can be the desired specification limit for the percent of phosphorus present as the particular product in the final reaction mixture. In another example, the pre-determined limit can be some value below the desired specification limit for the percent of phosphorus present as the particular product in the final reaction mixture. By choosing a pre-determined limit lower than the specification limit, this can help to ensure that the actual specification limit is achieved in the final product mixture, and can allow for a margin of error. However, in some embodiments, no margin of error is used, and the pre-determined limit corresponds to the desired specification limit for the percent of phosphorus present as the particular product in the final reaction mixture.

In some examples, the contacting includes providing a pre-determined limit for the mole percent of phosphorus present as CLS in the final reaction mixture. The pre-determined limit for the mole percent of phosphorus present as CLS in the final reaction mixture can be any suitable pre-determined limit. In one example, the pre-determined limit for the mole percent of phosphorus present as CLS in the final reaction mixture is about 0 mol % to about 99 mol %, about 0 mol % to about 50 mol %, or about 0 mol % to about 5 mol %. In another example, the pre-determined limit for the mole percent of phosphorus present as CLS in the final reaction mixture is about 0 mol % to about 16 mol %, about 1 mol % to about 8 mol %, or about 2 mol % to about 4 mol %. In another example, the pre-determined limit for the mole percent of phosphorus present as CLS in the final reaction mixture is about 0 mol % to about 6 mol %, about 0 mol % to about 4 mol %, or about 0 mol % to about 2 mol %. Any pre-determined limit given in this paragraph can also be an example of the percentage of phosphorus present as the CLS in the final reaction mixture.

In some examples, the contacting includes providing a pre-determined limit for the mole percent of phosphorus present as TLS in the final reaction mixture. The pre-determined limit for the mole percent of phosphorus present as TLS in the final reaction mixture can be any suitable pre-determined limit. In one example, the pre-determined limit for the mole percent of phosphorus present as TLS in the final reaction mixture is about 0 mol % to about 100 mol %, or about 0 mol % to about 50 mol %. In another example, the pre-determined limit for the mole percent of phosphorus present as TLS in the final reaction mixture is about 2 mol % to about 50 mol %, about 5 mol % to about 40 mol %, or about 10 mol % to about 30 mol %. In another example, the pre-determined limit for the mole percent of phosphorus present as TLS in the final reaction mixture is about 3 mol % to about 80 mol %, about 7 mol % to about 40 mol %, or about 14 mol % to about 21 mol %. Any pre-determined limit given in this paragraph can also be an example of the percentage of phosphorus present as the TLS in the final reaction mixture.

In one example, the pre-determined limit for the mole percent of phosphorus present as LHP in the final reaction mixture is about 0 mol % to about 99 mol %, about 0 mol % to about 50 mol %, or about 0 mol % to about 5 mol %. The pre-determined limit for the mole percent of phosphorus present as LHP in the final reaction mixture can be any suitable pre-determined limit. In another example, the pre-determined limit for the mole percent of phosphorus present as LHP in the final reaction mixture is about 0 mol % to about 16 mol %, about 1 mol % to about 8 mol %, or about 2 mol % to about 4 mol %. In another example, the pre-determined limit for the mole percent of phosphorus present as LHP in the final reaction mixture is about 0 mol % to about 6 mol %, about 0 mol % to about 4 mol %, or about 0 mol % to about 2 mol %. Any pre-determined limit given in this paragraph can also be an example of the percentage of phosphorus present as the LHP in the final reaction mixture.

Providing a pre-determined limit can include providing a pre-determined limit for the percent phosphorus in the final reaction mixture that is present as one or more of TLS, CLS, LHP, DLS, any other suitable side-product.

Percent Conversion

In some embodiments, decisions about the composition of the first serial addition can be made including using a pre-determined goal for conversion of the phosphorochloridite in the first reaction mixture. Thus, contacting can include providing a pre-determined goal for the conversion of the phosphorochloridite in the first reaction mixture. The pre-determined goal for the conversion of phosphorochloridite in the first reaction mixture can be provided before the first addition is added. Contacting can also include using the pre-determined goal for the conversion of phosphorochloridite in the first reaction mixture to determine the amount of bisaryl compound to add in the first serial addition. For example, the pre-determined goal for the conversion of phosphorochloridite in the first reaction mixture can be used to determine the amount of bisaryl compound to add in the first serial addition such that the percent conversion of the phosphorochloridite in the first reaction mixture is at or above the pre-determined goal.

The pre-determined goal for the conversion of phosphorochloridite in the first reaction mixture can be any suitable pre-determined goal. In some embodiments, the pre-determined goal for the conversion of phosphorochloridite in the first reaction mixture is about 30% to about 100%, or about 70% to about 100%, or about 80% to about 97%, or about 85% to about 95%, or about 88% to about 92%, or about 90%.

In some embodiments, decisions about the composition of the second serial addition can be made including using a pre-determined goal for conversion of phosphorochloridite in the second reaction mixture. Thus, contacting can include providing a pre-determined goal for the conversion of phosphorochloridite in the second reaction mixture. In some embodiments, the providing of the pre-determined goal for the conversion of phosphorochloridite in the second reaction mixture can occur before the first serial addition is added. In other embodiments, the pre-determined goal for the conversion of phosphorochloridite in the second reaction mixture can be provided after the first serial addition is added. Contacting can also include, after adding the first serial addition, determining the percent conversion of the phosphorochloridite in the first reaction mixture. Contacting can also include, before adding the second serial addition, using a comparison of the percent conversion of the phosphorochloridite in the first reaction mixture to the pre-determined goal for the conversion of phosphorochloridite in the second reaction mixture to determine the amount of a particular compound to add in the second serial addition. For example, contacting can include using a comparison of the percent conversion of the phosphorochloridite in the first reaction mixture to the pre-determined goal for the conversion of the phosphorochloridite in the second reaction mixture to determine the amount of a compound selected from the group consisting of the X—OH, water, or the alcohol having the chemical structure $R^1$—OH or $R^2$—OH to add in the second serial addition such that the percent conversion of the phosphorochloridite in the second reaction mixture is at or above the pre-determined goal.

The pre-determined goal for the conversion of phosphorochloridite in the second reaction mixture can be any suitable pre-determined goal. In some embodiments, the pre-determined goal for the conversion of phosphorochloridite in the second reaction mixture is about 50% to about 100%, or about 70% to about 100%, or about 90% to about 99%, or about 95% to about 99%, or about 98%.

In some embodiments, the pre-determined goal for the conversion of phosphorochloridite in the second reaction mixture is about 80% to about 100%. In some examples, the pre-determined goal for the conversion of phosphorochloridite in the second reaction mixture is about 96% to about 99%. In some examples, the pre-determined goal for the conversion of phosphorochloridite in the first reaction mixture is about 85% to about 95%. In some examples, the pre-determined goal for the conversion of phosphorochloridite in the first reaction mixture is about 90%.

Ligand Hydrolysis Product (LHP)

In some embodiments, decisions about the composition of the second serial addition can be made including using a pre-determined limit for the mole percent of phosphorus present as LHP in the final reaction mixture.

In some embodiments, the ligand hydrolysis products can be any suitable hydrolysis product of any material present in the reaction mixture. When LHPs are discussed herein, any suitable number of LHPs can be referred to, including some or all LHPs. An LHP can include a product derived by a process including hydrolysis of the phosphorus-containing ligand or of the phosphorochloridite. An LHP can include a product derived by a process including hydrolysis of a product derived from the phosphorus-containing ligand or from the phosphorochloridite. An LHP can include a product derived by a process including reaction of a hydrolysis product of the phosphorus-containing ligand or of the phosphorochloridite, or reaction of the hydrolysis product of the a product derived from the phosphorus-containing ligand or from the phosphorochloridite. The LHPs can include any hydrolyzed product of a DLS, TLS, CLS, or the phosphorochloridite, wherein any one P—OR bond therein and any number of P—OR bonds therein is replaced with a P—OH bond. The LHPs can also include materials derived from ligand hydrolysis products, such as for example anhydrides, formed by, for example, reaction of two P—OR bonds to form a P—O—P structure.

In some embodiments, LHP compounds can be derived from the structures shown below:

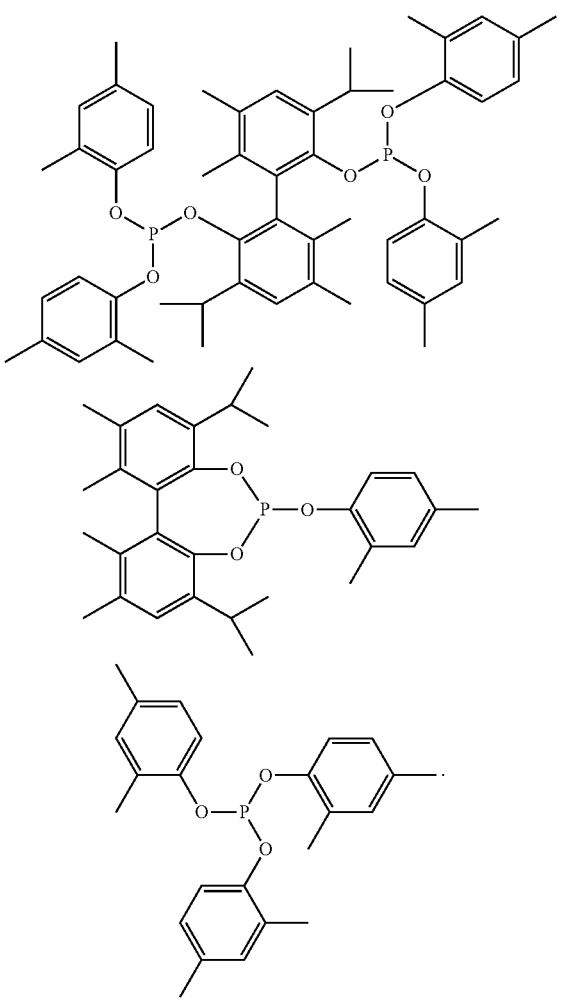

In some embodiments, LHP compounds such as those described in the present paragraph can be identified using $^{31}$P NMR by peaks occurring at about 30 ppm to about −20 ppm.

Determining Mole Percentages and Conversion

The contacting can include determining the mole percent of phosphorus present in the first or second reaction mixture as a side-product. For example, the contacting can include determining the mole percent of phosphorus present in the first or second reaction mixture of CLS, TLS, LHP, or any other suitable side-product. In some embodiments, determining the mole percent of phosphorus present in the first or second reaction mixture as one or more particular side products can include withdrawing samples to analyze the liquid reaction mixture, for example by $^{31}$P NMR, $^1$H NMR, liquid or gas chromatography, mass spectrometry, infrared or UV spectroscopy, or any combination thereof. The samples withdrawn can be any suitable size, and the analytical method used can be any suitable analytical method.

For example, using NMR analysis techniques well known in the art, the integration of NMR peaks that correspond to particular compounds can be used to calculate the mole ratio of various compounds in a reaction mixture, for example based on proportionality between integration ratios and molar ratios. Based a knowledge of the total amounts of reagents added and/or already present in the mixture prior to the last addition, the molar ratios can be used to determine the molar percent of phosphorus present as particular products in the reaction mixture.

First Serial Addition

The contacting includes adding the X—OH compound to the phosphorochloridite in a first serial addition, to provide the first reaction mixture. Any suitable quantity of the X—OH compound can be added to any suitable quantity of the phosphorochloridite in the first serial addition, and the addition can take place at any suitable rate. The first serial addition can occur at any suitable temperature. In one example, the X—OH compound can be a bisaryl compound.

In some examples, the contacting can include using a pre-determined limit for the mole percent of phosphorus present as at least one side-product in the final reaction mixture to determine an amount of the X—OH to add in the first serial addition to cause the mole percent of phosphorus present in the first reaction mixture as the at least one side-product to be less than the pre-determined limit of the mole percent of phosphorus present as the at least one side-product in the final reaction mixture.

In some embodiments, the amount of the X—OH added in the second serial addition can be less than the amount of the X—OH added in the first serial addition.

In some examples, the contacting includes providing a pre-determined goal for a conversion of phosphorochloridite in the first reaction mixture. The contacting can further include, before adding the first serial addition, using the pre-determined goal for the conversion of phosphorochloridite in the first reaction mixture to determine the amount of the X—OH to add in the first serial addition, such that the conversion of phosphorochloridite in the first reaction mixture is at or above the pre-determined goal for the conversion of phosphorochloridite in the first reaction mixture.

In various embodiments, the first reaction mixture can have a stoichiometric excess of phosphorochloridite.

Second Serial Addition

The contacting also includes adding the second serial addition to the second reaction mixture, including at least one of the X—OH compound, water, or the alcohol having the chemical structure $R^1$—OH or $R^2$—OH, to provide the second reaction mixture. Any suitable quantity of at least one of the X—OH compound, water, or the alcohol having the chemical structure $R^1$—OH or $R^2$—OH can be added to the first reaction mixture in the second serial addition, and the addition can take place at any suitable rate. The second serial addition can occur at any suitable temperature. In one example, the X—OH compound can be a bisaryl compound. In embodiments in which third addition steps are not performed, the second reaction mixture is the final reaction mixture. In embodiments in which third addition steps are performed, the second reaction mixture is not the final reaction mixture.

In some embodiments, the contacting can include using a pre-determined limit for the mole percent of phosphorus present as at least one side-product in the final reaction mixture to determine an amount of the X—OH to add in the first or second serial addition to cause a mole percent of phosphorus present in the second reaction mixture as the at least one side-product to be less than the pre-determined limit of the mole percent of phosphorus present as the at least one side-product in the final reaction mixture.

In some examples, the amount of the X—OH added in the second serial addition is none.

In some embodiments, if the amount of the X—OH added in the second serial addition is none, then the second serial addition includes at least one of water or the alcohol having the chemical structure $R^1$—OH or $R^2$—OH.

In some embodiments, using a comparison of the mole percent of phosphorus present in the first reaction mixture as the CLS to the pre-determined limit for the mole percent of phosphorus present as the CLS in the final reaction mixture to determine the amount of a compound to add in the second serial addition includes adding an amount of a compound in the second addition selected from the group consisting of the X—OH, water, and the alcohol having the chemical structure $R^1$—OH or $R^2$—OH sufficient to cause the mole percent of phosphorus in the second reaction mixture present as the CLS to be equal to or below the pre-determined limit for the mole percent of phosphorus present as the CLS in the final reaction mixture. In some examples, if the mole percent of phosphorus present in the first reaction mixture as the CLS is equal to or greater than the pre-determined limit for the mole percent of phosphorus present as the CLS in the final reaction mixture, then the second serial addition includes water or the alcohol having the chemical structure $R^1$—OH or $R^2$—OH. In some examples, if the mole percent of phosphorus present in the first reaction mixture as the CLS is equal to or greater than the pre-determined limit for the mole percent of phosphorus present as the CLS in the final reaction mixture, then the second serial addition does not include the X—OH.

In some embodiments, using a comparison of the mole percent of phosphorus present in the first reaction mixture as the TLS to the pre-determined limit for the mole percent of phosphorus present as the TLS in the final reaction mixture to determine the amount of a compound to add in the second serial addition includes adding an amount of a compound in the second addition selected from the group consisting of the X—OH, water, and the alcohol having the chemical structure $R^1$—OH or $R^2$—OH sufficient to cause the mole percent of phosphorus in the second reaction mixture present as the TLS to be equal to or below the pre-determined limit for the mole percent of phosphorus present as the TLS in the final reaction mixture. In some examples, if the mole percent of phosphorus present in the first reaction mixture as the TLS is equal to or greater than the pre-determined limit for the mole percent of phosphorus present as the TLS in the final reaction mixture, then the second serial addition includes water. In some examples, if the mole percent of phosphorus present in the first reaction mixture as TLS is equal to or greater than the pre-determined limit for the mole percent of phosphorus present as the TLS in the final reaction mixture, then the second serial addition does not include the X—OH or the alcohol having the chemical structure $R^1$—OH or $R^2$—OH.

In some embodiments, using a comparison of the mole percent of phosphorus present in the first reaction mixture as the LHP to the pre-determined limit for the mole percent of phosphorus present as the LHP in the final reaction mixture to determine the amount of a compound to add in the second serial addition includes adding an amount of a compound in the second addition selected from the group consisting of the X—OH, water, and the alcohol having the chemical structure $R^1$—OH or $R^2$—OH sufficient to cause the mole percent of phosphorus in the second reaction mixture present as the LHP to be equal to or below the pre-determined limit for the mole percent of phosphorus present as the LHP in the final reaction mixture. In some examples, if the mole percent of phosphorus present in the first reaction mixture as LHP is equal to or greater than the pre-determined limit for the mole percent of phosphorus present as the LHP in the final reaction mixture, then the second serial addition includes the X—OH or the alcohol having the chemical structure $R^1$—OH or $R^2$—OH. In some examples, if the mole percent of phosphorus present in the first reaction mixture as LHP is equal to or greater than the pre-determined limit for the mole percent of phosphorus present as the LHP in the final reaction mixture, then the second serial addition does not include water.

In some examples, if in the first reaction mixture both the mole percents of phosphorus present as the CLS and the TLS are equal to or greater than the respective pre-determined limits for the mole percents of phosphorus present as the CLS or the TLS in the final reaction mixture, then the second serial addition includes water. In some examples, if in the first reaction mixture both the mole percents of phosphorus present as the CLS and the TLS are equal to or greater than the respective pre-determined limits for the mole percents of phosphorus present as the CLS or the TLS in the final reaction mixture, then the second serial addition does not include the X—OH or the alcohol having the chemical structure $R^1$—OH or $R^2$—OH.

In some examples, the contacting includes providing a pre-determined goal for a conversion of phosphorochloridite in the second reaction mixture. The contacting can further include, after adding the first serial addition, determining the percent conversion of the phosphorochloridite in the first reaction mixture. And, the contacting can further include, before adding the second serial addition, using a comparison of the percent conversion of the phosphorochloridite in the first reaction mixture to the pre-determined goal for the conversion of phosphorochloridite in the second reaction mixture to determine the amount of the X—OH to add in the second serial addition.

In some embodiments, the contacting includes providing a pre-determined goal for a conversion of phosphorochloridite in the second reaction mixture. The contacting can further include, after adding the first serial addition, determining the percent conversion of the phosphorochloridite in the first reaction mixture. The contacting can further include, before adding the second serial addition, using a comparison of the percent conversion of the phosphorochloridite in the first reaction mixture to the pre-determined goal for the conversion of phosphorochloridite in the second reaction mixture to determine the amount of the X—OH to add in the second serial addition. In some examples, if in the first reaction mixture neither the mole percent of phosphorus present as the CLS nor as the TLS is equal to or above the respective pre-determined limits for the mole percents of phosphorus present as the CLS or as the TLS in the final reaction mixture, and the conversion of phosphorochloridite in the first reaction mixture is less than the pre-determined goal for the conversion of phosphorochloridite in the final reaction mixture, then the amount of the X—OH to add in the second serial addition is sufficient to make the percent conversion of the phosphorochloridite in the second reaction mixture equal to or above the pre-determined goal for the conversion of the phosphorochloridite in the second reaction mixture. In some examples, if in the first reaction mixture neither the mole percent of phosphorus present as the CLS nor as the TLS is equal to or above the respective pre-determined limits for the mole percents of phosphorus present as the CLS or as the TLS in the final reaction mixture, and the conversion of phosphorochloridite in the first reaction mixture is less than the pre-determined goal for the conversion of phosphorochloridite in the second reaction mixture, then the second serial addition does not include water or the alcohol having the chemical structure $R^1$—OH or $R^2$—OH.

In some embodiments, contacting can include providing a pre-determined limit for the mole percent of phosphorus present as LHP in the final reaction mixture. Contacting can further include, after adding the first serial addition, determining the mole percent of phosphorus present as LHP in the first reaction mixture. The contacting can further include, before adding the second serial addition, using a comparison of the mole percent of phosphorus present as LHP in the first reaction mixture to the pre-determined limit for the mole percent of phosphorus present as LHP in the final reaction mixture to determine the composition of the second serial addition. In some examples, if in the first reaction mixture the mole percent of phosphorus present as the CLS is equal to or above the pre-determined limit for the mole percent of phosphorus present as the CLS in the final reaction mixture, and in the first reaction mixture the mole percent of phosphorus present as the TLS is not equal to or above the pre-determined limit for the mole percent of phosphorus present as the TLS in the final reaction mixture, and in the first reaction mixture the mole percent of phosphorus present as LHP is equal or to greater than the pre-determined limit for the mole percent of phosphorus present as LHP in the final reaction mixture, then the second serial addition includes the alcohol having the chemical structure $R^1$—OH or $R^2$—OH. In some examples, if in the first reaction mixture the mole percent of phosphorus present as the CLS is equal to or above the pre-determined limit for the mole percent of phosphorus present as the CLS in the final reaction mixture, and in the first reaction mixture the mole percent of phosphorus present as the TLS is not equal to or above the pre-determined limit for the mole percent of phosphorus present as the TLS in the final reaction mixture, and in the first reaction mixture the mole percent of phosphorus present as LHP is equal or to greater than the pre-determined limit for the mole percent of phosphorus present as LHP in the final reaction mixture, then the second serial addition does not include the X—OH or water.

In some embodiments, the contacting can include providing a pre-determined goal for a conversion of phosphorochloridite in the second reaction mixture. The contacting can further include, after adding the first serial addition, determining the percent conversion of the phosphorochloridite in the first reaction mixture. If in the first reaction mixture both the mole percents of phosphorus present as the CLS and the TLS are equal to or greater than the respective pre-determined limits for the mole percents of phosphorus present as the CLS or the TLS in the final reaction mixture, then the second serial addition includes water. If in the first reaction mixture the mole percent of phosphorus present as the CLS is equal to or above the pre-determined limit for the mole percent of phosphorus present as the CLS in the final reaction mixture, and in the first reaction mixture the mole percent of phosphorus present as the TLS is not equal to or above the pre-determined limit for the mole percent of phosphorus present as the TLS in the final reaction mixture, then the second serial addition includes water or the alcohol having the chemical structure $R^1$—OH or $R^2$—OH. If in the first reaction mixture neither the mole percent of phosphorus present as the CLS nor as the TLS is equal to or above the respective pre-determined limits for the mole percents of phosphorus present as the CLS or the TLS in the final reaction mixture, and the conversion of phosphorochloridite in the first reaction product is less than the pre-determined goal for the conversion of phosphorochloridite in the second reaction mixture, then the second serial includes a sufficient amount of the X—OH such that the percent conversion of the phosphorochloridite in the second reaction mixture is equal to or above the pre-determined goal for the conversion of the phosphorochloridite in the second reaction mixture. In some examples, if in the first reaction mixture the mole percent of phosphorus present as the CLS is equal to or above the pre-determined limit for the mole percent of phosphorus present as the CLS in the final reaction mixture, and in the first reaction mixture the mole percent of phosphorus present as the TLS is not equal to or above the pre-determined limit for the mole percent of phosphorus present as the TLS in the final reaction mixture, then the second serial addition includes the alcohol having the chemical structure $R^1$—OH or $R^2$—OH.

In some embodiments, contacting includes providing a pre-determined goal for a conversion of phosphorochloridite in the second reaction mixture. Contacting can further include, after adding the first serial addition, determining the percent conversion of the phosphorochloridite in the first reaction mixture and determining the mole percent of phosphorus present as LHP in the first reaction mixture. If in the first reaction mixture both the mole percents of phosphorus present as the CLS and the TLS are equal to or greater than the respective pre-determined limits for the mole percents of phosphorus present as the CLS or the TLS in the final reaction mixture, then the second serial addition includes water. If in the first reaction mixture the mole percent of phosphorus present as the CLS is equal to or above the pre-determined limit for the mole percent of phosphorus present as the CLS in the final reaction mixture, and in the first reaction mixture the mole percent of phosphorus present as the TLS is not equal to or above the pre-determined limit for the mole percent of phosphorus present as the TLS in the final reaction mixture, and in the first reaction mixture the mole percent of phosphorus present as LHP is equal or to greater than the pre-determined limit for the mole percent of phosphorus present as LHP in the final reaction mixture, then the second serial addition includes the alcohol having the chemical structure $R^1$—OH or $R^2$—OH; and if in the first reaction mixture neither the mole percent of phosphorus present as the CLS nor the TLS is equal to or above the respective pre-determined limits for the mole percents of phosphorus present as the CLS or the TLS in the final reaction mixture, and the conversion of phosphorochloridite in the first reaction product is less than the pre-determined goal for the conversion of phosphorochloridite in the second reaction mixture, then second serial addition includes X—OH in sufficient quantity such that the percent conversion of the phosphorochloridite in the second reaction mixture is equal to or above the pre-determined goal for the conversion of the phosphorochloridite in the second reaction mixture. In some examples, if in the first reaction mixture the mole percent of phosphorus present as the CLS is equal to or above the pre-determined limit for the mole percent of phosphorus present as the CLS in the final reaction mixture, and in the first reaction mixture the mole percent of phosphorus present as the TLS is not equal to or above the pre-determined limit for the mole percent of phosphorus present as the TLS in the final reaction mixture, and in the first reaction mixture the mole percent of phosphorus present as LHP is not equal or to greater than the pre-determined limit for the mole percent of phosphorus present as LHP in the final reaction mixture, then the second serial addition includes water or the alcohol having the chemical structure $R^1$—OH or $R^2$—OH; and if in the first reaction mixture the mole percent of phosphorus present as the TLS is equal to or above the pre-determined limit for the mole percent of phosphorus present as the TLS in the final reaction mixture, and in the first reaction mixture the mole percent of phosphorus present as the CLS is not equal to or above the pre-determined limit for the mole percent of phosphorus present as the CLS in the final reaction mixture, and in the first reaction mixture the mole percent of phosphorus present as LHP is not equal or to greater than the pre-determined limit for LHP content in the final reaction mixture, then the second addition includes water. In some examples, if in the first reaction mixture the mole percent of phosphorus present as the CLS is equal to or above the pre-determined limit for the mole percent of phosphorus present as the CLS in the final reaction mixture, and in the first reaction mixture the mole percent of phosphorus present as the TLS is not equal to or above the pre-determined limit for the mole percent of phosphorus present as the TLS in the final reaction mixture, and in the first reaction mixture the mole percent of phosphorus present as LHP is not equal or to greater than the pre-determined limit for the mole percent of phosphorus present as LHP in the final reaction mixture, then the second serial addition does not include the X—OH; and, if in the first reaction mixture the mole percent of phosphorus present as the TLS is equal to or above the pre-determined limit for the mole percent of phosphorus present as the TLS in the final reaction mixture, and in the first reaction mixture the mole percent of phosphorus present as the CLS is not equal to or above the pre-determined limit for the mole percent of phosphorus present as the CLS in the final reaction mixture, and in the first reaction mixture the mole percent of phosphorus present as LHP is not equal or to greater than the pre-determined limit for LHP content in the final reaction mixture, then the second addition does not include water or the alcohol having the chemical structure $R^1$—OH or $R^2$—OH.

In some embodiments, the weight ratio of the X—OH added in the first serial addition to the X—OH added in the second serial addition is from 9.0:1.0 to 9.9:1.0.

Optional Third Serial Addition

The contacting also either includes performing third addition steps, or the final reaction mixture is the second reaction mixture. If the contacting includes performing third addition steps, the final reaction mixture is not the second reaction mixture. If the contacting does not include performing third additional steps, the final reaction mixture is the second reaction mixture.

The third addition steps, if performed, include optionally using a comparison of the mole percent of phosphorus present in the second reaction mixture as the at least one side-product to the pre-determined limit for the mole percent of phosphorus present as the at least one side-product in the final reaction mixture, to determine an amount of a compound selected from the group consisting of the X—OH, water, and the alcohol having the chemical structure $R^1$—OH or $R^2$—OH, to add in a third serial addition. In some embodiments, if third addition steps are performed, the step of using a comparison of the mole percent of phosphorus present in the second reaction mixture as the at least one side-product to the pre-determined limit for the mole percent of phosphorus present as the at least one side-product in the final reaction mixture, to determine an amount of a compound selected from the group consisting of the X—OH, water, and the alcohol having the chemical structure $R^1$—OH or $R^2$—OH, to add in a third serial addition, is performed. In other embodiments, if third addition steps are performed, the step of using a comparison of the mole percent of phosphorus present in the second reaction mixture as the at least one side-product to the pre-determined limit for the mole percent of phosphorus present as the at least one side-product in the final reaction mixture, to determine an amount of a compound selected from the group consisting of the X—OH, water, and the alcohol having the chemical structure $R^1$—OH or $R^2$—OH, to add in a third serial addition is not performed. The third addition steps, if performed, include optionally determining a mole percent of phosphorus present in the second reaction mixture as the at least one side-product. In some embodiments, if the third addition steps are performed, the step of determining a mole percent of phosphorus present in the second reaction mixture as the at least one side-product is performed. In other embodiments, if the third addition steps are performed, the step of determining a mole percent of phosphorus present in the second reaction mixture as the at least one side-product is not performed. The third addition steps, if performed, include adding the third serial addition to the second reaction mixture, including a compound selected from the group consisting of the X—OH, water, and the alcohol having the chemical structure $R^1$—OH or $R^2$—OH, to provide the final reaction mixture.

In some embodiments, the contacting includes using the pre-determined limit for the mole percent of phosphorus present as the at least one side-product in the final reaction mixture to determine an amount of the X—OH to add in the third serial addition to cause a mole percent of phosphorus present in the final reaction mixture as the at least one side-product to be less than the pre-determined limit of the mole percent of phosphorus present as the at least one side-product in the final reaction mixture.

In some examples, the amount of the X—OH added in the third serial addition if performed is equal to or less than the amount of the X—OH added in the second serial addition. In some examples, the amount of the X—OH added in the third serial addition is none. In some examples, if the amount of the X—OH added in the third serial addition is none, then the third serial addition if performed includes at least one of water or the alcohol having the chemical structure $R^1$—OH or $R^2$—OH.

In some embodiments, using a comparison of the mole percent of phosphorus present in the second reaction mixture as the CLS to the pre-determined limit for the mole percent of phosphorus present as the CLS in the final reaction mixture to determine the amount of a compound to add in the third serial addition if performed includes adding an amount of a compound in the third addition selected from the group consisting of the X—OH, water, and the alcohol having the chemical structure $R^1$—OH or $R^2$—OH sufficient to cause the mole percent of phosphorus in the final reaction mixture present as the CLS to be equal to or below the pre-determined limit for the mole percent of phosphorus present as the CLS in the final reaction mixture. In some examples, if the mole percent of phosphorus present in the second reaction mixture as the CLS is equal to or greater than the pre-determined limit for the mole percent of phosphorus present as the CLS in the final reaction mixture, then the third serial addition if performed includes water or the alcohol having the chemical structure $R^1$—OH or $R^2$—OH. In some examples, if the mole percent of phosphorus present in the second reaction mixture as the CLS is equal to or greater than the pre-determined limit for the mole percent of phosphorus present as the CLS in the final reaction mixture, then the third addition if performed does not include the X—OH.

In some embodiments, using a comparison of the mole percent of phosphorus present in the second reaction mixture as the TLS to the pre-determined limit for the mole percent of phosphorus present as the TLS in the final reaction mixture to determine the amount of a compound to add in the third serial addition includes adding an amount of a compound in the third addition selected from the group consisting of the X—OH, water, and the alcohol having the chemical structure $R^1$—OH or $R^2$—OH sufficient to cause the mole percent of phosphorus in the final reaction mixture present as the TLS to be equal to or below the pre-determined limit for the mole percent of phosphorus present as the TLS in the final reaction mixture. In some examples, if the mole percent of phosphorus present in the second reaction mixture as the TLS is equal to or greater than the pre-determined limit for the mole percent of phosphorus present as the TLS in the final reaction mixture, then the third serial addition if performed includes water. In some examples, if the mole percent of phosphorus present in the second reaction mixture as TLS is equal to or greater than the pre-determined limit for the mole percent of phosphorus present as the TLS in the final reaction mixture, then the third serial addition if performed does not include the X—OH or the alcohol having the chemical structure $R^1$—OH or $R^2$—OH.

In some embodiments, using a comparison of the mole percent of phosphorus present in the second reaction mixture as the TLS to the pre-determined limit for the mole percent of phosphorus present as the TLS in the final reaction mixture to determine the amount of a compound to add in the third serial addition includes adding an amount of a compound in the third addition selected from the group consisting of the X—OH, water, and the alcohol having the chemical structure $R^1$—OH or $R^2$—OH sufficient to cause the mole percent of phosphorus in the final reaction mixture present as the TLS to be equal to or below the pre-determined limit for the mole percent of phosphorus present as the TLS in the final reaction mixture. In some examples, if the mole percent of phosphorus present in the second reaction mixture as the TLS is equal to or greater than the pre-determined limit for the mole percent of phosphorus present as the TLS in the final reaction mixture, then the third serial addition if performed includes water. In some examples, if the mole percent of phosphorus present in the second reaction mixture as TLS is equal to or greater than the pre-determined limit for the mole percent of phosphorus present as the TLS in the final reaction mixture, then the third serial addition if performed does not include the X—OH or the alcohol having the chemical structure $R^1$—OH or $R^2$—OH.

In some examples, if percent conversion of the phosphorochloridite in the second reaction mixture is less than about 100%, then the contacting further includes adding the third serial addition to the second reaction mixture, wherein the third serial addition includes a sufficient quantity of water or the alcohol having the chemical structure $R^1$—OH or $R^2$—OH such that following the third serial addition the phosphorochloridite conversion in the final reaction mixture is about 100%.

In some examples, contacting includes determining the percent conversion of the phosphorochloridite in the second reaction mixture and determining the mole percent of phosphorus present as TLS in the second reaction mixture, wherein if percent conversion of the phosphorochloridite in the second reaction mixture is less than about 100%, and if in the second reaction mixture the mole percent of phosphorus present as TLS is less than the pre-determined limit for the mole percent of phosphorus present as TLS in the final reaction mixture, then further including adding the third serial addition to the second reaction mixture, wherein the third serial addition includes a sufficient quantity of the alcohol having the chemical structure $R^1$—OH or $R^2$—OH such that following the third serial addition the conversion of the phosphorochloridite in the final reaction mixture is about 100%.

In some embodiments, if percent conversion of the phosphorochloridite in the second reaction mixture is less than about 100%, and if in the second reaction mixture the mole percent of phosphorus present as LHP is less than the pre-determined limit for the mole percent of phosphorus present as LHP in the final reaction mixture, then the contacting further includes adding a third serial addition to the second reaction mixture, wherein the third serial addition includes a sufficient quantity of water such that following the third serial addition the conversion of the phosphorochloridite in the final reaction mixture is about 100%.

In some embodiments, the first serial addition includes the X—OH in sufficient quantity such that the conversion of the phosphorochloridite in the first reaction mixture is about 85% to about 95%. After the second serial addition, the conversion of the phosphorochloridite in the second reaction mixture can be about 95% to about 99%. The third serial addition can include water or the alcohol having the chemical structure $R^1$—OH or $R^2$—OH in sufficient quantity such that the conversion of the phosphorochloridite in the final reaction mixture is about 100%.

Forecasting

In various embodiments, using a comparison of the percent conversion of the phosphorochloridite in the first reaction mixture to the pre-determined goal for the conversion of phosphorochloridite in the second reaction mixture to determine the amount of the X—OH to add in the second serial addition can include a forecasting process. The forecasting can be any suitable forecasting, wherein the amount of X—OH to add in the second addition is sufficient to create as much DLS as possible and to consume as much phosphorochloridite as possible without causing the levels of a side-product to exceed a pre-determined limit for that side-product in the final reaction mixture. Following the second addition, the remainder of the phosphorochloridite in the second reaction mixture (if any, e.g. if the second reaction mixture is not the final reaction mixture) can be consumed using an addition of water or by addition of the alcohol having the structure $R^1$—OH or $R^2$—OH. If a third addition is used, the quantity of water or alcohol to add in the third addition to consume the reminder of the phosphorochloridite can be estimated using any suitable method, such as using the selectivity ratios at various conversion ranges as described below.

The forecasting process can include using at least one selectivity ratio of the phosphorochloridite to the phosphorus-containing ligand and CLS at a given conversion range to forecast a maximum percent conversion of phosphorochloridite such that at the forecasted percent conversion in the second reaction mixture the percent of phosphorus present as CLS in the second reaction mixture is less than the pre-determined limit for the percent of phosphorus present as CLS in the final reaction mixture. The forecasting process can further include setting the pre-determined goal for the conversion of phosphorochloridite in the second reaction mixture to the forecasted maximum percent conversion of the phosphorochloridite. The forecasting process can further include adding an amount of the X—OH in the second serial addition sufficient to cause the percent conversion of the phosphorochloridite in the second reaction mixture to be about equal to the pre-determined goal for the conversion of the phosphorochloridite in the second reaction mixture.

In some embodiments, the selectivity ratio of the phosphorochloridite to the phosphorus-containing ligand and CLS at a given conversion range includes a molar selectivity ratio of CLS to phosphorus-containing ligand of about 1:6 for conversions up to about 98%, for example for a conversions of about 90% to about 98%. In some examples, the selectivity ratio of the phosphorochloridite to the phosphorus-containing ligand and CLS at a given conversion range includes a molar selectivity ratio of CLS to phosphorus-containing ligand of about 1:1 for conversions of between about 98% and about 100%.

In embodiments, the selectivity ratio of the phosphorochloridite to the phosphorus-containing ligand and CLS at a given conversion range can occur at any suitable conversion range. For example, the conversion range of the phosphorochloridite can be about 0% to about 20%, about 0% to about 50%, about 0% to about 90%, about 0% to about 95%, about 0% to about 100%, about 20% to about 40%, about 40% to about 60%, about 60% to about 80%, or about 80% to about 100%. In embodiments, the selectivity ratio at the given conversion range can be any suitable selectivity ratio, for example, the selectivity ratio of the phosphorochloridite to the phosphorus-containing ligand and CLS at a given conversion range can be about 1:(0.001-1000), such as about 1:0.001, 1:0.01, 1:0.1, 1:1, 1:2, 1:4, 1:6, 1:8, 1:10, 1:12, 1:14, 1:16, 1:18, 1:20, 1:100, or about 1:1000 molar ratio. In some examples, the selectivity ratio can be experimentally determined.

In some embodiments, a forecasting process can include using at least one selectivity ratio of the phosphorochloridite to the phosphorus-containing ligand and TLS at a given conversion range to forecast a maximum percent conversion of phosphorochloridite such that at the forecasted percent conversion in the second reaction mixture the percent of phosphorus present as TLS in the second reaction mixture is less than the pre-determined limit for the percent of phosphorus present as TLS in the final reaction mixture. The forecasting process can further include setting the pre-determined goal for the conversion of phosphorochloridite in the second reaction mixture to the forecasted maximum percent conversion of the phosphorochloridite. The forecasting process can further include adding an amount of the X—OH in the second serial addition sufficient to cause the percent conversion of the phosphorochloridite in the second reaction mixture to be about equal to the pre-determined goal for the percent conversion of the phosphorochloridite in the second reaction mixture.

In some embodiments, the selectivity ratio of the phosphorochloridite to the phosphorus-containing ligand and TLS at a given conversion range includes a molar selectivity ratio of TLS to phosphorus-containing ligand of about 1:6 for conversions up to about 98%, for example for a conversion of about 90% to about 98%. In some examples, the selectivity ratio of the phosphorochloridite to the phosphorus-containing ligand and TLS at a given conversion range includes a molar selectivity ratio of TLS to phosphorus-containing ligand of about 1:1 for conversions of between about 98% and about 100%.

In embodiments, the selectivity ratio of the phosphorochloridite to the phosphorus-containing ligand and TLS at a given conversion range can occur at any suitable conversion range. For example, the conversion range of the phosphorochloridite can be about 0% to about 20%, about 0% to about 50%, about 0% to about 90%, about 0% to about 95%, about 0% to about 100%, about 20% to about 40%, about 40% to about 60%, about 60% to about 80%, or about 80% to about 100%. In embodiments, the selectivity ratio at the given conversion range can be any suitable selectivity ratio, for example, the selectivity ratio of the phosphorochloridite to the phosphorus-containing ligand and TLS at a given conversion range can be about 1:(0.001-100), such as about 1:0.001, 1:0.01, 1:0.1, 1:1, 1:2, 1:4, 1:6, 1:8, 1:10, 1:12, 1:14, 1:16, 1:18, 1:20, 1:100, or about 1:1000 molar ratio. In some examples, the selectivity ratio can be experimentally determined.

Reproducability

In some embodiments of the present invention, the impurity levels or yield of the final reaction mixture are highly reproducible within tight tolerances. This can be a major advantage of the present invention over other methods of making phosphorus-containing ligands.

For example, in some embodiments, the percent yield of the phosphorus-containing ligand between repetitions of the method is within 5%. In various embodiments, the percent yield of the phosphorus-containing ligand between repetitions can consistently be within 1%, 2%, 3%, 4%, 5%, 6%, 7%, 8%, 9%, 10%, 15%, 20%, 25%. For consistency, the tolerance can be achieved 2, 3, 4, 5, 10, 15, 20, 40, 60, 80, 100, 500, or over 1000 times without failure.

In some embodiments, the percentage of phosphorus present as TLS in the final product mixture is within 5% of the percentage of phosphorus present as TLS between repetitions of the method. In various embodiments, the percentage of phosphorus present as TLS in the final product mixture between repetitions can consistently be within 1%, 2%, 3%, 4%, 5%, 6%, 7%, 8%, 9%, 10%, 15%, 20%, 25%. For consistency, the tolerance can be achieved 2, 3, 4, 5, 10, 15, 20, 40, 60, 80, 100, 500, or over 1000 times without failure.

In some embodiments, the percentage of phosphorus preset as CLS in the final product mixture is within 5% of the percentage of phosphorus present as CLS between repetitions of the method. In various embodiments, the percentage of phosphorus present as TLS in the final product mixture between repetitions can consistently be within 1%, 2%, 3%, 4%, 5%, 6%, 7%, 8%, 9%, 10%, 15%, 20%, 25%. For consistency, the tolerance can be achieved 2, 3, 4, 5, 10, 15, 20, 40, 60, 80, 100, 500, or over 1000 times without failure.

In some embodiments, the percentage of phosphorus preset as LHP in the final product mixture is within 5% of the percentage of phosphorus present as LHP between repetitions of the method. In various embodiments, the percentage of phosphorus present as TLS in the final product mixture between repetitions can consistently be within 1%, 2%, 3%, 4%, 5%, 6%, 7%, 8%, 9%, 10%, 15%, 20%, 25%. For consistency, the tolerance can be achieved 2, 3, 4, 5, 10, 15, 20, 40, 60, 80, 100, 500, or over 1000 times without failure.

In some embodiments, any one or any combination of tolerances for various side-products or yields can be achieved.

EXAMPLES

The present invention can be better understood by reference to the following examples which are offered by way of illustration. The present invention is not limited to the examples given herein.

The equipment used in the Examples that follow was a glass-lined reactor (nominal capacity about 630 L, inside diameter about 1,000 mm, jacket surface area about 3.2 m$^2$), impellor (about 480 mm diameter, 4 pitched-blades, downward pumping, maximum agitator speed 188 rpm), 2 finger baffles at opposite sides of reactor, 2 separate feeds pipes positioned near the impellor tip (4 mm diameter polytetrafluoroethylene (PTFE) tubes inside the finger baffles), sample withdrawal system, and a thermocouple (inside a finger baffle). There were no metallic components in contact with the fluid, glass-lined reactor, glass-coated agitator and baffles, or PTFE feed tubes.

During operation, the feeds were dosed to the reactor using manually controlled, positive displacement, piston pumps, with adjustments based on loss in weight (weigh scales). During dosage, the reaction mixture was stirred and the reaction temperature was controlled at about 50° C. by the use of jacket cooling.

In the Examples that follow, the process goal was to maximise DLS yield while limiting amounts of side-products in the final reaction mixture to a maximum of about 3 molar percent of phosphorus present as CLS and to a maximum of about 3 molar percent of phosphorus present as LHP.

In all the Examples, the phosphorochloridite starting mixture was generated using a method similar to that described by PCT Publication WO 2004/050588. To a mixture of phosphorus trichloride (25 kg) in toluene (300 kg) was added 2,4-xylenol (45.5 kg) and triethylamine (39 kg) with stirring at about 50° C.

In all the Examples, the following procedure was used: (a) Phosphorus Nuclear Magnetic Resonance Spectroscopy ($^{31}$P NMR) was used to determine the phosphorus distribution of the starting mixture and this analysis was used to calculate the first serial dose of triethylamine and bis-aryl compound, to target about 90% phosphorochloridite conversion in the first reaction mixture. (b) After the first serial dose, $^{31}$P NMR was used to determine the phosphorus distribution of the first reaction mixture and this analysis was used to calculate (e.g. forecast) the second serial dose of bisaryl compound to limit CLS content in the second reaction mixture to a maximum of about 3 molar percent phosphorus (e.g. to add as much bisaryl as possible without causing the CLS content in the second reaction mixture to excess the pre-determined limit for CLS content in the final reaction mixture). (c) After the second serial addition to give the second reaction mixture, phosphorochloridite conversion was completed by adding the third addition, a small excess of 2,4-xylenol, to the second reaction mixture to give the final reaction mixture. In every case, the option of adding water to the second reaction mixture, instead of 2,4-xylenol, to complete phosphorochloridite conversion was rejected since this would have exceeded the LHP concentration maximum (e.g. would have exceeded the pre-determined limit for LHP content in the final reaction mixture). (d) After the third addition, $^{31}$P NMR was used to determine the phosphorus distribution of the final product mixture and this analysis was used to confirm the process goal had been achieved.

In the following examples, particular selectivity ratios are used for various ranges of phosphorochloridite conversion. These are only examples of particular selectivity ratios for various ranges of conversion, other selectivity ratios can be used. In one example, particular selectivity ratios can be determined experimentally.

In the following examples, the DLS structure formed had the following chemical structure:

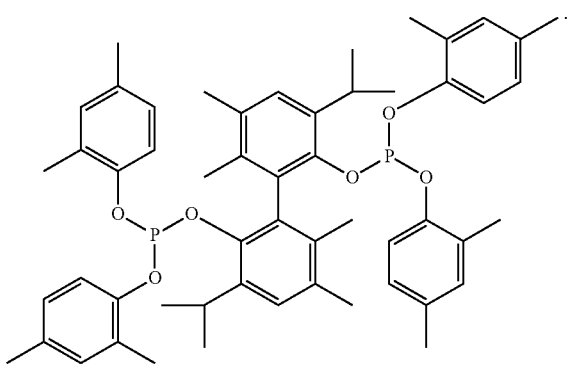

In the following examples, the bisaryl compound added had the following structure:

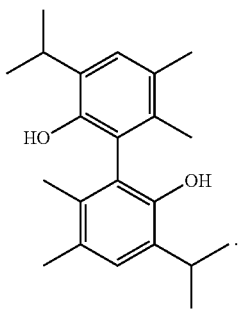 [SMILES: Cc1cc(C(C)C)c(O)c(-c2c(C)c(C)cc(C(C)C)c2O)c1C ; "."]

In the following examples, the CLS structure formed had the following structure:

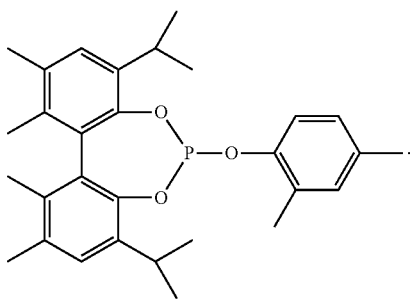

In the following examples, the TLS structure formed had the following structure:

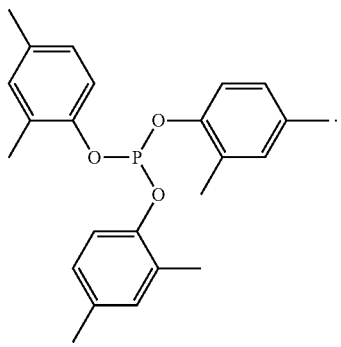 [SMILES: Cc1ccc(OP(Oc2ccc(C)cc2C)Oc2ccc(C)cc2C)c(C)c1 ; "."]

Example 1

Phosphorus Distribution—Starting Mixture

| Phosphorus Containing Component | Mol % P (approx) | Kg (approx) |
|---|---|---|
| DLS | 0 | 0 |
| TLS | 8 | 5.7 |
| CLS | 0 | 0 |
| Phosphorochloridite | 87 | 48.7 |
| LHP | 2 | |
| Other | 3 | |

First serial dose—To the stirred suspension was added a stoichiometric excess of triethylamine (20.3 kg) in one portion followed by bisaryl compound (22.3 kg) dissolved in toluene (36 wt %) dosed continuously over about 2 hours. The reaction mixture was then analysed by $^{31}$P NMR.

Phosphorus Distribution—First Reaction Mixture

| Phosphorus Containing Component | Mol % P (approx) | Kg (approx) |
|---|---|---|
| DLS | 69 | 54.7 |
| TLS | 14 | 10.1 |
| CLS | 2 | 1.7 |
| Phosphorochloridite | 10 | 5.6 |
| LHP | 3 | |
| Other | 2 | |

Second Serial dose—The second serial dose was calculated by running a by-product accumulation model. Using the selectivity ratio for the respective ranges of phosphorochloridite conversion, it was forecasted that molar percent of phosphorus present as CLS in the final reaction mixture would exceed 3% if the bisaryl addition continued to complete conversion of the phosphorochloridite.

Selectivity Ratios at Various Conversion Ranges

| | Molar Selectivity Ratio | | |
|---|---|---|---|
| Phosphorochloridite Conversion | DLS | CLS | TLS |
| 90% to 98% | 6 | 1 | 1 |
| 98% to 100% | 1 | 1 | 1 |

By-Product Accumulation Model

| Phosphorochloridite percent conversion | CLS (mol) | TLS (mol) |
|---|---|---|
| 10 | 2.00 | 14.00 |
| 9 | 2.13 | 14.13 |
| 8 | 2.25 | 14.25 |
| 7 | 2.38 | 14.38 |
| 6 | 2.50 | 14.50 |
| 5 | 2.63 | 14.63 |
| 4 | 2.75 | 14.75 |
| 3 | 2.88 | 14.88 |
| 2 | 3.00 | 15.00 |
| 1 | 3.33 | 15.33 |
| 0 | 3.67 | 15.67 |

To the stirred suspension was added a further quantity of bisaryl compound (2.7 kg) over about 60 minutes, targeting about 2% conversion of the phosphorochloridite in the second reaction mixture. This was followed by addition of a dose of 2,4-xylenol (0.5 kg) sufficient to complete the conversion of the phosphorochloridite, plus a small excess. The final reaction mixture was then analysed by $^{31}$P NMR.

Phosphorus Distribution—Final Reaction Mixture

| Phosphorus Containing Component | Mol % P (approx) | Kg (approx) |
|---|---|---|
| DLS | 76 | 60.3 |
| TLS | 16 | 11.5 |
| CLS | 3 | 2.6 |
| Phosphorochloridite | 0 | 0 |
| LHP | 2 | |
| Other | 3 | |

Example 2

Phosphorus Distribution—Starting Mixture

| Phosphorus Containing Component | Mol % P (approx) | Kg (approx) |
|---|---|---|
| DLS | 0 | 0 |
| TLS | 9 | 6.5 |
| CLS | 0 | 0 |
| Phosphorochloridite | 86 | 48.1 |
| LHP | 1 | |
| Other | 4 | |

First Serial Dose—To the stirred suspension was added a stoichiometric excess of triethylamine (22 kg) in one portion and bisaryl compound (22.8 kg) dissolved in toluene (30.5 wt %) dosed continuously over about 2 hours. The reaction mixture was then analysed by $^{31}$P NMR.

Phosphorus Distribution—First Reaction Mixture

| Phosphorus Containing Component | Mol % P (approx) | Kg (approx) |
|---|---|---|
| DLS | 68 | 53.9 |
| TLS | 15 | 10.5 |
| CLS | 2.4 | 2.1 |
| Phosphorochloridite | 10.3 | 5.6 |
| LHP | 2.3 | |
| Other | 2 | |

Second Serial Dose—It was forecasted that the percentage of phosphorus present as CLS in the second reaction mixture would reach 3% at about 95% phosphorochloridite conversion.

Selectivity Ratios at Various Conversion Ranges

| | Molar Selectivity Ratio | | |
|---|---|---|---|
| Phosphorochloridite Conversion | DLS | CLS | TLS |
| 90% to 98% | 6 | 1 | 1 |
| 98% to 100% | 1 | 1 | 1 |

By-Product Accumulation Model

| Phosphorochloridite percent conversion | CLS (mol) | TLS (mol) |
|---|---|---|
| 10 | 2.40 | 14.60 |
| 9 | 2.53 | 14.73 |
| 8 | 2.65 | 14.85 |
| 7 | 2.78 | 14.98 |
| 6 | 2.90 | 15.10 |
| 5 | 3.03 | 15.23 |
| 4 | 3.15 | 15.35 |
| 3 | 3.28 | 15.48 |
| 2 | 3.40 | 15.60 |
| 1 | 3.73 | 15.93 |
| 0 | 4.07 | 16.27 |

To the stirred suspension was added a further quantity of bisaryl compound (2.5 kg) over about 60 minutes, targeting about 5% phosphorochloridite conversion, followed by a small dose of 2,4-xylenol (0.9 kg). The final reaction mixture was then analysed by $^{31}$P NMR.

Phosphorus Distribution—Final Product Mixture

| Phosphorus Containing Component | Mol % P (approx) | Kg (approx) |
|---|---|---|
| DLS | 75 | 57.1 |
| TLS | 19 | 14.4 |
| CLS | 3 | 2.6 |
| Phosphorochloridite | 0 | 0 |
| LHP | 2 | |
| Other | 1 | |

Example 3

Phosphorus Distribution—Starting Mixture

| Phosphorus Containing Component | Mol % P (approx) | Kg (approx) |
|---|---|---|
| DLS | 0 | 0 |
| TLS | 11.4 | 8.3 |
| CLS | 0 | 0 |
| Phosphorochloridite | 81 | 45.6 |
| LHP | 3.6 | |
| Other | 4 | |

First Serial Dose—To the stirred suspension was added a stoichiometric excess of triethylamine (21 kg) in one portion and bisaryl compound (22.3 kg) dissolved in toluene (35.4 wt %) dosed continuously over about 2 hours. The first reaction mixture was then analysed by $^{31}$P NMR.

Phosphorus Distribution—First Reaction Mixture

| Phosphorus Containing Component | Mol % P (approx) | Kg (approx) |
|---|---|---|
| DLS | 66.6 | 52.8 |
| TLS | 13.3 | 9.5 |
| CLS | 2 | 1.7 |
| Phosphorochloridite | 11.8 | 6.6 |
| LHP | 2.6 | |
| Other | 3.7 | |

Second Serial Dose—It was forecasted that the molar percentage of phosphorus present as CLS in the second reaction mixture would reach about 3% at about 96% phosphorochloridite conversion.

Selectivity Ratios at Various Conversion Ranges

|  | Molar Selectivity Ratio | | |
|---|---|---|---|
| Phosphorochloridite Conversion | DLS | CLS | TLS |
| 90% to 98% | 6 | 1 | 1 |
| 98% to 100% | 1 | 1 | 1 |

By-Product Accumulation Model

| Phosphorochloridite percent conversion | CLS (mol) | TLS (mol) |
|---|---|---|
| 11.8 | 2.00 | 13.30 |
| 10 | 2.23 | 13.53 |
| 9 | 2.35 | 13.65 |
| 8 | 2.48 | 13.78 |
| 7 | 2.60 | 13.90 |
| 6 | 2.73 | 14.03 |
| 5 | 2.85 | 14.15 |
| 4 | 2.98 | 14.28 |
| 3 | 3.10 | 14.40 |
| 2 | 3.43 | 14.73 |
| 1 | 3.77 | 15.07 |
| 0 | 4.10 | 15.40 |

To the stirred suspension was added a further quantity of bisaryl compound (2.7 kg) over about 60 minutes, targeting about 4% phosphorochloridite conversion in the second reaction mixture, followed by a small dose of 2,4-xylenol (1.0 kg). The final reaction mixture was then analysed by $^{31}$P NMR.

Phosphorus Distribution—Final Product Mixture

| Phosphorus Containing Component | Mol % P (approx) | Kg (approx) |
|---|---|---|
| DLS | 71.5 | 56.3 |
| TLS | 20.5 | 14.1 |
| CLS | 3.4 | 2.9 |
| Phosphorochloridite | 0 | 0 |
| LHP | 2.6 | |
| Other | 2 | |

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed can be resorted to by those skilled in the art, and that such modifications and variations are considered to be within the scope of this invention as defined by the appended claims.

Additional Embodiments

The present invention provides for the following exemplary embodiments, the numbering of which is not to be construed as designating levels of importance:

Embodiment 1 provides a method for producing a phosphorus-containing ligand structure having the following chemical structure

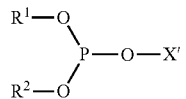

Structure I' including:
contacting a phosphorochloridite of the following structure,

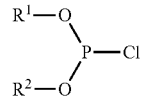

Structure II with a compound having the chemical structure X—OH and a tertiary organic amine to provide a final reaction mixture including the ligand structure;
wherein the contacting includes
providing a pre-determined limit for a mole percent of phosphorus present as at least one side-product in the final reaction mixture;
adding the X—OH to the phosphorochloridite in a first serial addition, to provide a first reaction mixture;
determining a mole percent of phosphorus present in the first reaction mixture as the at least one side-product;
using a comparison of the mole percent of phosphorus present in the first reaction mixture as the at least one side-product to the pre-determined limit for the mole percent of phosphorus present as the at least one side-product in the final reaction mixture, to determine an amount of a compound selected from the group consisting of the X—OH, water, and an alcohol having the chemical structure $R^1$—OH or $R^2$—OH, to add in a second serial addition;
adding the second serial addition to the first reaction mixture, including a compound selected from the group consisting of the X—OH, water, or the alcohol having the chemical structure $R^1$—OH or $R^2$—OH, to provide a second reaction mixture; and
either
performing third addition steps including
optionally determining a mole percent of phosphorus present in the second reaction mixture as the at least one side-product;
optionally using a comparison of the mole percent of phosphorus present in the second reaction mixture as the at least one side-product to the pre-determined limit for the mole percent of phosphorus present as the at least one side-product in the final reaction mixture, to determine an amount of a compound selected from the group consisting of the X—OH, water, and the alcohol having the chemical structure $R^1$—OH or $R^2$—OH, to add in a third serial addition; and
adding the third serial addition to the second reaction mixture, including a compound selected from the group consisting of the X—OH, water, and the alcohol having the chemical structure $R^1$—OH or $R^2$—OH, to provide the final reaction mixture;
or
the final reaction mixture is the second reaction mixture;
wherein in Structures I' and II, $R^1$ and $R^2$ are the same or different, substituted or unsubstituted, monovalent aryl groups; $R^1$ and $R^2$ are bridged to one another or unbridged to one another; and each of X and X' are independently selected from the group consisting of hydrogen, alkyl, aryl, heteroaryl, aryloxy, heteroaryloxy, alkyloxy, alkoxyalkyl, acetal, carboaryloxy, carboalkoxy, arylcarbonyl, alkylcarbonyl, phosphitylbisaryl, phosphitylbisheteroaryl, hydroxybisaryl, hydroxybisheteroaryl, oxazole, amine, amide, nitrile, mercaptyl, and halogen groups.

Embodiment 2 provides the method of Embodiment 1, wherein third addition steps are performed and further include:

determining a mole percent of phosphorus present in the second reaction mixture as the at least one side-product; and using a comparison of the mole percent of phosphorus present in the second reaction mixture as the at least one side-product to the pre-determined limit for the mole percent of phosphorus present as the at least one side-product in the final reaction mixture, to determine an amount of a compound selected from the group consisting of the X—OH, water, and the alcohol having the chemical structure $R^1$—OH or $R^2$—OH, to add in a third serial addition.

Embodiment 3 provides the method of any one of Embodiments 1-2, wherein the ligand structure of Structure I' is a diphosphite ligand structure (DLS) having the chemical structure of Structure I,

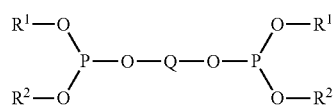

Structure I wherein the X—OH is a bisaryl compound selected from the group consisting of Structure III, Structure IV, and Structure V,

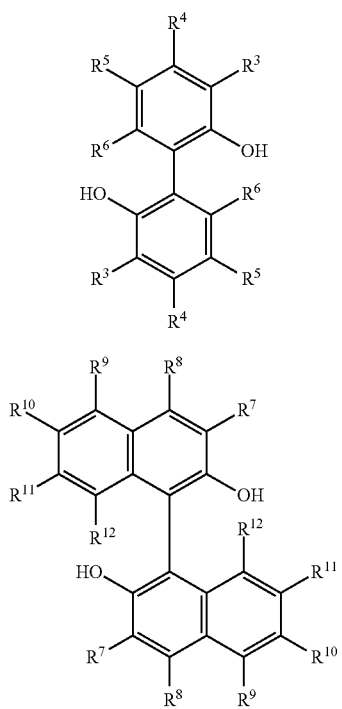

Structure III

Structure IV

-continued

Structure V wherein in Structures I-V, $R^1$ and $R^2$ are the same or different, substituted or unsubstituted, monovalent aryl groups; each of $R^3$, $R^4$, $R^5$, $R^6$, $R^7$, $R^8$, $R^9$, $R^{10}$, $R^{11}$, and $R^{12}$ is independently selected from the group consisting of hydrogen, alkyl, aryl, heteroaryl, aryloxy, heteroaryloxy, alkyloxy, alkoxyalkyl, acetal, carboaryloxy, carboalkoxy, arylcarbonyl, alkylcarbonyl, oxazole, amine, amide, nitrile, mercaptyl, and halogen groups; and O-Q-O is a divalent species of the bisaryl compound.

Embodiment 4 provides the method of any one of Embodiments 1-3, wherein the at least one side-product includes a C-phite ligand structure (CLS), having the chemical structure shown below as Structure VI, VII, or VIII,

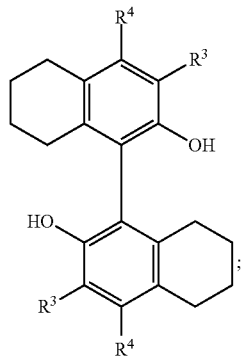

Structure V

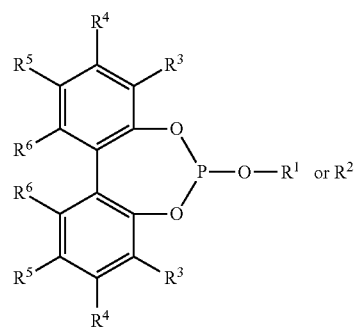

Structure VI

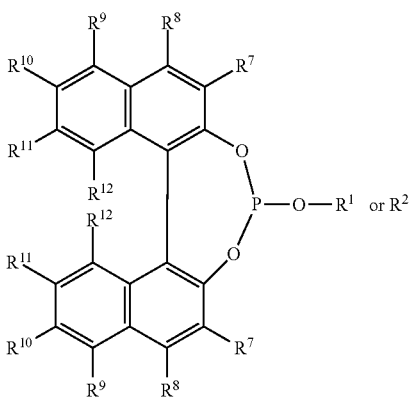

Structure VII

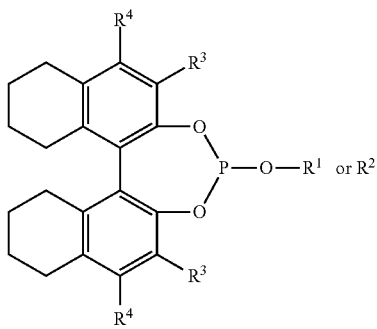

Structure VIII

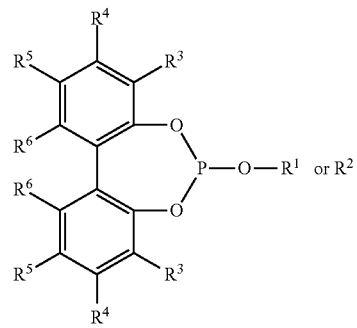

Structure VI wherein in Structures VI-VIII, $R^1$ and $R^2$ are the same or different, substituted or unsubstituted, monovalent aryl groups; $R^1$ and $R^2$ are bridged to one another or unbridged to one another; and each of $R^3$, $R^4$, $R^5$, $R^6$, $R^7$, $R^8$, $R^9$, $R^{10}$, $R^{11}$, and $R^{12}$ is independently selected from the group consisting of hydrogen, alkyl, aryl, heteroaryl, aryloxy, heteroaryloxy, alkyloxy, alkoxyalkyl, acetal, carboaryloxy, carboalkoxy, arylcarbonyl, alkylcarbonyl, oxazole, amine, amide, nitrile, mercaptyl, and halogen groups;

wherein providing a pre-determined limit for the mole percent of phosphorus present as at least one side-product in the final reaction mixture includes providing a pre-determined limit for a mole percent of phosphorus present as CLS in the final reaction mixture.

Embodiment 5 provides the method of Embodiment 4, wherein in the final reaction mixture, the percentage of phosphorus present as the phosphorus-containing ligand structure is greater than or equal to about 65%, and the percentage of phosphorus present as the CLS is less than about 5%.

Embodiment 6 provides the method of any one of Embodiments 4-5, wherein in the final reaction mixture, the percentage of phosphorus present as the phosphorus-containing ligand structure is greater than or equal to about 70%, and the percentage of phosphorus present as the CLS is less than about 3.5%.

Embodiment 7 provides the method of any one of Embodiments 1-6, wherein the at least one side-product includes a T-phite ligand structure (TLS), having the chemical structure shown below as Structure IX,

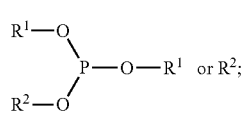

Structure IX wherein in Structure IX, $R^1$ and $R^2$ are the same or different, substituted or unsubstituted, monovalent aryl groups; and $R^1$ and $R^2$ are bridged to one another or unbridged to one another;

wherein providing a pre-determined limit for the mole percent of phosphorus present as the at least one side-product in the final reaction mixture includes providing a pre-determined limit for a mole percent of phosphorus present as TLS in the final reaction mixture.

Embodiment 8 provides the method of any one of Embodiments 1-7, wherein the at least one side-product includes a C-phite ligand structure (CLS), having the chemical structure shown below as Structure VI, VII, or VIII, Structure VII Structure VIII wherein the at least one side-product further includes a T-phite ligand structure (TLS), having the chemical structure shown below as Structure IX,

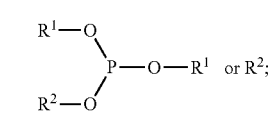

Structure IX wherein in Structures VI-VIII and IX, $R^1$ and $R^2$ are the same or different, substituted or unsubstituted, monovalent aryl groups; $R^1$ and $R^2$ are bridged to one another or unbridged to one another; and each of $R^3$, $R^4$, $R^5$, $R^6$, $R^7$, $R^8$, $R^9$, $R^{10}$, $R^{11}$, and $R^{12}$ is independently selected from the group consisting of hydrogen, alkyl, aryl, heteroaryl, aryloxy, heteroaryloxy, alkyloxy, alkoxyalkyl, acetal, carboaryloxy, carboalkoxy, arylcarbonyl, alkylcarbonyl, oxazole, amine, amide, nitrile, mercaptyl, and halogen groups;

wherein providing a pre-determined limit for the mole percent of phosphorus present as the at least one side-product in the final reaction mixture includes providing a pre-determined limit for a mole percent of phosphorus present as TLS in the final reaction mixture;

wherein providing a pre-determined limit for the mole percent of phosphorus present as the at least one side-product in the final reaction mixture includes providing a pre-determined limit for a mole percent of phosphorus present as CLS in the final reaction mixture.

Embodiment 9 provides the method of any one of Embodiments 1-8, wherein the at least one side-product includes a ligand hydrolysis product (LHP), including a product derived by a process including hydrolysis of the phosphorus-containing ligand or of the phosphorochloridite;

hydrolysis of a product derived from the phosphorus-containing ligand or from the phosphorochloridite; or reaction of the hydrolysis product of the phosphorus-containing ligand or of the phosphorochloridite, or reaction of the hydrolysis product of a product derived from the phosphorus-containing ligand or from the phosphorochloridite;

wherein providing a pre-determined limit for the mole percent of phosphorus present as the at least one side-product in the final reaction mixture includes providing a pre-determined limit for a mole percent of phosphorus present as LHP in the final reaction mixture.

Embodiment 10 provides the method of Embodiment 9, wherein in the final reaction mixture, the percentage of phosphorus present as the phosphorus-containing ligand structure is greater than or equal to about 65%, and the percentage of phosphorus present as the LHP is less than no more than about 5%.

Embodiment 11 provides the method of any one of Embodiments 9-10, wherein in the final reaction mixture, the percentage of phosphorus present as the phosphorus-containing ligand structure is greater than or equal to about 70%, and the percentage of phosphorus present as the LHP is less than no more than about 3.5%.

Embodiment 12 provides the method of any one of Embodiments 1-11, wherein the at least one side-product includes a C-phite ligand structure (CLS), having the chemical structure shown below as Structure VI, VII, or VIII,

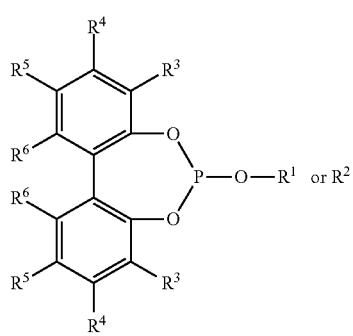

Structure VI

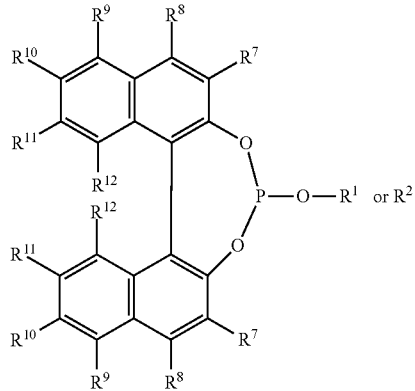

Structure VII

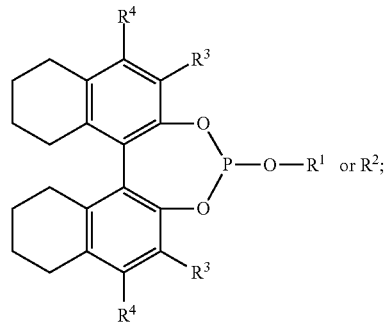

Structure VIII wherein the at least one side-product further includes a T-phite ligand structure (TLS), having the chemical structure shown below as Structure IX,

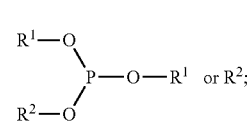

Structure IX wherein in Structures VI-VIII and IX, $R^1$ and $R^2$ are the same or different, substituted or unsubstituted, monovalent aryl groups; $R^1$ and $R^2$ are bridged to one another or unbridged to one another; and each of $R^3$, $R^4$, $R^5$, $R^6$, $R^7$, $R^8$, $R^9$, $R^{10}$, $R^{11}$, and $R^{12}$ is independently from the group consisting of hydrogen, alkyl, aryl, heteroaryl, aryloxy, heteroaryloxy, alkyloxy, alkoxyalkyl, acetal, carboaryloxy, carboalkoxy, arylcarbonyl, alkylcarbonyl, oxazole, amine, amide, nitrile, mercaptyl, and halogen groups;

wherein providing a pre-determined limit for the mole percent of phosphorus present as the at least one side-product in the final reaction mixture includes providing a pre-determined limit for a mole percent of phosphorus present as TLS in the final reaction mixture;

wherein providing a pre-determined limit for the mole percent of phosphorus present as the at least one side-product in the final reaction mixture includes providing a pre-determined limit for a mole percent of phosphorus present as CLS in the final reaction mixture;

wherein the at least one side-product further includes a ligand hydrolysis product (LHP), including a product derived by a process including hydrolysis of the phosphorus-containing ligand or of the phosphorochloridite;

hydrolysis of a product derived from the phosphorus-containing ligand or from the phosphorochloridite; or reaction of the hydrolysis product of the phosphorus-containing ligand or of the phosphorochloridite, or reaction of the hydrolysis product of a product derived from the phosphorus-containing ligand or from the phosphorochloridite;

wherein providing a pre-determined limit for the mole percent of phosphorus present as the at least one side-product in the final reaction mixture includes providing a pre-determined limit for a mole percent of phosphorus present as LHP in the final reaction mixture.

Embodiment 13 provides the method of any one of Embodiments 1-12, wherein the contacting further includes using the pre-determined limit for the mole percent of phosphorus present as the at least one side-product in the final reaction mixture to determine an amount of the X—OH to add in the first or second serial addition to cause a mole percent of phosphorus present in the first or second reaction mixtures as the at least one side-product to be less than the pre-determined limit of the mole percent of phosphorus present as the at least one side-product in the final reaction mixture.

Embodiment 14 provides the method of any one of Embodiments 2-13, wherein the contacting further includes using the pre-determined limit for the mole percent of phosphorus present as the at least one side-product in the final reaction mixture to determine an amount of the X—OH to add in the third serial addition to cause a mole percent of phosphorus present in the final reaction mixture as the at least one side-product to be less than the pre-determined limit of the mole percent of phosphorus present as the at least one side-product in the final reaction mixture.

Embodiment 15 provides the method of any one of Embodiments 1-14, wherein the amount of the X—OH added in the second serial addition is less than the amount of the X—OH added in the first serial addition; and wherein the amount of the X—OH added in the third serial addition if performed is equal to or less than the amount of the X—OH added in the second serial addition.

Embodiment 16 provides the method of Embodiment 1, wherein the amount of the X—OH added in the second or third serial addition is none.

Embodiment 17 provides the method of any one of Embodiments 1-16, wherein if the amount of the X—OH added in the second serial addition is none, then the second serial addition includes at least one of water or the alcohol having the chemical structure $R^1$—OH or $R^2$—OH; and wherein if the amount of the X—OH added in the third serial addition is none, then the third serial addition if performed includes at least one of water or the alcohol having the chemical structure $R^1$—OH or $R^2$—OH.

Embodiment 18 provides the method of any one of Embodiments 4-17, wherein using a comparison of the mole percent of phosphorus present in the first or second reaction mixture as the CLS to the pre-determined limit for the mole percent of phosphorus present as the CLS in the final reaction mixture to determine the amount of a compound to add in the second serial addition or the third serial addition if performed includes adding an amount of a compound in the second or third addition selected from the group consisting of the X—OH, water, and the alcohol having the chemical structure $R^1$—OH or $R^2$—OH sufficient to cause the mole percent of phosphorus in the second or final reaction mixture present as the CLS to be equal to or below the pre-determined limit for the mole percent of phosphorus present as the CLS in the final reaction mixture.

Embodiment 19 provides the method of Embodiment 18, wherein if the mole percent of phosphorus present in the first reaction mixture as the CLS is equal to or greater than the pre-determined limit for the mole percent of phosphorus present as the CLS in the final reaction mixture, then the second serial addition includes water or the alcohol having the chemical structure $R^1$—OH or $R^2$—OH; and wherein if the mole percent of phosphorus present in the second reaction mixture as the CLS is equal to or greater than the pre-determined limit for the mole percent of phosphorus present as the CLS in the final reaction mixture, then the third serial addition if performed includes water or the alcohol having the chemical structure $R^1$—OH or $R^2$—OH.

Embodiment 20 provides the method of any one of Embodiments 18-19, wherein if the mole percent of phosphorus present in the first reaction mixture as the CLS is equal to or greater than the pre-determined limit for the mole percent of phosphorus present as the CLS in the final reaction mixture, then the second serial addition does not include the X—OH; and wherein if the mole percent of phosphorus present in the second reaction mixture as the CLS is equal to or greater than the pre-determined limit for the mole percent of phosphorus present as the CLS in the final reaction mixture, then the third addition if performed does not include the X—OH.═

Embodiment 21 provides the method of any one of Embodiments 7-20, wherein using a comparison of the mole percent of phosphorus present in the first or second reaction mixture as the TLS to the pre-determined limit for the mole percent of phosphorus present as the TLS in the final reaction mixture to determine the amount of a compound to add in the second or third serial addition includes adding an amount of a compound in the second or third addition selected from the group consisting of the X—OH, water, and the alcohol having the chemical structure $R^1$—OH or $R^2$—OH sufficient to cause the mole percent of phosphorus in the second or final reaction mixture present as the TLS to be equal to or below the pre-determined limit for the mole percent of phosphorus present as the TLS in the final reaction mixture.

Embodiment 22 provides the method of Embodiment 21, wherein if the mole percent of phosphorus present in the first reaction mixture as the TLS is equal to or greater than the pre-determined limit for the mole percent of phosphorus present as the TLS in the final reaction mixture, then the second serial addition includes water; and wherein if the mole percent of phosphorus present in the second reaction mixture as the TLS is equal to or greater than the pre-determined limit for the mole percent of phosphorus present as the TLS in the final reaction mixture, then the third serial addition if performed includes water.

Embodiment 23 provides the method of any one of Embodiments 21-22, wherein if the mole percent of phosphorus present in the first reaction mixture as TLS is equal to or greater than the pre-determined limit for the mole percent of phosphorus present as the TLS in the final reaction mixture, then the second serial addition does not include the X—OH or the alcohol having the chemical structure $R^1$—OH or $R^2$—OH; and wherein if the mole percent of phosphorus present in the second reaction mixture as TLS is equal to or greater than the pre-determined limit for the mole percent of phosphorus present as the TLS in the final reaction mixture, then the third serial addition if performed does not include the X—OH or the alcohol having the chemical structure $R^1$—OH or $R^2$—OH.

Embodiment 24 provides the method of any one of Embodiments 9-23, wherein using a comparison of the mole percent of phosphorus present in the first or second reaction mixture as the LHP to the pre-determined limit for the mole percent of phosphorus present as the LHP in the final reaction mixture to determine the amount of a compound to add in the second or third serial addition includes adding an amount of a compound in the second or third addition selected from the group consisting of the X—OH, water, and the alcohol having the chemical structure $R^1$—OH or $R^2$—OH sufficient to cause the mole percent of phosphorus in the second or final reaction mixture present as the LHP to be equal to or below the pre-determined limit for the mole percent of phosphorus present as the LHP in the final reaction mixture.

Embodiment 25 provides the method of Embodiment 24, wherein if the mole percent of phosphorus present in the first reaction mixture as LHP is equal to or greater than the pre-determined limit for the mole percent of phosphorus present as the LHP in the final reaction mixture, then the second serial addition includes the X—OH or the alcohol having the chemical structure $R^1$—OH or $R^2$—OH; and wherein if the mole percent of phosphorus present in the second reaction mixture as LHP is equal to or greater than the pre-determined limit for the mole percent of phosphorus present as the LHP in the final reaction mixture, then the third serial addition if performed includes the X—OH or the alcohol having the chemical structure $R^1$—OH or $R^2$—OH.

Embodiment 26 provides the method of any one of Embodiments 24-25, wherein if the mole percent of phosphorus present in the first reaction mixture as LHP is equal to or greater than the pre-determined limit for the mole percent of phosphorus present as the LHP in the final reaction mixture, then the second serial addition does not include water; and wherein if the mole percent of phosphorus present in the second reaction mixture as LHP is equal to or greater than the pre-determined limit for the mole percent of phosphorus present as the LHP in the final reaction mixture, then the third serial addition if performed does not include water.

Embodiment 27 provides the method of any one of Embodiments 8-26, wherein if in the first reaction mixture both the mole percents of phosphorus present as the CLS and the TLS are equal to or greater than the respective pre-determined limits for the mole percents of phosphorus present as the CLS or the TLS in the final reaction mixture, then the second serial addition includes water; and wherein if in the second reaction mixture both the mole percents of phosphorus present as the CLS and the TLS are equal to or greater than the respective pre-determined limits for the mole percents of phosphorus present as the CLS or the TLS in the final reaction mixture, then the third serial addition if performed includes water.

Embodiment 28 provides the method of any one of Embodiments 8-27, wherein if in the first reaction mixture both the mole percents of phosphorus present as the CLS and the TLS are equal to or greater than the respective pre-determined limits for the mole percents of phosphorus present as the CLS or the TLS in the final reaction mixture, then the second serial addition does not include the X—OH or the alcohol having the chemical structure $R^1$—OH or $R^2$—OH; and wherein if in the second reaction mixture both the mole percents of phosphorus present as the CLS and the TLS are equal to or greater than the respective pre-determined limits for the mole percents of phosphorus present as the CLS or the TLS in the final reaction mixture, then if performed the third serial addition does not include the X—OH or the alcohol having the chemical structure $R^1$—OH or $R^2$—OH.

Embodiment 29 provides the method of any one of Embodiments 1-28, wherein the contacting further includes:
providing a pre-determined goal for a conversion of phosphorochloridite in the second reaction mixture;
after adding the first serial addition, determining the percent conversion of the phosphorochloridite in the first reaction mixture; and
before adding the second serial addition, using a comparison of the percent conversion of the phosphorochloridite in the first reaction mixture to the pre-determined goal for the conversion of phosphorochloridite in the second reaction mixture to determine the amount of the X—OH to add in the second serial addition.

Embodiment 30 provides the method of any one of Embodiments 8-29, wherein the contacting further includes:
providing a pre-determined goal for a conversion of phosphorochloridite in the second reaction mixture;
after adding the first serial addition, determining the percent conversion of the phosphorochloridite in the first reaction mixture; and
before adding the second serial addition, using a comparison of the percent conversion of the phosphorochloridite in the first reaction mixture to the pre-determined goal for the conversion of phosphorochloridite in the second reaction mixture to determine the amount of the X—OH to add in the second serial addition.

Embodiment 31 provides the method of Embodiment 30, wherein if in the first reaction mixture neither the mole percent of phosphorus present as the CLS nor as the TLS is equal to or above the respective pre-determined limits for the mole percents of phosphorus present as the CLS or as the TLS in the final reaction mixture, and the conversion of phosphorochloridite in the first reaction mixture is less than the pre-determined goal for the conversion of phosphorochloridite in the final reaction mixture, then the amount of the X—OH to add in the second serial addition is sufficient to make the percent conversion of the phosphorochloridite in the second reaction mixture equal to or above the pre-determined goal for the conversion of the phosphorochloridite in the second reaction mixture.

Embodiment 32 provides the method of any one of Embodiments 30-31, wherein if in the first reaction mixture neither the mole percent of phosphorus present as the CLS nor as the TLS is equal to or above the respective pre-determined limits for the mole percents of phosphorus present as the CLS or as the TLS in the final reaction mixture, and the conversion of phosphorochloridite in the first reaction mixture is less than the pre-determined goal for the conversion of phosphorochloridite in the second reaction mixture, then the second serial addition does not include water or the alcohol having the chemical structure $R^1$—OH or $R^2$—OH.

Embodiment 33 provides the method of any one of Embodiments 1 or 29, wherein if percent conversion of the phosphorochloridite in the second reaction mixture is less than about 100%, then further including adding the third serial addition to the second reaction mixture, wherein the third serial addition includes a sufficient quantity of water or the alcohol having the chemical structure $R^1$—OH or $R^2$—OH such that following the third serial addition the phosphorochloridite conversion in the final reaction mixture is about 100%.

Embodiment 34 provides the method of any one of Embodiments 7-33, further including determining the percent conversion of the phosphorochloridite in the second reaction mixture and determining the mole percent of phosphorus present as TLS in the second reaction mixture, wherein if percent conversion of the phosphorochloridite in the second reaction mixture is less than about 100%, and if in the second reaction mixture the mole percent of phosphorus present as TLS is less than the pre-determined limit for the mole percent of phosphorus present as TLS in the final reaction mixture, then further including adding the third serial addition to the second reaction mixture, wherein the third serial addition includes a sufficient quantity of the alcohol having the chemical structure $R^1$—OH or $R^2$—OH such that following the third serial addition the conversion of the phosphorochloridite in the final reaction mixture is about 100%.

Embodiment 35 provides the method of any one of Embodiments 9-34, wherein if percent conversion of the phosphorochloridite in the second reaction mixture is less than about 100%, and if in the second reaction mixture the mole percent of phosphorus present as LHP is less than the pre-determined limit for the mole percent of phosphorus present as LHP in the final reaction mixture, then further including adding a third serial addition to the second reaction mixture, wherein the third serial addition includes a sufficient quantity of water such that following the third serial addition the conversion of the phosphorochloridite in the final reaction mixture is about 100%.

Embodiment 36 provides the method of Embodiment 35, wherein following the third serial addition, in the final reaction mixture the percentage of phosphorus present as the phosphorus-containing ligand structure is greater than or equal to about 65% and the percentage of phosphorus present as the LHP is less than about 5%.

Embodiment 37 provides the method of any one of Embodiments 35-36, wherein following the third serial addition, in the final reaction mixture the percentage of phosphorus present as the phosphorus-containing ligand structure is greater than or equal to about 70%, and the percentage of phosphorus present as the LHP is less than about 3.5%.

Embodiment 38 provides the method of any one of Embodiments 1-37, wherein the contacting further includes:
providing a pre-determined goal for a conversion of phosphorochloridite in the first reaction mixture;
before adding the first serial addition, using the pre-determined goal for the conversion of phosphorochloridite in the first reaction mixture to determine the amount of the X—OH to add in the first serial addition, such that the conversion of phosphorochloridite in the first reaction mixture is at or above the pre-determined goal for the conversion of phosphorochloridite in the first reaction mixture.

Embodiment 39 provides the method of any one of Embodiments 9-38, wherein the contacting further includes:
providing a pre-determined limit for the mole percent of phosphorus present as LHP in the final reaction mixture;
after adding the first serial addition, determining the mole percent of phosphorus present as LHP in the first reaction mixture; and
before adding the second serial addition, using a comparison of the mole percent of phosphorus present as LHP in the first reaction mixture to the pre-determined limit for the mole percent of phosphorus present as LHP in the final reaction mixture to determine the composition of the second serial addition.

Embodiment 40 provides the method of any one of Embodiments 12-39, wherein the contacting further includes:
providing a pre-determined limit for the mole percent of phosphorus present as LHP in the final reaction mixture;
after adding the first serial addition, determining the mole percent of phosphorus present as LHP in the first reaction mixture; and
before adding the second serial addition, using a comparison of the mole percent of phosphorus present as LHP in the first reaction mixture to the pre-determined limit for the mole percent of phosphorus present as LHP in the final reaction mixture to determine the composition of the second serial addition.

Embodiment 41 provides the method of Embodiment 40, wherein if in the first reaction mixture the mole percent of phosphorus present as the CLS is equal to or above the pre-determined limit for the mole percent of phosphorus present as the CLS in the final reaction mixture, and in the first reaction mixture the mole percent of phosphorus present as the TLS is not equal to or above the pre-determined limit for the mole percent of phosphorus present as the TLS in the final reaction mixture, and in the first reaction mixture the mole percent of phosphorus present as LHP is equal or to greater than the pre-determined limit for the mole percent of phosphorus present as LHP in the final reaction mixture, then the second serial addition includes the alcohol having the chemical structure $R^1$—OH or $R^2$—OH.

Embodiment 42 provides the method of any one of Embodiments 40-41, wherein if in the first reaction mixture the mole percent of phosphorus present as the CLS is equal to or above the pre-determined limit for the mole percent of phosphorus present as the CLS in the final reaction mixture, and in the first reaction mixture the mole percent of phosphorus present as the TLS is not equal to or above the pre-determined limit for the mole percent of phosphorus present as the TLS in the final reaction mixture, and in the first reaction mixture the mole percent of phosphorus present as LIP is equal or to greater than the pre-determined limit for the mole percent of phosphorus present as LHP in the final reaction mixture, then the second serial addition does not include the X—OH or water.

Embodiment 43 provides the method of any one of Embodiments 8-42, wherein the contacting further includes:
providing a pre-determined goal for a conversion of phosphorochloridite in the second reaction mixture; and
after adding the first serial addition,
determining the percent conversion of the phosphorochloridite in the first reaction mixture; and
wherein if in the first reaction mixture both the mole percents of phosphorus present as the CLS and the TLS are equal to or greater than the respective pre-determined limits for the mole percents of phosphorus present as the CLS or the TLS in the final reaction mixture, then the second serial addition includes water;
wherein if in the first reaction mixture the mole percent of phosphorus present as the CLS is equal to or above the pre-determined limit for the mole percent of phosphorus present as the CLS in the final reaction mixture, and in the first reaction mixture the mole percent of phosphorus present as the TLS is not equal to or above the pre-determined limit for the mole percent of phosphorus present as the TLS in the final reaction mixture, then the second serial addition includes water or the alcohol having the chemical structure $R^1$—OH or $R^2$—OH; and
wherein if in the first reaction mixture neither the mole percent of phosphorus present as the CLS nor as the TLS is equal to or above the respective pre-determined limits for the mole percents of phosphorus present as the CLS or the TLS in the final reaction mixture, and the conversion of phosphorochloridite in the first reaction product is less than the pre-determined goal for the conversion of phosphorochloridite in the second reaction mixture, then the second serial includes a sufficient amount of the X—OH such that the percent conversion of the phosphorochloridite in the second reaction mixture is equal to or above the pre-determined goal for the conversion of the phosphorochloridite in the second reaction mixture.

Embodiment 44 provides the method of Embodiment 43, wherein if in the first reaction mixture the mole percent of phosphorus present as the CLS is equal to or above the predetermined limit for the mole percent of phosphorus present as the CLS in the final reaction mixture, and in the first reaction mixture the mole percent of phosphorus present as the TLS is not equal to or above the pre-determined limit for the mole percent of phosphorus present as the TLS in the final reaction mixture, then the second serial addition includes the alcohol having the chemical structure $R^1$—OH or $R^2$—OH.

Embodiment 45 provides the method of any one of Embodiments 12-44, wherein the contacting further includes:
providing a pre-determined goal for a conversion of phosphorochloridite in the second reaction mixture; and
after adding the first serial addition,
determining the percent conversion of the phosphorochloridite in the first reaction mixture; and
determining the mole percent of phosphorus present as LHP in the first reaction mixture;
wherein if in the first reaction mixture both the mole percents of phosphorus present as the CLS and the TLS are equal to or greater than the respective pre-determined limits for the mole percents of phosphorus present as the CLS or the TLS in the final reaction mixture, then the second serial addition includes water;
wherein if in the first reaction mixture the mole percent of phosphorus present as the CLS is equal to or above the pre-determined limit for the mole percent of phosphorus present as the CLS in the final reaction mixture, and in the first reaction mixture the mole percent of phosphorus present as the TLS is not equal to or above the pre-determined limit for the mole percent of phosphorus present as the TLS in the final reaction mixture, and in the first reaction mixture the mole percent of phosphorus present as LHP is equal or to greater than the pre-determined limit for the mole percent of phosphorus present as LHP in the final reaction mixture, then the second serial addition includes the alcohol having the chemical structure $R^1$—OH or $R^2$—OH; and
wherein if in the first reaction mixture neither the mole percent of phosphorus present as the CLS nor the TLS is equal to or above the respective pre-determined limits for the mole percents of phosphorus present as the CLS or the TLS in the final reaction mixture, and the conversion of phosphorochloridite in the first reaction product is less than the pre-determined goal for the conversion of phosphorochloridite in the second reaction mixture, then second serial addition includes X—OH in sufficient quantity such that the percent conversion of the phosphorochloridite in the second reaction mixture is equal to or above the pre-determined goal for the conversion of the phosphorochloridite in the second reaction mixture.

Embodiment 46 provides the method of Embodiment 45, wherein contacting further includes:
wherein if in the first reaction mixture the mole percent of phosphorus present as the CLS is equal to or above the pre-determined limit for the mole percent of phosphorus present as the CLS in the final reaction mixture, and in the first reaction mixture the mole percent of phosphorus present as the TLS is not equal to or above the pre-determined limit for the mole percent of phosphorus present as the TLS in the final reaction mixture, and in the first reaction mixture the mole percent of phosphorus present as LHP is not equal or to greater than the pre-determined limit for the mole percent of phosphorus present as LHP in the final reaction mixture, then the second serial addition includes water or the alcohol having the chemical structure $R^1$—OH or $R^2$—OH; and
wherein if in the first reaction mixture the mole percent of phosphorus present as the TLS is equal to or above the pre-determined limit for the mole percent of phosphorus present as the TLS in the final reaction mixture, and in the first reaction mixture the mole percent of phosphorus present as the CLS is not equal to or above the pre-determined limit for the mole percent of phosphorus present as the CLS in the final reaction mixture, and in the first reaction mixture the mole percent of phosphorus present as LHP is not equal or to greater than the pre-determined limit for LHP content in the final reaction mixture, then the second addition includes water.

Embodiment 47 provides the method of any one of Embodiments 45-46, wherein contacting further includes:
wherein if in the first reaction mixture the mole percent of phosphorus present as the CLS is equal to or above the pre-determined limit for the mole percent of phosphorus present as the CLS in the final reaction mixture, and in the first reaction mixture the mole percent of phosphorus present as the TLS is not equal to or above the pre-determined limit for the mole percent of phosphorus present as the TLS in the final reaction mixture, and in the first reaction mixture the mole percent of phosphorus present as LHP is not equal or to greater than the pre-determined limit for the mole percent of phosphorus present as LHP in the final reaction mixture, then the second serial addition does not include the X—OH; and
wherein if in the first reaction mixture the mole percent of phosphorus present as the TLS is equal to or above the pre-determined limit for the mole percent of phosphorus present as the TLS in the final reaction mixture, and in the first reaction mixture the mole percent of phosphorus present as the CLS is not equal to or above the pre-determined limit for the mole percent of phosphorus present as the CLS in the final reaction mixture, and in the first reaction mixture the mole percent of phosphorus present as LHP is not equal or to greater than the pre-determined limit for LHP content in the final reaction mixture, then the second addition does not include water or the alcohol having the chemical structure $R^1$—OH or $R^2$—OH.

Embodiment 48 provides the method of any one of Embodiments 1-47, wherein the first reaction mixture has a stoichiometric excess of phosphorochloridite.

Embodiment 49 provides the method of any one of Embodiments 1-48, wherein the contacting is carried out in the presence of a stoichiometric excess of tertiary organic amine.

Embodiment 50 provides the method of any one of Embodiments 1-49, wherein the phosphorus-containing ligand has the following chemical structure:

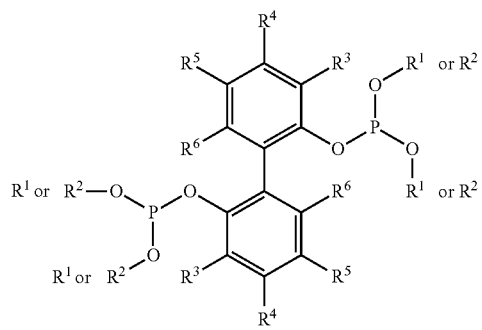

wherein $R^1$ and $R^2$ are the same or different, substituted or unsubstituted, monovalent aryl groups; each of $R^3$, $R^4$, $R^5$, $R^6$ is independently selected from the group consisting of hydrogen and $C_{1-10}$ alkyl.

Embodiment 51 provides the method of any one of Embodiments 1-50, wherein $R^2=R^1$, wherein $R^1$ is a monovalent xylene group.

Embodiment 52 provides the method of any one of Embodiments 1-51, wherein R²=R', wherein R¹ is a monovalent 2,4-xylene group Embodiment 53 provides the method of any one of Embodiments 1-52, wherein the phosphorus-containing ligand has the following chemical structure:

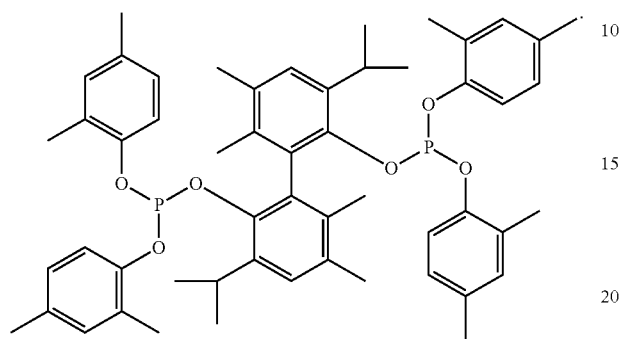

Embodiment 54 provides the method of any one of Embodiments 4-53, wherein the CLS has the following chemical structure:

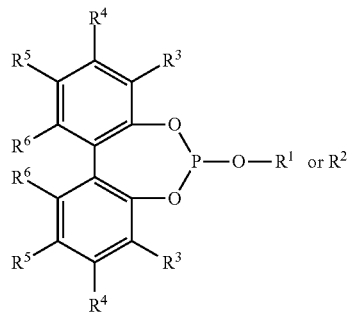

wherein R¹ and R² are the same or different, substituted or unsubstituted, monovalent aryl groups; each of R³, R⁴, R⁵, R⁶ is independently selected from the group consisting of hydrogen and $C_{1-10}$ alkyl.

Embodiment 55 provides the method of any one of Embodiments 4-54, wherein the CLS has the following chemical structure:

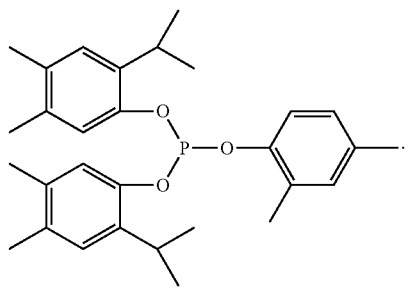

Embodiment 56 provides the method of any one of Embodiments 7-55, wherein the TLS has the chemical structure P(OR¹)₃, wherein R¹ is a substituted or unsubstituted aryl group.

Embodiment 57 provides the method of any one of Embodiments 7-56, wherein the TLS has the following chemical structure:

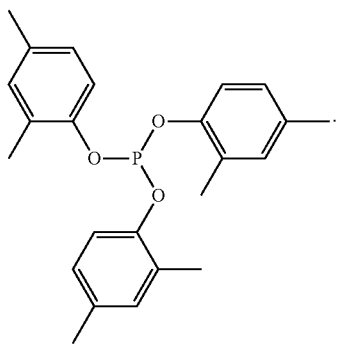 [SMILES: Cc1ccc(OP(Oc2ccc(C)cc2C)Oc2ccc(C)cc2C)c(C)c1]

Embodiment 58 provides the method of any one of Embodiments 1-57, wherein the tertiary organic amine includes a trialkylamine.

Embodiment 59 provides the method of any one of Embodiments 1-58, wherein the tertiary organic amine includes triethylamine.

Embodiment 60 provides the method of any one of Embodiments 4-59, wherein the pre-determined limit for the mole percent phosphorus present as the CLS in the final reaction mixture is less than or equal to about 5%.

Embodiment 61 provides the method of any one of Embodiments 4-60, wherein the pre-determined limit for the mole percent of phosphorus present as the CLS in the final reaction mixture is less than or equal to about 3%.

Embodiment 62 provides the method of any one of Embodiments 30, 43, or 45, wherein using a comparison of the percent conversion of the phosphorochloridite in the first reaction mixture to the pre-determined goal for the conversion of phosphorochloridite in the second reaction mixture to determine the amount of the X—OH to add in the second serial addition includes:

using at least one selectivity ratio of the phosphorochloridite to the phosphorus-containing ligand and CLS at a given conversion range to forecast a maximum percent conversion of phosphorochloridite such that at the forecasted percent conversion in the second reaction mixture the percent of phosphorus present as CLS in the second reaction mixture is less than the pre-determined limit for the percent of phosphorus present as CLS in the final reaction mixture;

setting the pre-determined goal for the conversion of phosphorochloridite in the second reaction mixture to the forecasted maximum percent conversion of the phosphorochloridite; and adding an amount of the X—OH in the second serial addition sufficient to cause the percent conversion of the phosphorochloridite in the second reaction mixture to be about equal to the pre-determined goal for the conversion of the phosphorochloridite in the second reaction mixture.

Embodiment 63 provides the method of Embodiment 62, wherein the selectivity ratio of the phosphorochloridite to the phosphorus-containing ligand and CLS at a given conversion range includes a molar selectivity ratio of CLS to phosphorus-containing ligand of about 1:6 for conversions up to about 98%.

Embodiment 64 provides the method of any one of Embodiments 62-63, wherein the selectivity ratio of the phosphorochloridite to the phosphorus-containing ligand and CLS at a given conversion range includes a molar selectivity ratio of CLS to phosphorus-containing ligand of about 1:1 for conversions of between about 98% and about 100%.

Embodiment 65 provides the method of any one of Embodiments 7-64, wherein the pre-determined limit for the mole percent of phosphorus present as the TLS in the final reaction mixture is less than or equal to about 30%.

Embodiment 66 provides the method of any one of Embodiments 7-65, wherein the pre-determined limit for the mole percent of phosphorus present as the TLS in the final reaction mixture is less than or equal to about 22%.

Embodiment 67 provides the method of any one of Embodiments 30, 43, or 45, wherein using a comparison of the percent conversion of the phosphorochloridite in the first reaction mixture to the pre-determined goal for the conversion of phosphorochloridite in the second reaction mixture to determine the amount of the X—OH to add in the second serial addition includes:

using at least one selectivity ratio of the phosphorochloridite to the phosphorus-containing ligand and TLS at a given conversion range to forecast a maximum percent conversion of phosphorochloridite such that at the forecasted percent conversion in the second reaction mixture the percent of phosphorus present as TLS in the second reaction mixture is less than the pre-determined limit for the percent of phosphorus present as TLS in the final reaction mixture;

setting the pre-determined goal for the conversion of phosphorochloridite in the second reaction mixture to the forecasted maximum percent conversion of the phosphorochloridite; and adding an amount of the X—OH in the second serial addition sufficient to cause the percent conversion of the phosphorochloridite in the second reaction mixture to be about equal to the pre-determined goal for the percent conversion of the phosphorochloridite in the second reaction mixture.

Embodiment 68 provides the method of Embodiment 67, wherein the selectivity ratio of the phosphorochloridite to the phosphorus-containing ligand and CLS at a given conversion range includes a molar selectivity ratio of CLS to phosphorus-containing ligand of about 1:6 for conversions up to about 98%.

Embodiment 69 provides the method of any one of Embodiments 67-68, wherein the selectivity ratio of the phosphorochloridite to the phosphorus-containing ligand and CLS at a given conversion range includes a molar selectivity ratio of CLS to phosphorus-containing ligand of about 1:1 for conversions of between about 98% and about 100%.

Embodiment 70 provides the method of any one of Embodiments 29, 30, 43, or 45, wherein the pre-determined goal for the conversion of phosphorochloridite in the second reaction mixture is about 95% to about 100%.

Embodiment 71 provides the method of any one of Embodiments 29, 30, 43, or 45, wherein the pre-determined goal for the conversion of phosphorochloridite in the second reaction mixture is about 96% to about 99%.

Embodiment 72 provides the method of any one of Embodiments 38-71, wherein the pre-determined goal for the conversion of phosphorochloridite in the first reaction mixture is about 85% to about 95%.

Embodiment 73 provides the method of any one of Embodiments 38-72, wherein the pre-determined goal for the conversion of phosphorochloridite in the first reaction mixture is about 90%.

Embodiment 74 provides the method of any one of Embodiments 39, 40, or 45, wherein the pre-determined limit for the mole percent of phosphorus present as LHP in the final reaction mixture is about 5%.

Embodiment 75 provides the method of any one of Embodiments 39, 40, or 45, wherein the pre-determined limit for the mole percent of phosphorus present as LHP in the final reaction mixture is about 3%.

Embodiment 76 provides the method of any one of Embodiments 1-75, wherein the contacting is carried out by at least one step selected from the group consisting of
(i) feeding the X—OH to a mixture of the phosphorochloridite and the tertiary organic amine;
(ii) feeding the X—OH and the tertiary organic amine separately to the phosphorochloridite; or
(iii) feeding the X—OH and the tertiary organic amine as a mixture to the phosphorochloridite.

Embodiment 77 provides the method of any one of Embodiments 1-76 wherein the reaction mixture further includes at least one aromatic hydrocarbon solvent.

Embodiment 78 provides the method of Embodiment 77 wherein the aromatic solvent includes toluene.

Embodiment 79 provides the method of any one of Embodiments 77-78 further including feeding the X—OH to the phosphorochloridite as a solution including the X—OH and the hydrocarbon solvent.

Embodiment 80 provides the phosphorus-containing ligand of Structure I made by the method of any one of Embodiments 1-79.

Embodiment 81 provides the method of any one of Embodiments 1-80, wherein
the first serial addition includes the X—OH in sufficient quantity such that the conversion of the phosphorochloridite in the first reaction mixture is about 85% to about 95%; and
the second serial addition includes a smaller amount of the X—OH than the amount of the X—OH added in the first serial addition.

Embodiment 82 provides the method of any one of Embodiments 1-81, wherein
the first serial addition includes X—OH in sufficient quantity such that the conversion of the phosphorochloridite in the first reaction mixture is about 85% to about 90%; and
the second serial addition includes the alcohol having the chemical structure $R^1$—OH or $R^2$—OH in sufficient quantity such that in the second reaction mixture phosphorochloridite conversion is about 100%.

Embodiment 83 provides the method of any one of Embodiments 1-82, wherein
the first serial addition includes the X—OH in sufficient quantity such that the conversion of the phosphorochloridite in the first reaction mixture is about 85% to about 95%; and
after the second serial addition, the conversion of the phosphorochloridite in the second reaction mixture is about 95% to about 99%;
the third serial addition includes water or the alcohol having the chemical structure $R^1$—OH or $R^2$—OH in sufficient quantity such that the conversion of the phosphorochloridite in the final reaction mixture is about 100%.

Embodiment 84 provides the method of any one of Embodiments 1-83, wherein the method gives a final reaction mixture that is a first final reaction mixture, wherein the method is repeated to give a second final reaction mixture, wherein the yield of the phosphorus-containing ligand in the first final reaction mixture is within 5% of the yield of the phosphorus-containing ligand in the second final reaction mixture.

Embodiment 85 provides the method of any one of Embodiments 4-84, wherein the method gives a final reaction mixture that is a first final reaction mixture, wherein the method is repeated to give a second final reaction mixture, wherein the percentage of phosphorus in the first final reaction mixture present as the phosphorus-containing ligand, TLS, and CLS, is each within 5% of the percentage of phosphorus in the second final reaction mixture present as the phosphorus-containing ligand, TLS, and CLS, respectively.

Embodiment 86 provides the method of any one of Embodiments 4-85, wherein the method gives a final reaction mixture that is a first final reaction mixture, wherein the method is repeated to give a second final reaction mixture, wherein the percentage of phosphorus in the first final reaction mixture present as CLS is within 5% of the percentage of phosphorus in the second final reaction mixture present as the CLS.

Embodiment 87 provides a method for producing a diphosphite ligand structure (DLS) having the following structure,

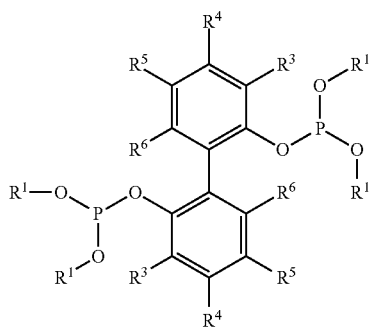

including:

contacting a phosphorochloridite having the following structure,

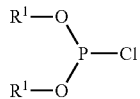

with a bisaryl compound having the following structure,

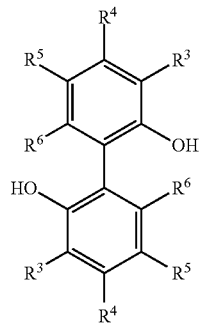

and a tertiary organic amine to provide a final reaction mixture including the diphosphite;

wherein the contacting includes providing a pre-determined limit for the mole percent of phosphorus present as C-phite ligand structure (CLS), having the chemical structure shown below, in the final reaction mixture

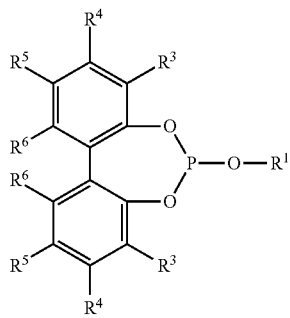

adding the bisaryl compound to the phosphorochloridite in a first serial addition such that the moles of phosphorochloridite added in the first addition is greater than the number of moles of the bisaryl compound added in the first addition, to provide a first reaction mixture;

determining the mole percent of phosphorus present in the first reaction mixture as CLS;

using a comparison of the mole percent of phosphorus present in the first reaction mixture as CLS to the pre-determined limit for the mole percent of phosphorus present as CLS to determine an amount of a compound selected from the group consisting of at least one of the bisaryl compound, water, and an alcohol having the chemical structure $R^1$—OH, to add in a second serial addition such that the mole percent of phosphorus present as CLS in a second reaction mixture is less than or equal to the pre-determined limit for the mole percent of phosphorus present as CLS in the final reaction mixture;

adding the second serial addition to the first reaction mixture, including a compound selected from the group consisting of the bisaryl compound, water, and the alcohol having the chemical structure $R^1$—OH or $R^2$—OH, to provide the second reaction mixture; and either performing third addition steps including optionally determining a mole percent of phosphorus present in the second reaction mixture as the at least one side-product;

optionally using a comparison of the mole percent of phosphorus present in the second reaction mixture as the at least one side-product to the pre-determined limit for the mole percent of phosphorus present as the at least one side-product in the final reaction mixture, to determine an amount of a compound selected from the group consisting of the X—OH, water, and the alcohol having the chemical structure $R^1$—OH or $R^2$—OH, to add in a third serial addition; and adding the third serial addition to the second reaction mixture, including a compound selected from the group consisting of the X—OH, water, and the alcohol having the chemical structure $R^1$—OH or $R^2$—OH, to provide the final reaction mixture;

or the final reaction mixture is the second reaction mixture;

wherein $R^1$ and $R^2$ are the same or different, substituted or unsubstituted, monovalent aryl groups; each of $R^3$, $R^4$, $R^5$, $R^6$ is independently selected from the group consisting of hydrogen and $C_{1-10}$ alkyl.

Embodiment 88 provides a method for producing a diphosphite ligand structure (DLS) having the following structure,

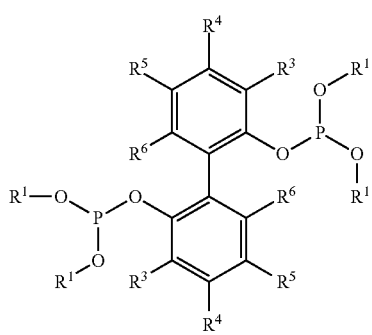

including:
contacting a phosphorochloridite having the following structure,

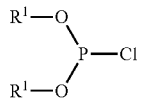

with a bisaryl compound having the following structure,

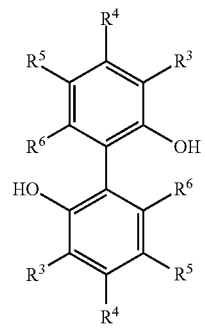

and a tertiary organic amine to provide a final reaction mixture including the diphosphite;
wherein the contacting includes
providing a pre-determined limit for the mole percent of phosphorus present as T-phite ligand structure (TLS), having the chemical structure shown below, in the final reaction mixture

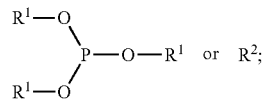

adding the bisaryl compound to the phosphorochloridite in a first serial addition such that the moles of phosphorochloridite added in the first addition is greater than the number of moles of biaryl added in the first addition, to provide a first reaction mixture;
determining the mole percent of phosphorus present in the first reaction mixture as TLS;
using a comparison of the mole percent of phosphorus present in the first reaction mixture as TLS to the pre-determined limit for the mole percent of phosphorus present as TLS to determine an amount of a compound selected from the group consisting of the bisaryl compound, water, and an alcohol having the chemical structure $R^1$—OH, to add in a second serial addition such that the mole percent of phosphorus present as TLS in a second reaction mixture is less than or equal to the pre-determined limit for the mole percent of phosphorus present as TLS in the final reaction mixture;
adding the second serial addition to the first reaction mixture, including a compound selected from the group consisting of the bisaryl compound, water, and the alcohol having the chemical structure $R^1$—OH or $R^2$—OH, to provide the second reaction mixture; and
either
performing third addition steps including
optionally determining a mole percent of phosphorus present in the second reaction mixture as the at least one side-product;
optionally using a comparison of the mole percent of phosphorus present in the second reaction mixture as the at least one side-product to the pre-determined limit for the mole percent of phosphorus present as the at least one side-product in the final reaction mixture, to determine an amount of a compound selected from the group consisting of the X—OH, water, and the alcohol having the chemical structure $R^1$—OH or $R^2$—OH, to add in a third serial addition; and
adding the third serial addition to the second reaction mixture, including a compound selected from the group consisting of the X—OH, water, and the alcohol having the chemical structure $R^1$—OH or $R^2$—OH, to provide the final reaction mixture;
or
the final reaction mixture is the second reaction mixture;
wherein $R^1$ and $R^2$ are the same or different, substituted or unsubstituted, monovalent aryl groups; and each of $R^3$, $R^4$, $R^5$, $R^6$ is independently selected from the group consisting of hydrogen and $C_{1-10}$ alkyl.

Embodiment 89 provides a method for producing a diphosphite ligand structure (DLS) having the following structure,

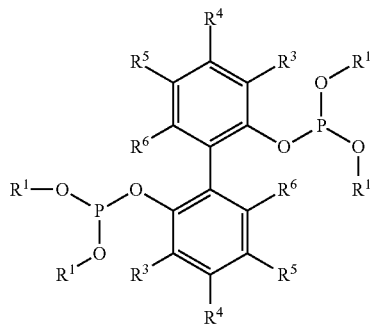

including:
contacting a phosphorochloridite having the following structure,

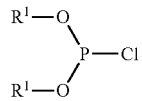

with a bisaryl compound having the following structure,

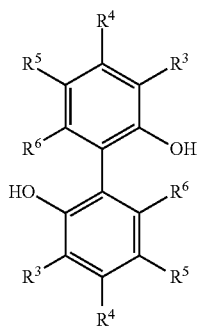

and a tertiary organic amine to provide a final reaction mixture including the diphosphite;
wherein the contacting includes
providing a pre-determined limit for the mole percent of phosphorus present as a ligand hydrolysis product (LHP) in the final reaction mixture, including a product derived by a process including
hydrolysis of the DLS or of the phosphorochloridite;
hydrolysis of a product derived from the DLS or from the phosphorochloridite; or
reaction of the hydrolysis product of the DLS or of the phosphorochloridite, or reaction of the hydrolysis product of a product derived from the DLS or from the phosphorochloridite;
adding the bisaryl compound to the phosphorochloridite in a first serial addition such that the moles of phosphorochloridite added in the first addition is greater than the number of moles of biaryl added in the first addition, to provide a first reaction mixture;
determining the mole percent of phosphorus present in the first reaction mixture as LHP;
using a comparison of the mole percent of phosphorus present in the first reaction mixture as LHP to the pre-determined limit for the mole percent of phosphorus present as LHP to determine an amount of a compound selected from the group consisting of the bisaryl compound, water, and an alcohol having the chemical structure $R^1$—OH, to add in a second serial addition such that the mole percent of phosphorus present as LHP in a second reaction mixture is less than or equal to the pre-determined limit for the mole percent of phosphorus present as LHP in the final reaction mixture;
adding the second serial addition to the first reaction mixture, including a compound selected from the group consisting of the bisaryl compound, water, and the alcohol having the chemical structure $R^1$—OH or $R^2$—OH, to provide the second reaction mixture; and
either
performing third addition steps including
optionally determining a mole percent of phosphorus present in the second reaction mixture as the at least one side-product;
optionally using a comparison of the mole percent of phosphorus present in the second reaction mixture as the at least one side-product to the pre-determined limit for the mole percent of phosphorus present as the at least one side-product in the final reaction mixture, to determine an amount of a compound selected from the group consisting of the X—OH, water, and the alcohol having the chemical structure $R^1$—OH or $R^2$—OH, to add in a third serial addition; and adding the third serial addition to the second reaction mixture, including a compound selected from the group consisting of the X—OH, water, and the alcohol having the chemical structure $R^1$—OH or $R^2$—OH, to provide the final reaction mixture;
or
the final reaction mixture is the second reaction mixture;
wherein $R^1$ and $R^2$ are the same or different, substituted or unsubstituted, monovalent aryl groups; and each of $R^3$, $R^4$, $R^5$, $R^6$ is independently selected from the group consisting of hydrogen and $C_{1-10}$ alkyl.

Embodiment 90 provides a method for producing a diphosphite ligand structure (DLS) having the following structure,

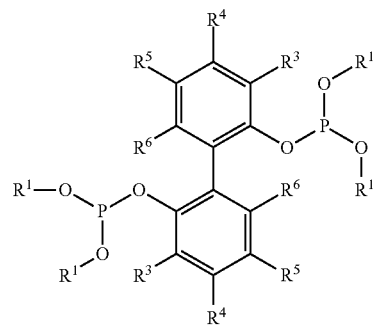

including:
contacting a phosphorochloridite having the following structure,

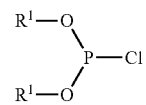

with a bisaryl compound having the following structure,

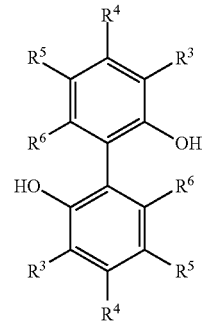

and a tertiary organic amine to provide a final reaction mixture including the diphosphite;
wherein the contacting includes
providing a pre-determined limit for the mole percent of phosphorus present as T-phite ligand structure (TLS), having the chemical structure shown below, in the final reaction mixture

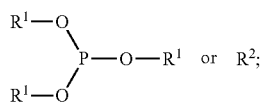

providing a pre-determined limit for the mole percent of phosphorus present as C-phite ligand structure (CLS), having the chemical structure shown below, in the final reaction mixture

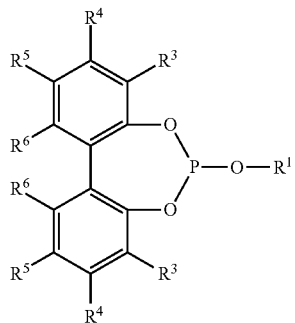

providing a pre-determined limit for the mole percent of phosphorus present as a ligand hydrolysis product (LHP) in the final reaction mixture, including a product derived by a process including
  hydrolysis of the DLS or of the phosphorochloridite;
  hydrolysis of a product derived from the DLS or from the phosphorochloridite; or
  reaction of the hydrolysis product of the DLS or of the phosphorochloridite, or reaction of the hydrolysis product of a product derived from the DLS or from the phosphorochloridite;
providing a pre-determined goal for a conversion of phosphorochloridite in the first reaction mixture;
  adding the bisaryl compound to the phosphorochloridite in a first serial addition to provide a first reaction mixture, wherein the amount of bisaryl compound added is sufficient to cause the percent conversion of the phosphorochloridite in the first reaction mixture to be equal to or greater than the pre-determined goal for a conversion of the phosphorochloridite in the first reaction mixture;
  determining the mole percent of phosphorus present in the first reaction mixture as TLS;
  determining the mole percent of phosphorus present in the first reaction mixture as CLS;
  determining the percent conversion of the phosphorochloridite in the first reaction mixture;
  wherein if in the first reaction mixture both the mole percents of phosphorus present as the CLS and the TLS are equal to or greater than the respective pre-determined limits for the mole percents of phosphorus present as the CLS or the TLS in the final reaction mixture, then the second serial addition includes water;
  wherein if in the first reaction mixture the mole percent of phosphorus present as the CLS is equal to or above the pre-determined limit for the mole percent of phosphorus present as the CLS in the final reaction mixture, and in the first reaction mixture the mole percent of phosphorus present as the TLS is not equal to or above the pre-determined limit for the mole percent of phosphorus present as the TLS in the final reaction mixture, and in the first reaction mixture the mole percent of phosphorus present as LHP is equal or to greater than the pre-determined limit for the mole percent of phosphorus present as LHP in the final reaction mixture, then the second serial addition includes the alcohol having the chemical structure $R^1$—OH or $R^2$—OH;
  wherein if in the first reaction mixture neither the mole percent of phosphorus present as the CLS nor the TLS is equal to or above the respective pre-determined limits for the mole percents of phosphorus present as the CLS or the TLS in the final reaction mixture, and the conversion of phosphorochloridite in the first reaction product is less than the pre-determined goal for the conversion of phosphorochloridite in the second reaction mixture, then second serial addition includes the bisaryl compound, wherein the quantity of the bisaryl compound to add in the second serial addition is determined using a comparison of the percent conversion of the phosphorochloridite in the first reaction mixture to the pre-determined goal for the conversion of phosphorochloridite in the second reaction mixture to determine the amount of the bisaryl compound to add in the second serial addition, including:
    using at least one selectivity ratio of the phosphorochloridite to the phosphorus-containing ligand and CLS at a given conversion range in combination with the determined mole percents of TLS and CLS in the first reaction mixture to forecast a maximum percent conversion of phosphorochloridite such that at the forecasted percent conversion in the second reaction mixture the percent of phosphorus present as CLS in the second reaction mixture is less than the pre-determined limit for the percent of phosphorus present as CLS in the final reaction mixture; and
    setting a pre-determined goal for the conversion of phosphorochloridite in the second reaction mixture to the forecasted maximum percent conversion of the phosphorochloridite;
  adding the second serial addition to the first reaction mixture, including a compound selected from the group consisting of the bisaryl compound, water, and the alcohol having the chemical structure $R^1$—OH or $R^2$—OH, to provide the second reaction mixture, wherein if bisaryl compound is added in the second serial addition then the amount of the bisaryl compound in the second serial addition is sufficient to cause the percent conversion of the phosphorochloridite in the second reaction mixture to be about equal to the pre-determined goal for the conversion of the phosphorochloridite in the second reaction mixture; and
  either
    performing third addition steps including
      optionally determining a mole percent of phosphorus present in the second reaction mixture as at least one side-product;
      optionally using a comparison of the mole percent of phosphorus present in the second reaction mixture as the at least one side-product to a pre-determined limit for the mole percent of phosphorus present as the at least one side-product in the final reaction mixture, to determine an amount of a compound selected from the group consisting of water and the alcohol having the chemical structure $R^1$—OH or $R^2$—OH, to add in a third serial addition; and
      adding the third serial addition to the second reaction mixture to provide the final reaction mixture, wherein the quantities of the one or more compounds added in the third addition are such that the conversion of the phosphorochloridite in the final reaction mixture is about 100%;

or the final reaction mixture is the second reaction mixture, wherein the quantities of the one or more compounds added in the second addition are such that conversion of the phosphorochloridite in the final reaction mixture is about 100%;

wherein $R^1$ and $R^2$ are the same or different, substituted or unsubstituted, monovalent aryl groups; and each of $R^3$, $R^4$, $R^5$, $R^6$ is independently selected from the group consisting of hydrogen and $C_{1-10}$ alkyl.

Embodiment 91 provides the apparatus or method of any one or any combination of Embodiments 1-90 optionally configured such that all elements or options recited are available to use or select from.

Exemplary Embodiments

Mole Ratios During Contacting

In some embodiments, certain mole ratios can be controlled to give optimum selectivity for formation of DLS with concurrent optimal minimization of CLS and TLS formation as well as optimal conversion of the phosphorochloridite. There are various mole ratios that can be controlled, as well as various methods of controlling mole ratios, which can result in optimization of the reaction procedure. The mole ratios described in this section are merely examples of optimization, in some examples controlling these mole ratios can be used alone to optimize the method; other optimization methods are also given outside this section (e.g. that can include at least some analysis of mole ratios) which in various embodiments can be used alone or together with the methods given in this section.

Mole ratio A is defined as the ratio of moles of phosphorochloridite in the reaction mixture to the moles of bisaryl compound fed to the reaction mixture; e.g. moles of phosphorochloridite in the reaction mixture divided by moles of bisaryl compound fed to the reaction mixture. In some embodiments, high selectivities for forming DLS can be obtained by controlling the feeding during a stage of the contacting such that mole ratio A is at least about 2. When mole ratio A is below about 2, the formation of CLS and TLS increase, which decreases the selectivity for DLS. In some embodiments, during a stage of the contacting with high phosphorochloridite conversion, for example between about 90% and about 100%, higher selectivities to the desired diphosphite can also be achieved by controlling the feeding such that mole ratio A is between about 2.1 to about 2.7. The phosphorochloridite conversion is the percent of the total moles of phosphorochloridite added to the reaction mixture that have been converted to other materials.

Mole ratio B is defined as the moles of basic nitrogen atoms from the tertiary organic amine fed to the reaction mixture to moles of phosphorochloridite in the reaction mixture; e.g. moles of basic nitrogen atoms from the tertiary organic amine fed to the reaction mixture divided by moles of phosphorochloridite in the reaction mixture. In some embodiments, high selectivities for formation of DLS can be obtained by controlling the feeding during a stage of the contacting such that mole ratio B is at least about 1. In some embodiments, when mole ratio B is below about 1, the formation of CLS and TLS can increase, decreasing selectivity for DLS formation. In some embodiments, higher selectivities to the desired diphosphite can be achieved by controlling the feeding such that the mole ratio B is between about 1.0 to about 1.5.

Mole ratios A or B can be controlled by calculating or otherwise determining the total moles of phosphorochloridite presently in the reaction mixture and calculating or otherwise determining at least one of the moles of basic nitrogen atoms from the tertiary organic amine fed to the reaction mixture or the moles of bisaryl compound fed to the reaction mixture. Once mole ratios A or B are determined, then the feed rate or quantity added of at least one of the phosphorochloridite, the tertiary organic amine, or the bisaryl compound can be adjusted accordingly. In some embodiments, in the absence of significant water (e.g. <about 300 ppm by weight $H_2O$) entering the reaction mixture with the bisaryl compound, the tertiary organic amine, aromatic hydrocarbon solvent, hydrocarbon solvent, or a combination of these members, these quantities can be calculated or otherwise determined more easily. In some embodiments, determining mole ratios A and B can include withdrawing samples to analyze the liquid reaction mixture, for example by $^{31}P$ NMR, liquid or gas chromatography, mass spectrometry, or any combination thereof.

The invention claimed is:

1. A method for producing a phosphorus-containing diphosphite ligand structure (DLS) having the chemical structure of Structure I,

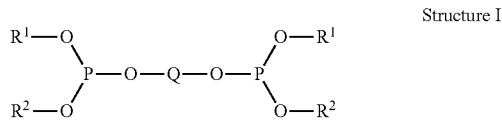

Structure I comprising:

contacting a phosphorochloridite of the following structure,

Structure II with a compound having the chemical structure X—OH and a tertiary organic amine to provide a final reaction mixture comprising the ligand structure;

wherein the contacting comprises;

providing a pre-determined limit for a mole percent of phosphorus present as at least one side-product in the final reaction mixture;

adding the X—OH to the phosphorochloridite in a first serial addition, to provide a first reaction mixture;

determining a mole percent of phosphorus present in the first reaction mixture as the at least one side-product;

using a comparison of the mole percent of phosphorus present in the first reaction mixture as the at least one side-product to the pre-determined limit for the mole percent of phosphorus present as the at least one side-product in the final reaction mixture, to determine an amount of one or more compounds selected from the group consisting of the X—OH, water, and an alcohol having the chemical structure $R^1$—OH or $R^2$—OH, to add in a second serial addition;

adding the second serial addition to the first reaction mixture, the second serial addition comprising the determined amount of one or more compounds selected from the group consisting of the X—OH, water, and the alcohol having the chemical structure R¹—OH or R²—OH, to provide a second reaction mixture; and either performing third addition steps comprising optionally determining a mole percent of phosphorus present in the second reaction mixture as the at least one side-product;

optionally using a comparison of the mole percent of phosphorus present in the second reaction mixture as the at least one side-product to the pre-determined limit for the mole percent of phosphorus present as the at least one side-product in the final reaction mixture, to determine an amount of the X—OH or of one or more compounds selected from the group consisting of water and the alcohol having the chemical structure R¹—OH or R²—OH, to add in a third serial addition; and adding the third serial addition to the second reaction mixture, comprising the X—OH or one or more compounds selected from the group consisting of water and the alcohol having the chemical structure R¹—OH or R²—OH, to provide the final reaction mixture;

or the final reaction mixture is the second reaction mixture;

wherein the X—OH is a bisaryl compound selected from the group consisting of Structure III, Structure IV, and Structure V:

Structure III

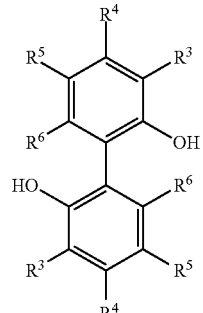

Structure IV

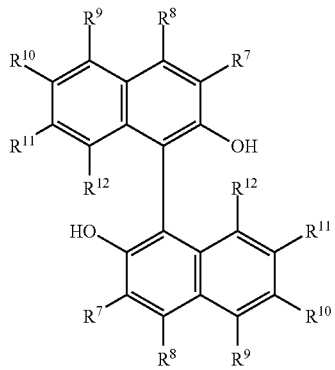

Structure V

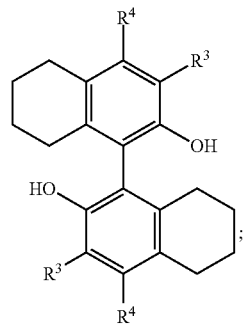

wherein Q has a structure selected from the group consisting of:

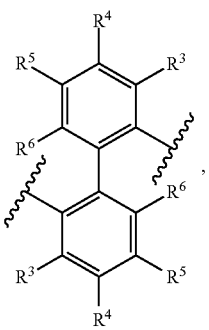

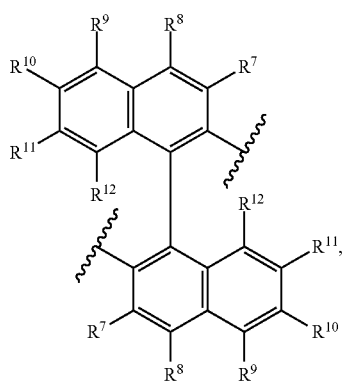

and

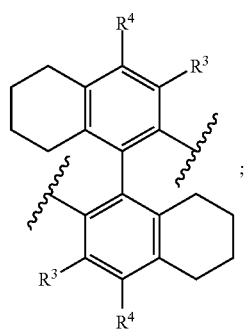

wherein the at least one side-product comprises a C-phite ligand structure (CLS), having the chemical structure shown below as Structure VI, VII, or VIII, Structure VI

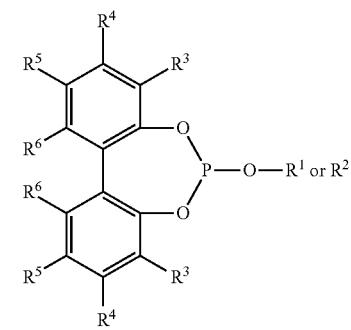

Structure VII

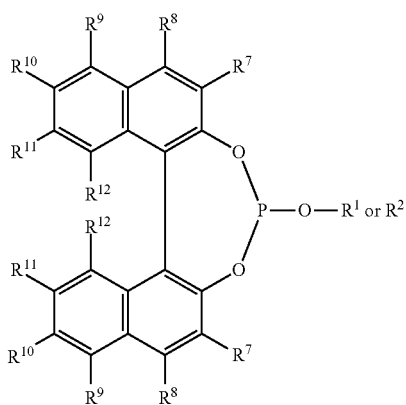

Structure VIII

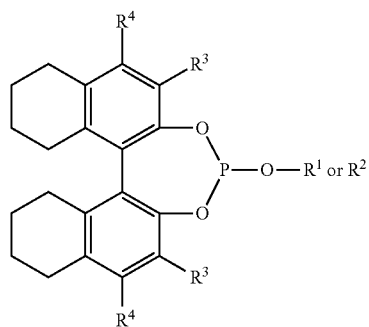

wherein providing a pre-determined limit for the mole percent of phosphorus present as at least one side-product in the final reaction mixture comprises providing a pre-determined limit for a mole percent of phosphorus present as CLS in the final reaction mixture;

wherein in Structures I-VIII, $R^1$ and $R^2$ are the same or different, substituted or unsubstituted, monovalent aryl groups; $R^1$ and $R^2$ are bridged to one another or unbridged to one another; and each of $R^3, R^4, R^5, R^6, R^7, R^8, R^9, R^{10}, R^{11}$, and $R^{12}$ is independently selected from the group consisting of hydrogen, alkyl, aryl, heteroaryl, aryloxy, heteroaryloxy, alkyloxy, alkoxyalkyl, acetal, carboaryloxy, carboalkoxy, arylcarbonyl, alkylcarbonyl, oxazole, amine, amide, nitrile, mercaptyl, and halogen groups;

wherein alkyl refers to straight chain $(C_1\text{-}C_{20})$alkyl groups, branched $(C_1\text{-}C_{20})$alkyl groups or $(C_3\text{-}C_{20})$cycloalkyl groups.

2. The method of claim 1, wherein third addition steps are performed and further comprise:

determining a mole percent of phosphorus present in the second reaction mixture as the at least one side-product; and using a comparison of the mole percent of phosphorus present in the second reaction mixture as the at least one side-product to the pre-determined limit for the mole percent of phosphorus present as the at least one side-product in the final reaction mixture, to determine an amount of the bisaryl compound or one or more compounds selected from the group consisting of water and the alcohol having the chemical structure $R^1$—OH or $R^2$—OH, to add in a third serial addition.

3. The method of claim 1, wherein the at least one side-product further comprises a T-phite ligand structure (TLS), having the chemical structure shown below as Structure IX, Structure IX

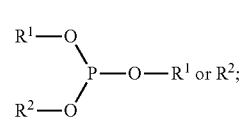

wherein in Structure IX, $R^1$ and $R^2$ are the same or different, substituted or unsubstituted, monovalent aryl groups; $R^1$ and $R^2$ are bridged to one another or unbridged to one another; and each of $R^3, R^4, R^5, R^6, R^7, R^8, R^9, R^{10}, R^{11}$, and $R^{12}$ is independently selected from the group consisting of hydrogen, alkyl, aryl, heteroaryl, aryloxy, heteroaryloxy, alkyloxy, alkoxyalkyl, acetal, carboaryloxy, carboalkoxy, arylcarbonyl, alkylcarbonyl, oxazole, amine, amide, nitrile, mercaptyl, and halogen groups;

wherein providing a pre-determined limit for the mole percent of phosphorus present as the at least one side-product in the final reaction mixture comprises providing a pre-determined limit for a mole percent of phosphorus present as TLS in the final reaction mixture;

wherein alkyl refers to straight chain $(C_1\text{-}C_{20})$alkyl groups, branched $(C_1\text{-}C_{20})$alkyl groups or $(C_3\text{-}C_{20})$cycloalkyl groups.

4. The method of claim 1, wherein the at least one side-product comprises a ligand hydrolysis product (LHP), comprising a product derived by a process comprising hydrolysis of the phosphorus-containing ligand or of the phosphorochloridite;

hydrolysis of a product derived from the phosphorus-containing ligand or from the phosphorochloridite; or reaction of the hydrolysis product of the phosphorus-containing ligand or of the phosphorochloridite, or reaction of the hydrolysis product of a product derived from the phosphorus-containing ligand or from the phosphorochloridite;

wherein providing a pre-determined limit for the mole percent of phosphorus present as the at least one side-product in the final reaction mixture comprises providing a pre-determined limit for a mole percent of phosphorus present as LHP in the final reaction mixture.

5. The method of claim 1, wherein the contacting further comprises using the pre-determined limit for the mole percent of phosphorus present as the at least one side-product in the final reaction mixture to determine an amount of the X—OH to add in the first or second serial addition to cause a mole percent of phosphorus present in the first or second reaction mixtures as the at least one side-product to be less than the pre-determined limit of the mole percent of phosphorus present as the at least one side-product in the final reaction mixture.

6. The method of claim 1, wherein if the amount of the X—OH added in the second serial addition is none, then the second serial addition comprises at least one of water and the alcohol having the chemical structure $R^1$—OH or $R^2$—OH; and wherein if the amount of the X—OH added in the third serial addition is none, then the third serial addition if performed comprises at least one of water and the alcohol having the chemical structure $R^1$—OH or $R^2$—OH.

7. The method of claim 1, wherein using a comparison of the mole percent of phosphorus present in the first or second reaction mixture as the CLS to the pre-determined limit for the mole percent of phosphorus present as the CLS in the final reaction mixture to determine the amount of a compound to add in the second serial addition or the third serial addition if performed comprises
adding an amount of one or more compounds in the second or third addition selected from the group consisting of the X—OH, water, and the alcohol having the chemical structure $R^1$—OH or $R^2$—OH sufficient to cause the mole percent of phosphorus in the second or final reaction mixture present as the CLS to be equal to or below the pre-determined limit for the mole percent of phosphorus present as the CLS in the final reaction mixture, or
adding an amount of the X—OH or of one or more compounds in the third addition selected from the group consisting of water and the alcohol having the chemical structure $R^1$—OH or $R^2$—OH sufficient to cause the mole percent of phosphorus in the final reaction mixture present as the CLS to be equal to or below the pre-determined limit for the mole percent of phosphorus present as the CLS in the final reaction mixture.

8. The method of claim 4, wherein using a comparison of the mole percent of phosphorus present in the first or second reaction mixture as the LHP to the pre-determined limit for the mole percent of phosphorus present as the LHP in the final reaction mixture to determine the amount of a compound to add in the second or third serial addition comprises
adding an amount of one or more compounds in the second addition selected from the group consisting of the X—OH, water, and the alcohol having the chemical structure $R^1$—OH or $R^2$—OH sufficient to cause the mole percent of phosphorus in the second or final reaction mixture present as the LHP to be equal to or below the pre-determined limit for the mole percent of phosphorus present as the LHP in the final reaction mixture, or
adding an amount of the X—OH or one or more compounds selected from the group consisting of water and the alcohol having the chemical structure $R^1$—OH or $R^2$—OH sufficient to cause the mole percent of phosphorus in the final reaction mixture present as the LHP, to be equal to or below the pre-determined limit for the mole percent of phosphorus present as the LHP in the final reaction mixture.

9. The method of claim 1, wherein the contacting further comprises:
providing a pre-determined goal for a conversion of phosphorochloridite in the second reaction mixture;
after adding the first serial addition, determining the percent conversion of the phosphorochloridite in the first reaction mixture; and
before adding the second serial addition, using a comparison of the percent conversion of the phosphorochloridite in the first reaction mixture to the pre-determined goal for the conversion of phosphorochloridite in the second reaction mixture to determine the amount of the X—OH to add in the second serial addition.

10. The method of claim 1, further comprising determining the percent conversion of the phosphorochloridite in the second reaction mixture, wherein if the percent conversion of the phosphorochloridite in the second reaction mixture is less than about 100%, then further comprising adding the third serial addition to the second reaction mixture, wherein the third serial addition comprises a sufficient quantity of water or the alcohol having the chemical structure $R^1$—OH or $R^2$—OH such that following the third serial addition the phosphorochloridite conversion in the final reaction mixture is about 100%.

11. The method of claim 1, wherein the contacting further comprises:
providing a pre-determined goal for a conversion of phosphorochloridite in the first reaction mixture;
before adding the first serial addition, using the pre-determined goal for the conversion of phosphorochloridite in the first reaction mixture to determine the amount of the X—OH to add in the first serial addition, such that the conversion of phosphorochloridite in the first reaction mixture is at or above the pre-determined goal for the conversion of phosphorochloridite in the first reaction mixture.

12. The method of claim 4, wherein the contacting further comprises:
after adding the first serial addition, determining the mole percent of phosphorus present as LHP in the first reaction mixture; and
before adding the second serial addition, using a comparison of the mole percent of phosphorus present as LHP in the first reaction mixture to the pre-determined limit for the mole percent of phosphorus present as LHP in the final reaction mixture to determine the composition of the second serial addition.

13. The method of claim 3, wherein the contacting further comprises:
providing a pre-determined goal for a conversion of phosphorochloridite in the second reaction mixture; and
after adding the first serial addition,
determining the percent conversion of the phosphorochloridite in the first reaction mixture; and
wherein if in the first reaction mixture both the mole percents of phosphorus present as the CLS and the TLS are equal to or greater than the respective pre-determined limits for the mole percents of phosphorus present as the CLS or the TLS in the final reaction mixture, then the second serial addition comprises water;
wherein if in the first reaction mixture the mole percent of phosphorus present as the CLS is equal to or above the pre-determined limit for the mole percent of phosphorus present as the CLS in the final reaction mixture, and in the first reaction mixture the mole percent of phosphorus present as the TLS is not equal to or above the pre-determined limit for the mole percent of phosphorus present as the TLS in the final reaction mixture, then the second serial addition comprises water or the alcohol having the chemical structure $R^1$—OH or $R^2$—OH; and
wherein if in the first reaction mixture neither the mole percent of phosphorus present as the CLS nor as the TLS is equal to or above the respective pre-determined limits for the mole percents of phosphorus present as the CLS or the TLS in the final reaction mixture, and the conversion of phosphorochloridite in the first reaction product is less than the pre-determined goal for the conversion of phosphorochloridite in the second reaction mixture, then the second serial addition comprises a sufficient amount of the X—OH such that the percent conversion of the phosphorochloridite in the second reaction mixture is equal to or above the pre-determined goal for the conversion of the phosphorochloridite in the second reaction mixture.

14. The method of claim 1 wherein the at least one side-product further comprises a T-phite ligand structure (TLS), having the chemical structure shown below as Structure IX,

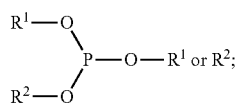

Structure IX wherein in Structure IX, $R^1$ and $R^2$ are the same or different, substituted or unsubstituted, monovalent aryl groups; $R^1$ and $R^2$ are bridged to one another or unbridged to one another; and each of $R^3$, $R^4$, $R^5$, $R^6$, $R^7$, $R^8$, $R^9$, $R^{10}$, $R^{11}$, and $R^{12}$ is independently selected from the group consisting of hydrogen, alkyl, aryl, heteroaryl, aryloxy, heteroaryloxy, alkyloxy, alkoxyalkyl, acetal, carboaryloxy, carboalkoxy, arylcarbonyl, alkylcarbonyl, oxazole, amine, amide, nitrile, mercaptyl, and halogen groups;
wherein providing a pre-determined limit for the mole percent of phosphorus present as the at least one side-product in the final reaction mixture comprises providing a pre-determined limit for a mole percent of phosphorus present as TLS in the final reaction mixture;
wherein the at least one side-product further comprises a ligand hydrolysis product (LHP), comprising a product derived by a process comprising
hydrolysis of the phosphorus-containing ligand or of the phosphorochloridite;
hydrolysis of a product derived from the phosphorus-containing ligand or from the phosphorochloridite; or
reaction of the hydrolysis product of the phosphorus-containing ligand or of the phosphorochloridite, or reaction of the hydrolysis product of a product derived from the phosphorus-containing ligand or from the phosphorochloridite;
wherein providing a pre-determined limit for the mole percent of phosphorus present as the at least one side-product in the final reaction mixture comprises providing a pre-determined limit for a mole percent of phosphorus present as LHP in the final reaction mixture;
wherein the contacting further comprises:
providing a pre-determined goal for a conversion of phosphorochloridite in the second reaction mixture; and
after adding the first serial addition,
determining the percent conversion of the phosphorochloridite in the first reaction mixture; and
determining the mole percent of phosphorus present as LHP in the first reaction mixture;
wherein if in the first reaction mixture both the mole percents of phosphorus present as the CLS and the TLS are equal to or greater than the respective pre-determined limits for the mole percents of phosphorus present as the CLS or the TLS in the final reaction mixture, then the second serial addition comprises water;
wherein if in the first reaction mixture the mole percent of phosphorus present as the CLS is equal to or above the pre-determined limit for the mole percent of phosphorus present as the CLS in the final reaction mixture, and in the first reaction mixture the mole percent of phosphorus present as the TLS is not equal to or above the pre-determined limit for the mole percent of phosphorus present as the TLS in the final reaction mixture, and in the first reaction mixture the mole percent of phosphorus present as LHP is equal or to greater than the pre-determined limit for the mole percent of phosphorus present as LHP in the final reaction mixture, then the second serial addition comprises the alcohol having the chemical structure $R^1$—OH or $R^2$—OH; and wherein if in the first reaction mixture neither the mole percent of phosphorus present as the CLS nor the TLS is equal to or above the respective pre-determined limits for the mole percents of phosphorus present as the CLS or the TLS in the final reaction mixture, and the conversion of phosphorochloridite in the first reaction product is less than the pre-determined goal for the conversion of phosphorochloridite in the second reaction mixture, then second serial addition comprises X—OH in sufficient quantity such that the percent conversion of the phosphorochloridite in the second reaction mixture is equal to or above the pre-determined goal for the conversion of the phosphorochloridite in the second reaction mixture.

15. The method of claim 1, wherein the pre-determined limit for the mole percent phosphorus present as the CLS in the final reaction mixture is less than or equal to about 5%.

16. The method of claim 9, wherein the pre-determined goal for the conversion of phosphorochloridite in the second reaction mixture is about 95% to about 100%.

17. The method of claim 11, wherein the pre-determined goal for the conversion of phosphorochloridite in the first reaction mixture is about 85% to about 95%.

18. The method of claim 12, wherein the pre-determined limit for the mole percent of phosphorus present as LHP in the final reaction mixture is about 5%.

19. A method for producing a diphosphite ligand structure (DLS) having the following structure,

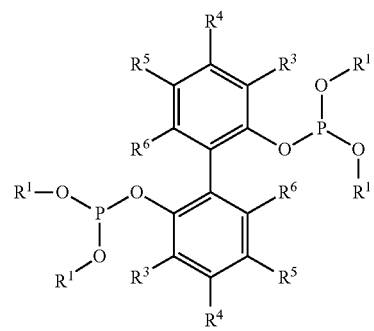

comprising:
contacting a phosphorochloridite having the following structure,

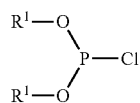

with a bisaryl compound having the following structure,

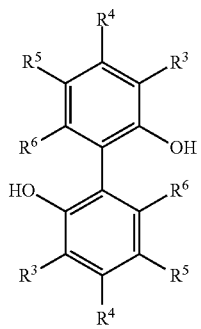

and a tertiary organic amine to provide a final reaction mixture comprising the diphosphite;
  wherein the contacting comprises
    providing a pre-determined limit for the mole percent of phosphorus present as T-phite ligand structure (TLS), having the chemical structure shown below, in the final reaction mixture

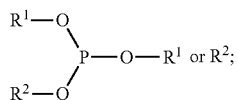

providing a pre-determined limit for the mole percent of phosphorus present as C-phite ligand structure (CLS), having the chemical structure shown below, in the final reaction mixture

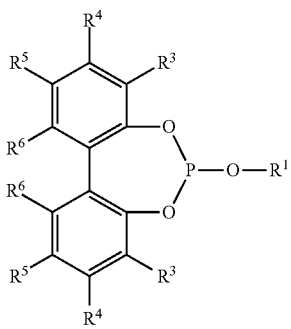

providing a pre-determined limit for the mole percent of phosphorus present as a ligand hydrolysis product (LHP) in the final reaction mixture, comprising a product derived by a process comprising
      hydrolysis of the DLS or of the phosphorochloridite;
      hydrolysis of a product derived from the DLS or from the phosphorochloridite; or
      reaction of the hydrolysis product of the DLS or of the phosphorochloridite, or reaction of the hydrolysis product of a product derived from the DLS or from the phosphorochloridite;
    providing a pre-determined goal for a conversion of phosphorochloridite in the first reaction mixture;
    adding the bisaryl compound to the phosphorochloridite in a first serial addition to provide a first reaction mixture, wherein the amount of bisaryl compound added is sufficient to cause the percent conversion of the phosphorochloridite in the first reaction mixture to be equal to or greater than the pre-determined goal for a conversion of the phosphorochloridite in the first reaction mixture;
    determining the mole percent of phosphorus present in the first reaction mixture as TLS;
    determining the mole percent of phosphorus present in the first reaction mixture as CLS;
    determining the mole percent of phosphorus present in the first reaction mixture as LHP;
    determining the percent conversion of the phosphorochloridite in the first reaction mixture;
    wherein if in the first reaction mixture both the mole percents of phosphorus present as the CLS and the TLS are equal to or greater than the respective pre-determined limits for the mole percents of phosphorus present as the CLS or the TLS in the final reaction mixture, then the second serial addition comprises water;
    wherein if in the first reaction mixture the mole percent of phosphorus present as the CLS is equal to or above the pre-determined limit for the mole percent of phosphorus present as the CLS in the final reaction mixture, and in the first reaction mixture the mole percent of phosphorus present as the TLS is not equal to or above the pre-determined limit for the mole percent of phosphorus present as the TLS in the final reaction mixture, and in the first reaction mixture the mole percent of phosphorus present as LHP is equal or to greater than the pre-determined limit for the mole percent of phosphorus present as LHP in the final reaction mixture, then the second serial addition comprises the alcohol having the chemical structure $R^1$—OH or $R^2$—OH;
    wherein if in the first reaction mixture neither the mole percent of phosphorus present as the CLS nor the TLS is equal to or above the respective pre-determined limits for the mole percents of phosphorus present as the CLS or the TLS in the final reaction mixture, and the conversion of phosphorochloridite in the first reaction product is less than the pre-determined goal for the conversion of phosphorochloridite in the second reaction mixture, then second serial addition comprises the bisaryl compound, wherein the quantity of the bisaryl compound to add in the second serial addition is determined using a comparison of the percent conversion of the phosphorochloridite in the first reaction mixture to the pre-determined goal for the conversion of phosphorochloridite in the second reaction mixture to determine the amount of the bisaryl compound to add in the second serial addition, comprising:
      using at least one selectivity ratio of the phosphorochloridite to the phosphorus-containing ligand and CLS at a given conversion range in combination with the determined mole percents of TLS and CLS in the first reaction mixture to forecast a maximum percent conversion of phosphorochloridite such that at the forecasted percent conversion in the second reaction mixture the percent of phosphorus present as CLS in the second reaction mixture is less than the pre-determined limit for the percent of phosphorus present as CLS in the final reaction mixture; and setting a pre-determined goal for the conversion of phosphorochloridite in the second reaction mixture to the forecasted maximum percent conversion of the phosphorochloridite;

adding the second serial addition to the first reaction mixture, comprising one or more compounds selected from the group consisting of the bisaryl compound, water, and the alcohol having the chemical structure $R^1$—OH or $R^2$—OH, to provide the second reaction mixture, wherein if bisaryl compound is added in the second serial addition then the amount of the bisaryl compound in the second serial addition is sufficient to cause the percent conversion of the phosphorochloridite in the second reaction mixture to be about equal to the pre-determined goal for the conversion of the phosphorochloridite in the second reaction mixture; and either performing third addition steps comprising optionally determining a mole percent of phosphorus present in the second reaction mixture as at least one side-product;

optionally using a comparison of the mole percent of phosphorus present in the second reaction mixture as the at least one side-product to a pre-determined limit for the mole percent of phosphorus present as the at least one side-product in the final reaction mixture, to determine an amount of one or more compounds selected from the group consisting of water and the alcohol having the chemical structure $R^1$—OH or $R^2$—OH, to add in a third serial addition; and adding the third serial addition to the second reaction mixture to provide the final reaction mixture, wherein the quantities of the one or more compounds added in the third addition are such that the conversion of the phosphorochloridite in the final reaction mixture is about 100%;

or the final reaction mixture is the second reaction mixture, wherein the quantities of the one or more compounds added in the second addition are such that conversion of the phosphorochloridite in the final reaction mixture is about 100%;

wherein $R^1$ and $R^2$ are the same or different, substituted or unsubstituted, monovalent aryl groups; and each of $R^3$, $R^4$, $R^5$, $R^6$ is independently selected from the group consisting of hydrogen and $C_{1-10}$ alkyl wherein alkyl refers to straight chain $(C_1$-$C_{10})$alkyl groups, branched $(C_1$-$C_{20})$alkyl groups or $(C_3$-$C_{20})$cycloalkyl groups.

* * * * *